(12) United States Patent
Donhowe et al.

(10) Patent No.: US 11,654,207 B2
(45) Date of Patent: May 23, 2023

(54) METHODS FOR PRODUCING FLEXIBLE ULTRAVIOLET LIGHT GENERATION SHEETS AND SYSTEMS

(71) Applicant: W. L. Gore & Associates, Inc., Newark, DE (US)

(72) Inventors: Mark Donhowe, Newark, DE (US); Scott P. Fillery, Newark, DE (US); John M. Squeri, Newark, DE (US); David C. Keach, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 208 days.

(21) Appl. No.: 16/769,149

(22) PCT Filed: Dec. 11, 2017

(86) PCT No.: PCT/US2017/065590
§ 371 (c)(1),
(2) Date: Jun. 2, 2020

(87) PCT Pub. No.: WO2019/117853
PCT Pub. Date: Jun. 20, 2019

(65) Prior Publication Data
US 2021/0213147 A1 Jul. 15, 2021

(51) Int. Cl.
*A61L 2/10* (2006.01)
*A61L 2/08* (2006.01)
(Continued)

(52) U.S. Cl.
CPC .................. *A61L 2/10* (2013.01); *A61L 2/088* (2013.01); *H01L 25/0753* (2013.01); *H01L 33/005* (2013.01); *H01L 33/60* (2013.01)

(58) Field of Classification Search
CPC ... H01L 25/0753; H01L 33/005; H01L 33/60; A61L 2/088; A61L 2/10
See application file for complete search history.

(56) References Cited

U.S. PATENT DOCUMENTS 8,461,602 B2   6/2013  Lerman et al.
2011/0163683 A1  7/2011  Steele et al.
(Continued)

FOREIGN PATENT DOCUMENTS

EP   2 004 554 A1   12/2008
JP   2000-285714 A  10/2000
(Continued)

OTHER PUBLICATIONS

International Search Report and Written Opinion from International Application No. PCT/US2017/065590 dated Nov. 21, 2018.

*Primary Examiner* — Anne M Hines

(57) ABSTRACT

Described are light generating devices employing ultraviolet (UV) light emitting diodes and one or more UV active materials, such as UV reflective materials, UV scattering materials, and UV transparent materials. A UV light generation system, may include a plurality of UV light emitting diodes arranged across a surface having a diffuse UV reflective layer. The UV light generation system may be arranged to enclose a fluid pathway or may be arranged as a liner of a container or vessel for use in disinfecting, purifying, or sterilizing fluid, particles or objects in the fluid pathway, container, or vessel by exposure of the fluid, particles or objects to UV light generated by the UV light emitting diodes.

20 Claims, 30 Drawing Sheets

(51) Int. Cl.
*H01L 25/075* (2006.01)
*H01L 33/00* (2010.01)
*H01L 33/60* (2010.01)

(56) References Cited

U.S. PATENT DOCUMENTS

| | | | |
|---|---|---|---|
| 2012/0094406 A1* | 4/2012 | Patel | .................... H01L 33/505 257/E33.061 |
| 2015/0060905 A1 | 3/2015 | Nam et al. | |
| 2017/0062674 A1 | 3/2017 | Kwon et al. | |

FOREIGN PATENT DOCUMENTS

| | | |
|---|---|---|
| JP | 2007-054465 A | 3/2007 |
| KR | 10-2004-0104754 A | 12/2004 |
| KR | 10-1121687 B1 | 3/2012 |
| KR | 10-2015-0028157 A | 3/2015 |
| WO | 2013/118076 A1 | 8/2013 |
| WO | 2017/100225 A1 | 6/2017 |
| WO | 2017/171460 A1 | 10/2017 |

* cited by examiner

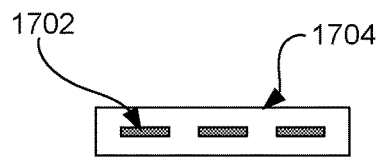
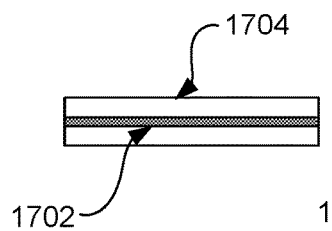
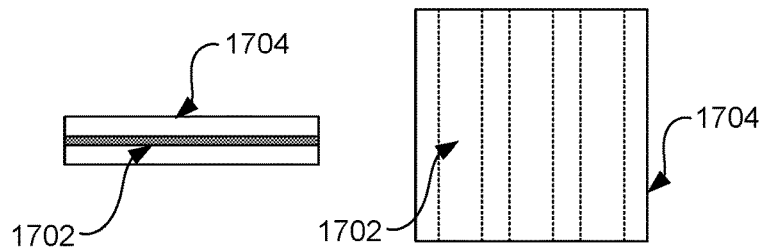
FIG. 17A (1)  FIG. 17A (2)  FIG. 17A (3)
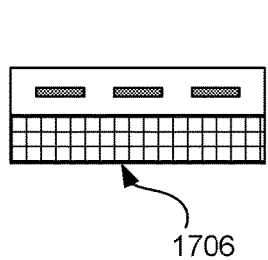
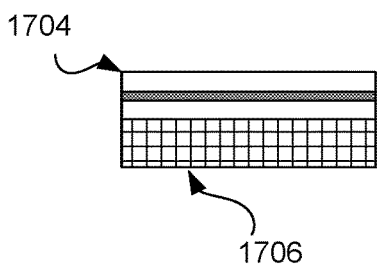
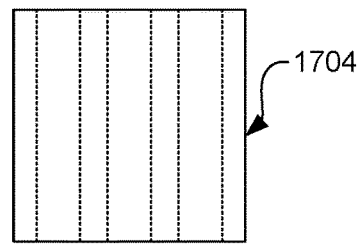
FIG. 17B (1)  FIG. 17B (2)  FIG. 17B (3)
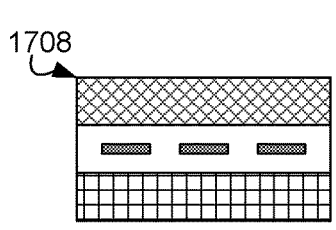
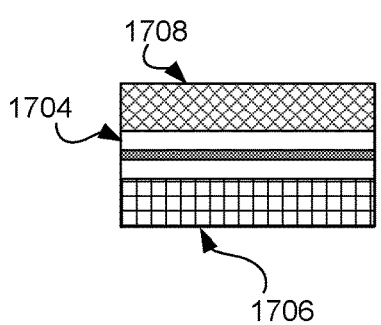
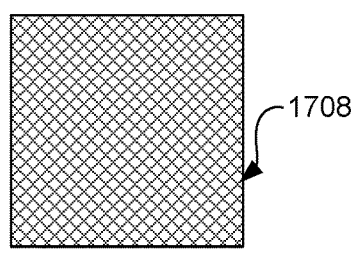
FIG. 17C (1)  FIG. 17C (2)  FIG. 17C (3)

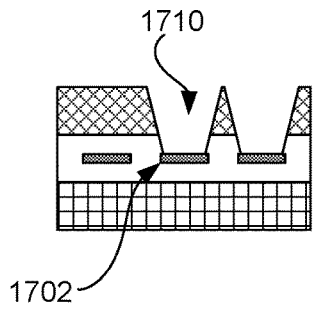 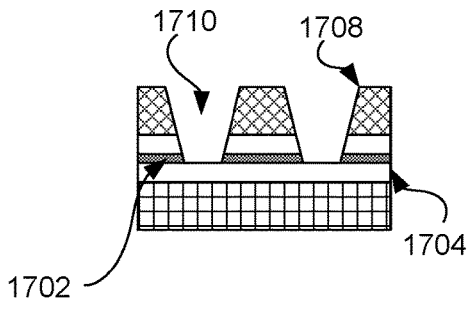 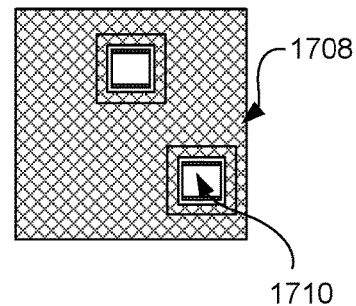
FIG. 17D (1)    FIG. 17D (2)    FIG. 17D (3)
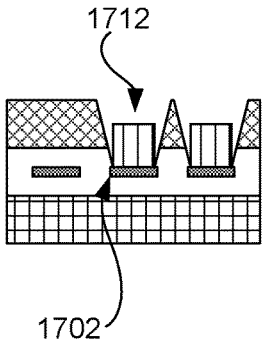 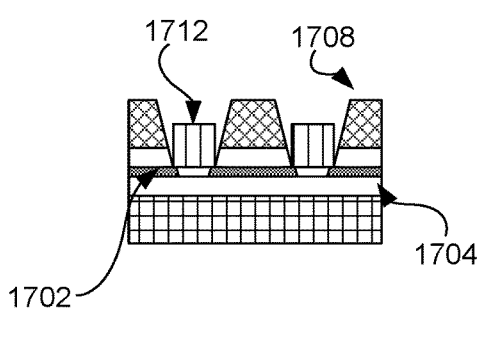 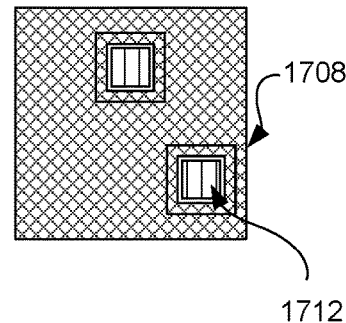
FIG. 17E (1)    FIG. 17E (2)    FIG. 17E (3)
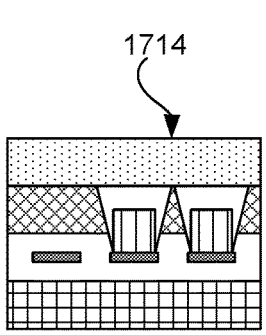 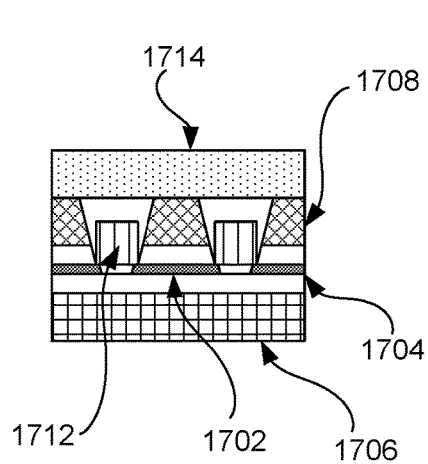 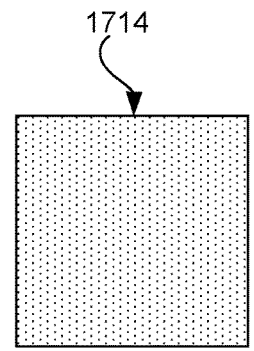
FIG. 17F (1)    FIG. 17F (2)    FIG. 17F (3)

METHODS FOR PRODUCING FLEXIBLE ULTRAVIOLET LIGHT GENERATION SHEETS AND SYSTEMS

RELATED APPLICATIONS

The present application is a national phase filing under 35 USC 371 of International Application No. PCT/US2017/065590, filed on Dec. 11, 2017, the entire contents and disclosures of which are hereby incorporated by reference.

TECHNICAL FIELD

The present invention relates generally to ultraviolet (UV) light generating sheets and systems, and methods for making such sheets and systems. More specifically, but not by way of limitation, the following describes devices generating UV light and for treating, e.g., disinfecting, fluids or materials by exposing the fluids or materials to UV light.

BACKGROUND

Exposure to UV light, corresponding to electromagnetic radiation with wavelengths of between about 100 nm and about 400 nm, is known to induce degradation to many materials, including biological materials. UV light can break down DNA so that a cell cannot reproduce and can also degrade toxins, making UV light useful for disinfection or purification purposes. The use of UV light to kill pathogens, such as microorganisms, has found applications in disinfecting air, water, food, beverages, and blood components. UV disinfection has many advantages over alternative methods, such as chlorine-based disinfection. For example, UV exposure does not introduce toxins or residues into the process and may not alter the chemical composition, functionality, taste, odor, or pH of the product.

Traditional sources of UV light include mercury or xenon arc lamps. Mercury lamps, for example, may generate UV light with wavelengths of 253.7 nm and 185 nm. More recently, UV light emitting diodes (LEDs) have been developed that offer the advantages of reduced power consumption, reduced size, longer lifetime, and instant turn on as compared to traditional mercury or xenon lamp sources. UV-LEDs may generate UV light with wavelengths from 200 nm to 400 nm, for example.

A typical UV treatment system includes an inlet port, a treatment chamber in which air or water flows through the chamber, a UV light source that emits radiation that impinges the volume of the treatment chamber, and an exit port. Due to their small size, however, toxins and pathogens can be shielded from UV light exposure, so improved UV light treatment systems and methods are useful.

U.S. Pat. No. 9,409,797 discloses a device for treating a medium using UV radiation including a treatment chamber to accommodate the medium. An LED UV radiation source provides UV radiation. A chamber-forming structure has a stiffening base structure with at least one orifice formed therein and has a UV-radiation-transmissive film. The base structure defines a placement of the UV-radiation transmissive film. The chamber-forming structure separates the treatment chamber from the LED UV radiation source, and the UV radiation is introduced into the treatment chamber through the chamber-forming structure.

U.S. Pat. No. 9,586,838 discloses an LED-based system for purifying a fluid flowing through a pipe, comprising means for mounting the system on the pipe, a housing, a pliant carrier structure comprising a plurality of LEDs arranged flush with a first surface of the structure and configured to emit radiation in the UV range, wherein when the system is pipe-mounted, the structure is detachably arranged within the housing, and the structure adopts a substantially tubular shape within the housing with the first surface delimiting a purifying chamber, wherein the purifying chamber is in fluid communication with the pipe so that the fluid flowing through the pipe passes, prior to being dispensed, through the purifying chamber where it is exposed to UV radiation of the energized LEDs.

U.S. Publication 2017/0281812 describes approaches for treating a fluid transport conduit with ultraviolet radiation. A light guiding unit, operatively coupled to a set of ultraviolet radiation sources, encloses the fluid transport conduit. The light guiding unit directs ultraviolet radiation emitted from the ultraviolet radiation sources to ultraviolet transparent sections on an outer surface of the fluid transport conduit. The emitted ultraviolet radiation passes through the ultraviolet transparent sections, penetrates the fluid transport conduit and irradiates the internal walls. A control unit adjusts a set of operating parameters of the ultraviolet radiation sources as a function of the removal of contaminants from the internal walls of the fluid transport conduit.

There continues to be a need for improved UV treatment systems.

SUMMARY

In the embodiments described herein, the present invention provides treatment, disinfection, or purification sheets and systems employing ultraviolet (UV) light emitting diodes and one or more UV active materials, such as UV reflective materials, UV scattering materials, and UV transparent materials, and methods of making UV light generation sheets and systems.

Disclosed UV light generation systems (also referred to as UV treatment systems and UV emitting systems) include those comprising flexible circuits featuring multiple UV-LEDs and, and other UV active layers, such as UV diffuse reflective layers or UV transmitting scattering layers. The UV light generation systems may also further include additional overlayers or underlayers, such as a supporting layer, a UV transparent overlayer, or a UV transparent encapsulating layer. The disclosed UV light generation systems may be submersed in a fluid, such as a liquid or a gas, and used to treat the material of the fluid or other materials suspended in the fluid, such as particles or objects, by exposure to UV light. The disclosed UV light generation systems may be flexible, allowing for their arrangement into enclosing configurations, such as configurations enclosing a fluid pathway. Optionally, the disclosed UV light generation systems may feature wrapped configurations. For example, a UV light generation sheet may be arranged in a helically wrapped configuration around a fluid path to allow for treatment of fluid in the fluid path by exposure to UV light. Alternatively, UV diffuse reflective layers may be wrapped helically with gaps between longitudinal sides to allow for UV-LEDs to be positioned at the gaps.

UV diffuse reflective or UV transmitting scattering layers of the UV light generation systems may advantageously allow the transmitted UV light to form an uniform UV light distribution, which may allow for more effective treatment and exposure to UV light, minimizing dim or unexposed areas in a treatment region. The UV diffuse reflective or UV transmitting scattering layers may only minimally absorb UV light, allowing for high UV intensities to be generated with dispersal of the light due to the diffuse reflective or scattering nature of the layers. The UV light generation system may also include photocatalysts, such as metal oxides photocatalysts including titanium dioxide, on the surface of the overlayer that is exposed to the fluid medium. The use of photocatalysts that generate reactive oxygen species upon absorbing UV light can be very effective in killing, destroying, or degrading pathogens.

Methods of making UV light generation systems include wrapping UV diffuse reflective layers around a mandrel such that a gap is present between adjacent, e.g., nearby, longitudinal sides of the UV diffuse reflective layer and positioning a flexible circuit adjacent to the UV diffuse reflective layer to align multiple UV-LEDs of a flexible circuit at the gap. A second UV diffuse reflective layer may be wrapped around the mandrel and first diffuse reflective layer, such as in an opposite rotation direction, with a second gap that overlaps the first gap at multiple locations corresponding to a plurality of openings. The method can further comprising positioning a flexible circuit including multiple UV-light emitting diodes (UV-LEDs) adjacent, e.g., adjoining, to the first or second UV diffuse reflective layer, wherein the positioning of the flexible circuit includes aligning the multiple UV-LEDs to correspond to the first gap or the openings when the second UV diffuse reflective layer is used. The UV-LEDs of the flexible circuit may be aligned at the openings to allow light generated by the UV-LEDs to pass through the openings. The first UV diffuse reflective layer may be wrapped around an overlayer, e.g., an overlayer comprising a photocatalysts, such as titanium dioxide (TiO$_2$).

In one embodiment, there is provided a method of making an ultraviolet (UV) light generation system, the method comprising wrapping a first UV diffuse reflective layer in a first direction around a mandrel with a first gap between adjacent, e.g., nearby, longitudinal sides of the first UV diffuse reflective layer, wherein the first UV diffuse reflective layer is flexible, and positioning a flexible circuit including multiple UV-light emitting diodes (UV-LEDs) adjacent, e.g. adjoining, to the first UV diffuse reflective layer, wherein the positioning of the flexible circuit includes aligning the multiple UV-LEDs to correspond to the first gap. The flexible circuit may be aligned with the multiple UV-LEDs to correspond to the first gap. Each of the multiple UV-LEDs is positioned to direct generated UV light through the first gap.

In another embodiment, there is provided a method of making an ultraviolet (UV) light generation system, the method comprising wrapping a first UV diffuse reflective layer in a first direction around a mandrel with a first gap between adjacent longitudinal sides of the first UV diffuse reflective layer, wherein the first UV diffuse reflective layer is flexible, wrapping a second UV diffuse reflective layer in a second direction around the mandrel and the first UV diffuse reflective layer with a second gap between adjacent longitudinal sides of the second UV diffuse reflective layer, wherein the second UV diffuse reflective layer is flexible, and wherein a portion of the first gap and a portion of the second gap overlap to generate a plurality of openings, positioning a flexible circuit including multiple UV-light emitting diodes (UV-LEDs) adjacent to the second UV diffuse reflective layer, wherein the positioning of the flexible circuit includes aligning the multiple UV-LEDs to correspond to the plurality openings. Each of the multiple UV-LEDs is positioned to direct generated UV light through the openings.

Other methods of making UV light generation system, such as a UV light generation sheet, are disclosed, Such methods may comprise generating a plurality of openings in a UV diffuse reflective layer and positioning a flexible circuit adjacent to the UV diffuse reflective layer such that multiple UV-LEDs of the flexible circuit are aligned at the openings.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 17A-17F provide schematic illustrations (front (1), side (2), and top (3)) detailing a method of making a UV light generation system in accordance with some embodiments.

DETAILED DESCRIPTION

Figure 1:
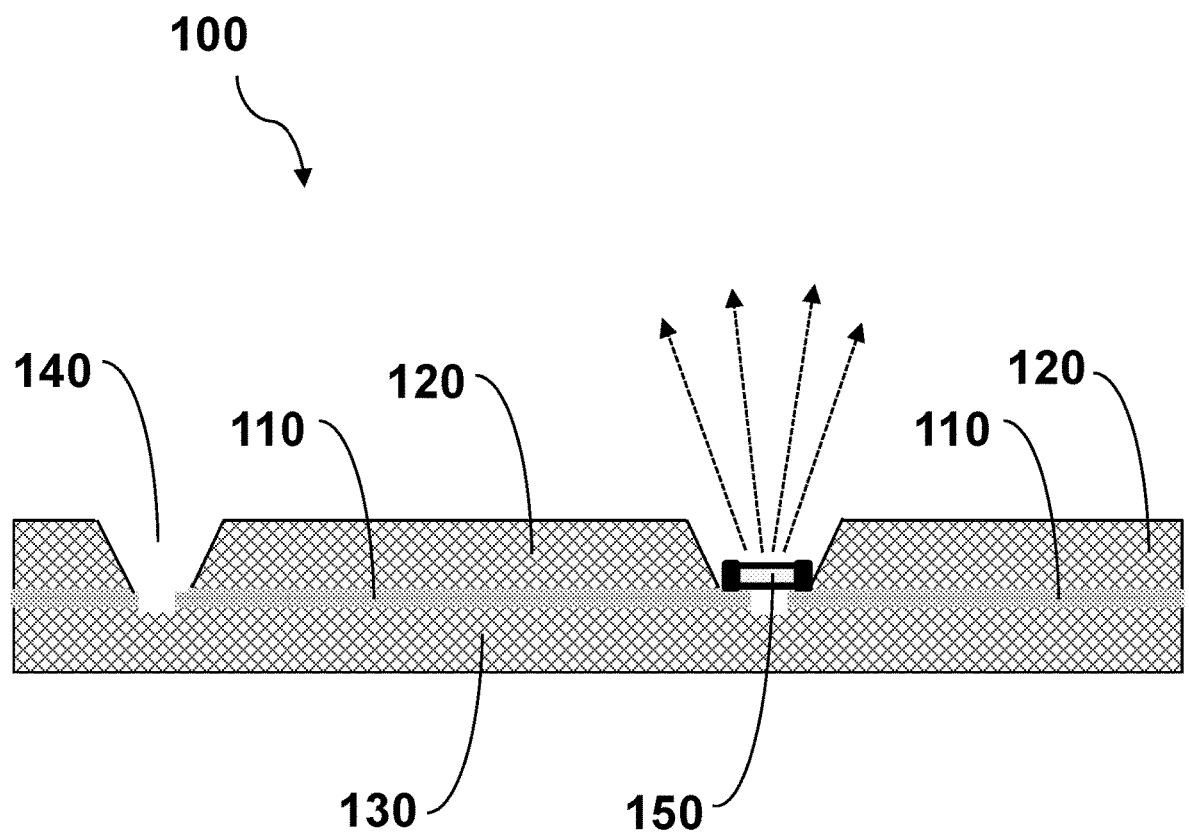
FIG. 1 provides a schematic illustration showing a cross-section of a flexible UV light generation sheet in accordance with some embodiments.

The present invention provides various embodiments of a flexible UV light generation system or assembly that includes a plurality of UV-LEDs arranged across a surface area of the flexible UV light generation sheet or assembly. It will be appreciated that the disclosed UV light generation systems are useful in disinfection, sterilization, purification, and other treatment applications. The disclosed flexible UV light generation sheets and assemblies are useful as part of or to construct a UV treatment systems or UV light generation systems. The arrangement on the surface area achieves a wide distribution, and in one embodiment an uniform distribution, of the UV emission field by transmissively scattering and/or diffusely reflecting the UV light. The inventors have found that a uniform distribution is more advantageous in disinfection, purification, and sterilization systems because void or dark areas are reduced or may be eliminated. For example, a dark area could allow an impurity or pathogen to pass through without being disinfected, purified, sterilized, or otherwise treated.

Example flexible UV light generation systems include those comprising a flexible circuit having multiple UV-LEDs. The flexible circuit may include a plurality of conductors, with each UV-LED positioned in independent electrical communication with at least one of the plurality of conductors. It will be appreciated that the multiple UV-LEDs may be arranged as an array and that the term array, as used herein, may correspond to a spatial distribution of a plurality of objects, such as UV-LEDs and conductors, with one or more of the objects connected to and/or attached to other objects in the array, such as by electrical connections. An array may be regular or non-regular, meaning the objects may be uniformly distributed or non-uniformly distributed. An example array may correspond to a ribbon cable, flexible circuit, or flat flexible cable having UV-LEDs attached along various positions of the ribbon cable, flexible circuit, or flat flexible cable.

The flexible circuit may be flexible and supported or otherwise attached to another flexible layer, such as a flexible UV diffuse reflective layer or a flexible UV transmissive scattering layer. In some embodiments that include a UV diffuse reflective layer, the UV diffuse reflective layer may include a plurality of openings, arranged to position each opening adjacent to a corresponding UV-LED, such that the corresponding UV-LED is exposed through the opening to allow UV light generated by the corresponding UV-LED to pass through the opening.

In one embodiment to achieve an uniform distribution, the UV light generation system is arranged to position at least a first UV-LED of the multiple UV-LEDs in a configuration that is directly opposed to a UV diffuse reflecting layer, such as a highly diffuse UV reflecting layer. In one embodiment to achieve an uniform distribution, the UV light generation system is arranged to position at least a first UV-LED of the multiple UV-LEDs in a configuration that is not directly opposed to any other of the multiple UV-LEDs. In one embodiment to achieve an uniform distribution, the UV light generation system includes a UV transmissive scattering layer or overlayer, such as a high haze film, to scatter or defocus UV light generated by the UV-LEDs. Optionally, these embodiments may be combined to provide advantageous positioning of UV-LEDs and inclusion of a UV transmissive scattering layer. In one embodiment, the UV transmissive scattering overlayer does not include UV absorbing filler material.

The stream being treated may be a gas or liquid stream that contains impurities such as pathogens, toxins, particulates, and combinations thereof. Treatment may be useful for reducing the impurities, or preferably eliminating the impurities, to produce a clean stream by disinfection, purifying, or sterilization. In one embodiment a liquid stream, such as water, blood, milk, or oil, is treated for use in sensitive applications that require high purity. In another embodiment, a gas stream is treated for use in sensitive applications that require high purity. In another embodiment, a gas stream comprising solid particles, such as food stuffs or seeds, is treated to disinfect, purify, or sterilize impurities. The gas stream may contain air or nitrogen and concentration of solid particles may vary from 0.1 to 99.9% in the gas stream. It should be understood that the impurities may be less than the solid particles.

A UV light generation sheet may have a width and a length that are of the same or similar dimensions in a generally rectangular configuration. A flexible UV light generation sheet may alternatively be constructed as a ribbon or tape, such as a rectangular configuration in which a width is considerably smaller than a length, such as where the length is 5 times greater (or more) than the width. Other sheet shapes are possible, such as circular, oval, and polygonal, as well as any other conceivable shape that may be constructed from a web of material.

A UV light generation sheet or system may optionally be flexible, allowing arrangement of the UV light generation sheet or system to define a fluid pathway, for example. To achieve flexibility, associated components of the UV light generation sheet or system may be flexible. As an example, a UV diffuse reflective layer, underlayer, or overlayer may optionally be flexible. As another example, a UV transmissive scattering layer, underlayer, or overlayer may optionally be flexible. In one embodiment, to define the fluid pathway the UV light generation sheet or system is wrapped, such as helically wrapped, laterally wrapped, or otherwise circumferentially arranged around the fluid pathway. The wrapped UV light generation sheet or system may form a tubular shape that corresponds to the fluid pathway. UV light generation sheet or system embodiments may be wrapped in a non-overlapping or overlapping configuration. In other embodiments, one or more UV light generation sheets or systems may be helically wrapped to define a fluid pathway. Any desirable configuration may be used herein, such as a planar configuration, a convex configuration, a concave configuration, and combinations of these.

Materials in UV light generation sheets and systems may individually and/or collectively have elastic, compressive, or bending moduli suitable for the overall structure to be flexible. Example elastic, compressive, or bending moduli for flexible assemblies and materials exhibit an elastic modulus of between 0.001 GPa and 3.0 GPa. In some embodiments, materials included in a UV light generation sheet or system may exhibit an elastic, compressive, or bending modulus outside of this range. For example, conductors used for providing current and/or voltage to one or more UV LEDs may have a relatively larger elastic modulus, but may still exhibit flexibility along one or more axes, such as by way of a suitable bending modulus or compressive modulus, sufficient for inclusion in a flexible assembly. In general, the term flexible refers to materials that elastically bend in response to a force rather than fracture or undergo inelastic deformation, and the term flexible may be used interchangeably herein with the terms pliable and bendable. In some embodiments, flexible materials may be bent to a radius of curvature of 1 cm or less (e.g., 1 mm to 1 cm) without undergoing fracture or inelastic deformation. Various ASTM and ISO standards are useful for determining or specifying flexibility features of different materials including ASTM standards D747, D790, D5045, D7264, E111, E1290, E1820, and E2769 and ISO standards 170, 178, 12135, and 12737, which are hereby incorporated by reference.

Example configurations include a tube-like configuration, where the flexible UV light generation sheet or system is arranged to enclose an interior space, such as by wrapping the flexible UV light generation sheet or system around a hollow or solid tube or other cylindrical structure, such as a mandrel. Depending on the configuration, UV light generated by the UV-LEDs may be directed into the interior space or opposite to the interior space. Other configurations useful with some embodiments, include pouch-like configurations where two portions or sections of a flexible UV light generation sheet or system are placed adjacent to one another such that material or fluid may be inserted between the two portions or sections. In some embodiments, one or more flexible UV light generation sheets or systems may be arranged as a liner of a vessel or container and used to generate UV light within the interior space of the vessel or container.

It will be appreciated that the flexible UV light generation sheet or system does not need to completely enclose an interior space. For example, in some embodiments, the vanes in a static mixer or one outer wall may be covered with a flexible UV light generation sheet or system. In another embodiment, the enclosed space may not be defined. For example, a flexible UV light generation sheet or system could be mounted one end with the opposite end free to move in a fluid stream, similar to a flag. The flag configuration may use or correspond to a flexible UV light generation sheet that has UV-LEDs mounted on one side or both sides.

FIG. 1 provides a schematic cross-sectional side-view illustration of a flexible UV light generation sheet 100 in accordance with some embodiments. A UV-LED 150 is electrically connected to individual segments of conductor 110 to allow current to be applied for UV light generation. Below conductor 110 is a support layer 130 and above conductor 110 is a UV diffuse reflective layer 120. Support layer 130 may optionally be one or more UV diffuse reflective layers. UV diffuse reflective layer 120 is positioned so light from UV-LED 150 can be emitted out of flexible UV light generation sheet 100. Support layer 130 is positioned below UV-LED 150 and may also be UV reflective such that stray light is reflected back. Openings 140 may be included in UV diffuse reflective adjacent layer 120 to allow light from the UV-LED 150 to be emitted there through. The openings 140 may have a variety of shapes including circles, ovals, triangles, squares, rectangles, diamonds, and other similar shapes. The size of the opening may also vary but is sufficient to allow light from a UV-LED 150 to pass through and may have an opening size from 0.5 to 20 mm, e.g. from 2 to 10 mm, or from 3 to 6 mm. In one embodiment, the openings 140 may be formed by gaps created between adjacent longitudinal sides of one or more UV diffuse reflective layers that are wrapped to form the sheet. Optionally, conductor 110 may be segmented, such as at openings 140, to allow different contacts of electrical components to be attached to the individual segments.

As illustrated, a lens or focusing element is not positioned above UV-LED 150. When no lens or focusing element is used, the configuration advantageously permits UV light intensity to spread over a wider area and achieve a more uniform distribution of UV light intensity over a wider area, minimizing dim regions that may occur when lensing or focusing elements are included.

Figure 2A:
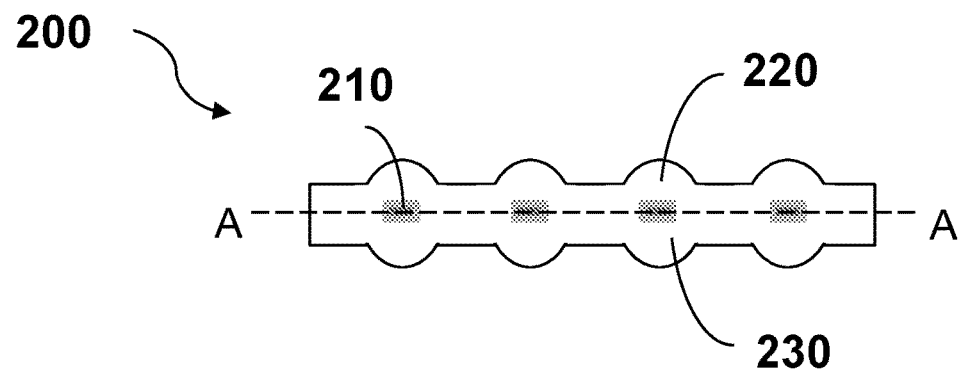
FIG. 2A and FIG. 2B provide schematic illustrations showing cross-section side and overhead views of flexible UV light generation sheets in accordance with some embodiments.
Figure 2B:
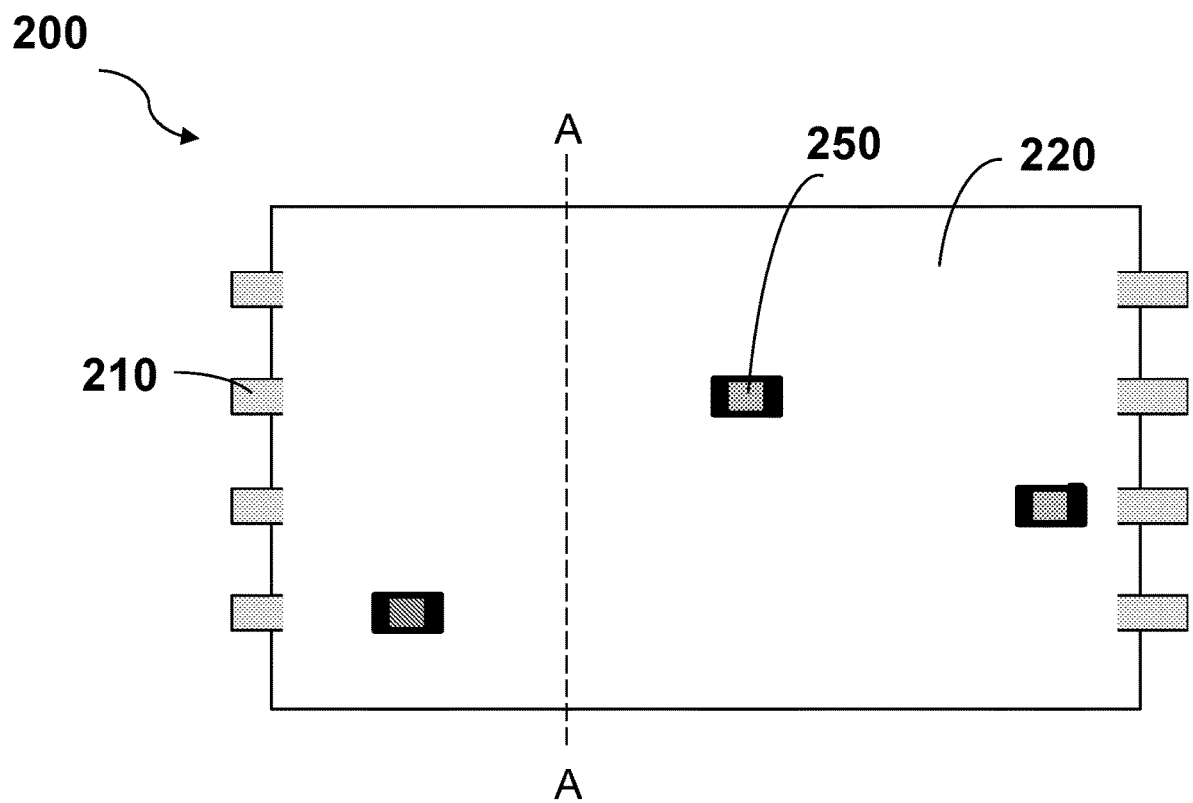

FIG. 2A provides a schematic cross-sectional end-view illustration and FIG. 2B provides a cross-sectional top-view illustration of a flexible UV light generation sheet 200 in accordance with some embodiments. FIG. 2A shows a flexible UV light generation sheet 200 in which conductors 210 are optionally included in a ribbon or a flexible flat cable and may be joined or attached to one another by way of electrically insulating material surrounding at least a portion of one or more conductors. UV diffuse reflective layer 220 may be positioned above conductors 210, such that UV diffuse reflective layer 220 covers at least a portion of conductors 210 and/or any insulating material surrounding the conductors. It will be appreciated that UV diffuse reflective layer 220 may be in individual sections positioned above each conductor 210 or may a continuous layer positioned above any number of conductors 210. Support layer 230 may be positioned below the conductors 210, and below UV-LEDs 250, such that support layer 230 covers at least a portion of the conductors 210 and UV-LEDs 250 and/or any insulating material surrounding the conductors and UV-LEDs. Optionally, support layer 230 is a UV diffuse reflective layer. It will be appreciated that support layer 230 may be in individual sections positioned below each conductor 210 or may a continuous layer positioned below any number of conductors 210 and UV-LEDs 250. It will be appreciated that a support layer may be an optional feature of the flexible UV light generation sheets described herein, as the structure of the UV-LEDs, conductors, a UV transparent scattering or UV diffuse reflective layer, and any additional layers, such as overlayers, may provide sufficient structure to the flexible UV light generation sheet such that a separate support layer is not needed. Optionally, UV diffuse reflective layer 220 or support layer 230 may be provided as a jacketing material of conductors 210.

FIG. 2B may correspond to a perpendicular view from those shown in FIG. 1 and FIG. 2A. In flexible UV light generation sheet 200, conductors 210 are included and shown extending from edges of flexible UV light generation sheet 200. Conductors 210 are at least partially covered by a UV diffuse reflective layer 220. UV-LEDs 250 are illustrated as positioned above several conductors 210, with an additional conductor 210 used as a common or current return line. Similar to FIG. 1, UV-LEDs 250 may be positioned at openings in UV diffuse reflective layer 220 and bridging segments of conductors 210. It will be appreciated that, as illustrated in FIG. 2B, UV-LEDs 250 may be individually electrically addressable. Allowing the UV-LEDs to be individually electrically addressable may provide good control to adjust the UV light within the fluid pathway to achieve an uniform UV emission. It will be appreciated that FIGS. 2A and 2B provide an array of multiple UV-LEDs 250 with a plurality of conductors 210, such as a non-regular array.

Figure 3A:
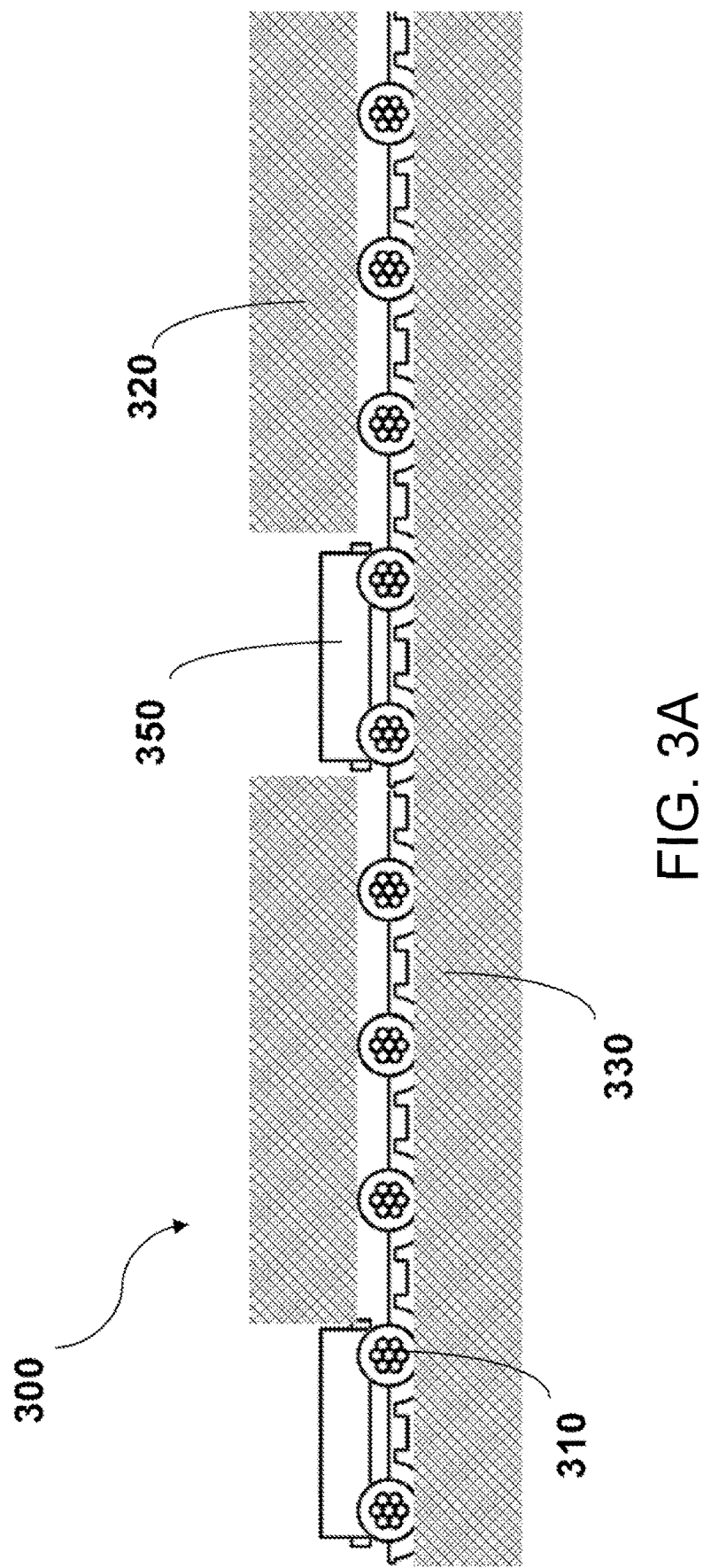
FIG. 3A and FIG. 3B provide schematic illustrations showing cross-sections of flexible UV light generation sheets in accordance with some embodiments.
Figure 3B:
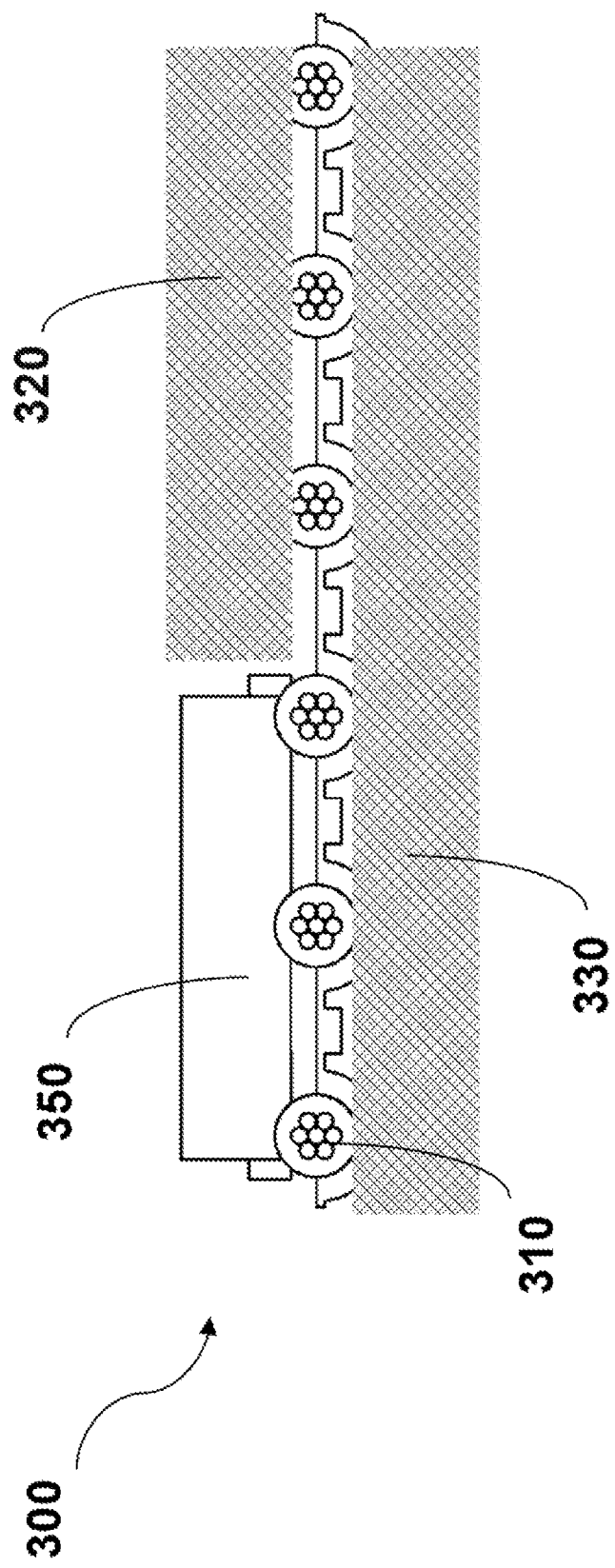

As an alternative to driving LEDs in series with a common current, LEDs may be driven in parallel with a common voltage. FIG. 3A provides a cross-sectional schematic illustration of a flexible UV light generation sheet 300 including a ribbon cable. The ribbon cable includes a plurality of round conductors 310, each depicted as a stranded core cable. It will be appreciated that solid core conductors are also useful. A UV-LED 350 is depicted as positioned adjacent to and in electrical communication with two different conductors, in contrast to the configuration illustrated in FIGS. 1, 2A, and 2B, where a UV-LED is positioned to bridge segments of a single conductor. FIG. 3B provides a cross-sectional schematic illustration of a flexible UV light generation sheet 300 where one conductor, for example the center conductor, may be used as a heat sink, for example, to allow heat generated by one or more UV-LEDs to flow away from the UV-LEDs.

Figure 4:
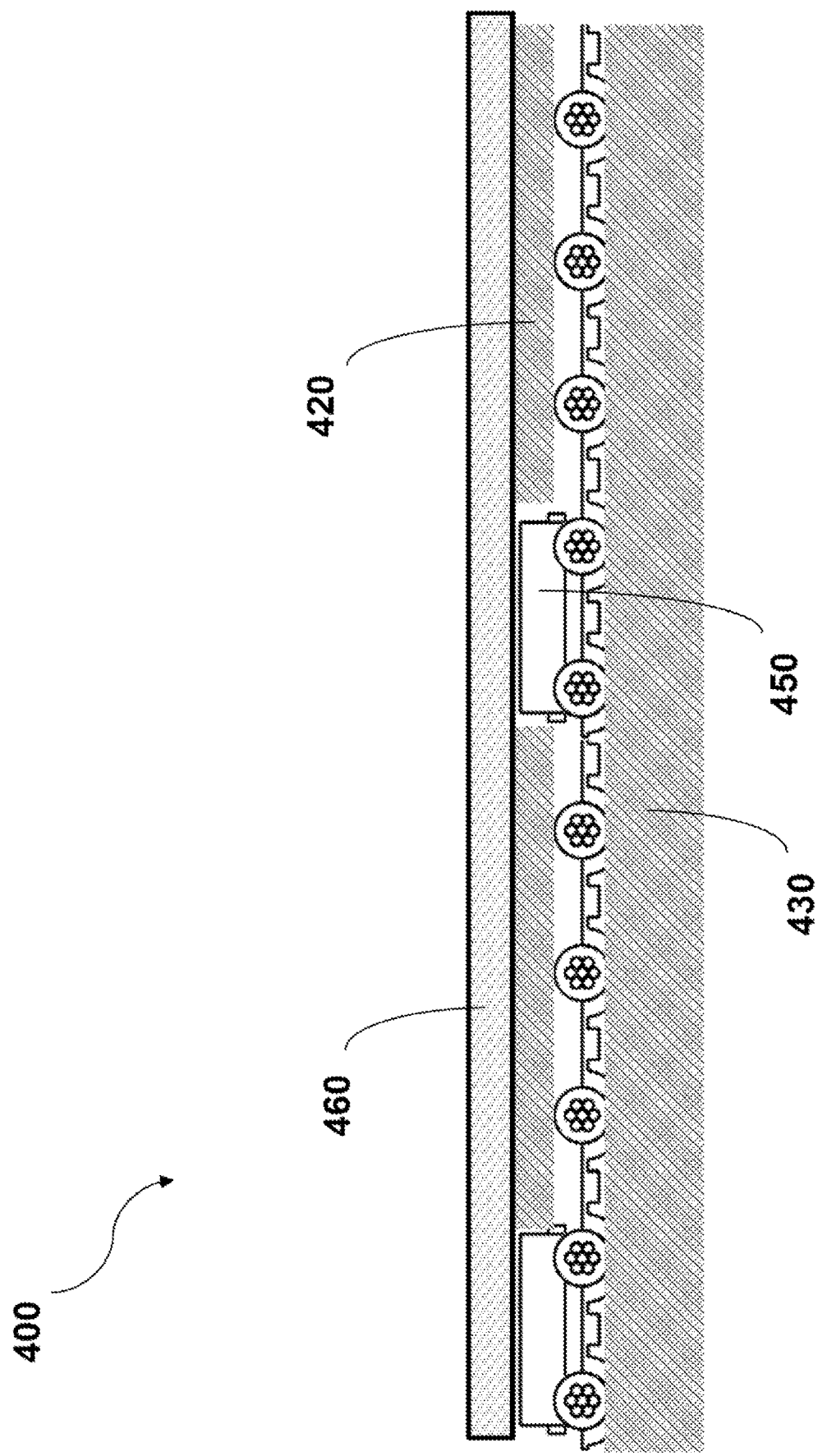
FIG. 4 provides a schematic illustration showing a cross-section of a flexible UV light generation sheet in accordance with some embodiments.

FIG. 4 provides a cross-sectional schematic illustration of a flexible UV light generation sheet 400 including a ribbon cable with a plurality of conductors 410, UV-LEDs 450 and adjacent layer 420. An additional overlayer 460 is depicted as positioned above UV diffuse reflective layer 420 and above UV-LEDs 450. Overlayer 460 is a UV transparent layer, allowing UV light generated by UV-LEDs 450 to transmit out from flexible UV light generation sheet 400. In addition, incident UV light may transmit through overlayer 460 and be reflected by adjacent layer 420 back through overlayer 460 and into the medium above the flexible UV light generating sheet 400. Optionally, additional overlayer 460 may be a UV transmissive scattering layer, allowing UV light generated by UV-LEDs 450 to transmit out from flexible UV light generation sheet 400 and be scattered to more uniformly distribute the light. A UV transmissive scattering layer, also referred to as a UV haze layer or UV transmissive scattering layer, diffuses light over a wide range of angles. ASTM standard D1003, hereby incorporated by reference, describes details of haze and transparency measurements, and defines haze as the ratio of diffuse transmittance to total luminous transmittance, which may correspond to the percentage of light passing through a layer that deviates from the incident beam greater than 2.5 degrees on average. Optionally, overlayer 460 may correspond to an encapsulating layer, which may provide water resistance or other environmental protection to underlying components. Advantageous properties of an overlayer may include electrically insulation, low water and oxygen transmission rates, high mechanical toughness, and high thermal conductivity.

Optionally a UV diffuse reflective underlayer 430 is positioned below the UV-LEDs to redirect any backward scattered light in the forward direction above the UV-LEDs. In this embodiment, little if any light is lost and less power is required to disinfect the fluid stream.

Figure 5:
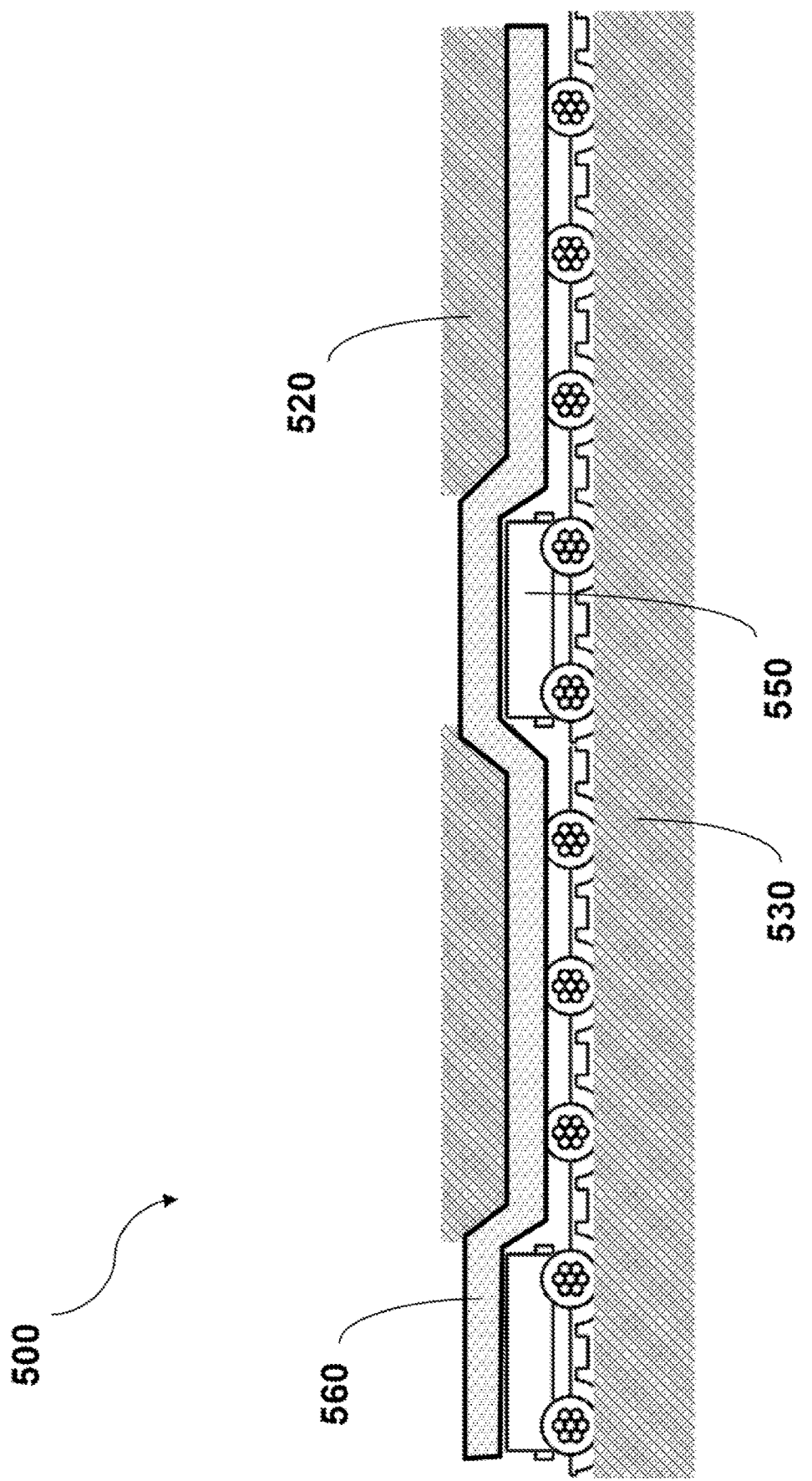
FIG. 5 provides a schematic illustration showing a cross-section of a flexible UV light generation sheet in accordance with some embodiments.
Figure 6:
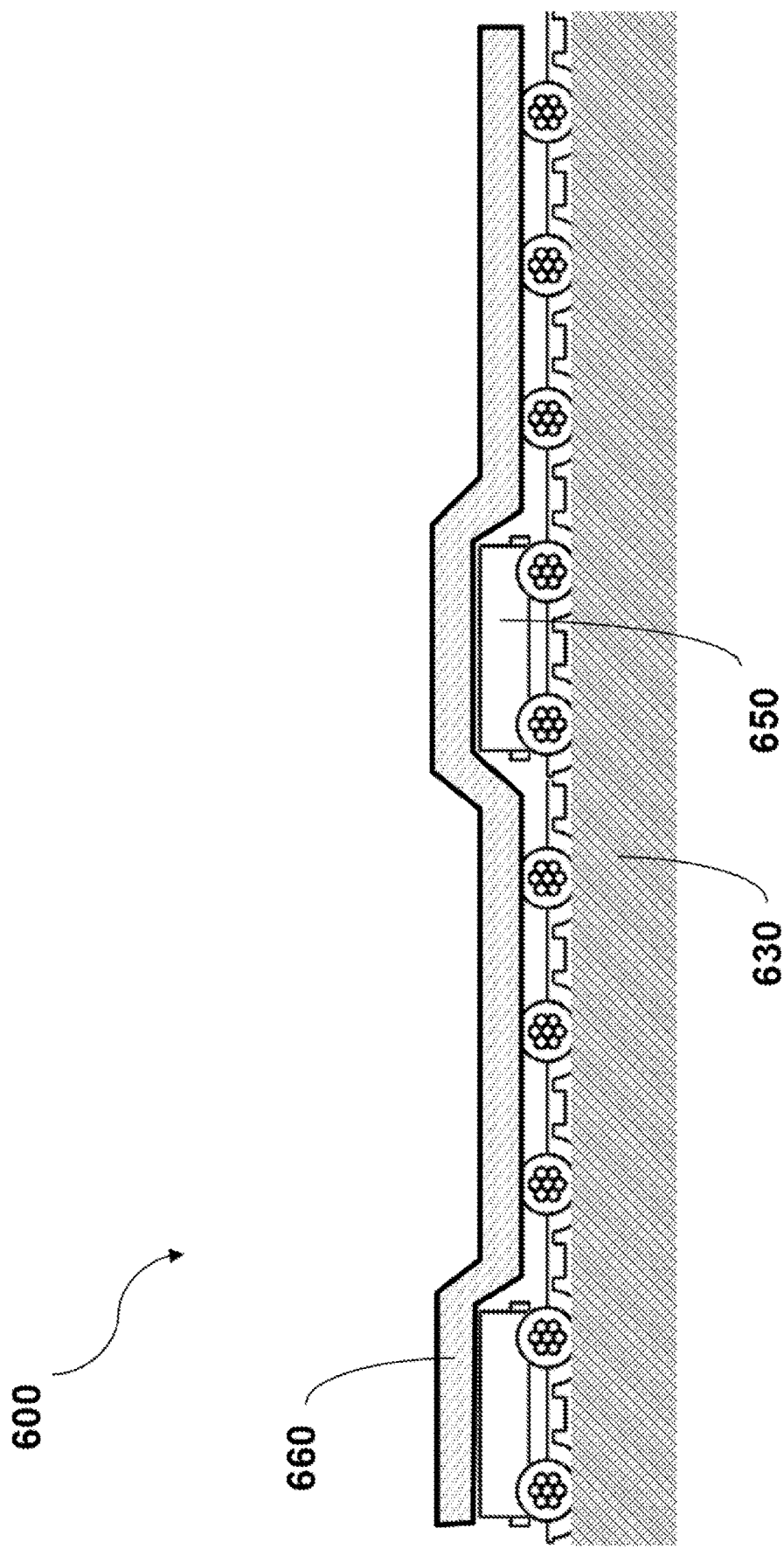
FIG. 6 provides a schematic illustration showing a cross-section of a flexible UV light generation sheet in accordance with some embodiments.

FIG. 5 provides an alternative embodiment of a flexible UV light generation sheet 500 including a ribbon cable with a plurality of conductors 510 and UV-LEDs 550. FIG. 5 is similar to FIG. 4 except that the overlayer 560 is below adjacent reflector layer 520. FIG. 6 provides a further alternative embodiment of a flexible UV light generation sheet similar to FIG. 4 and FIG. 5 except that the adjacent reflective layer 520 has been removed. In this embodiment, incident light would transmit through the overlayer 660 and be reflected by underlayer 630.

Figure 7A:
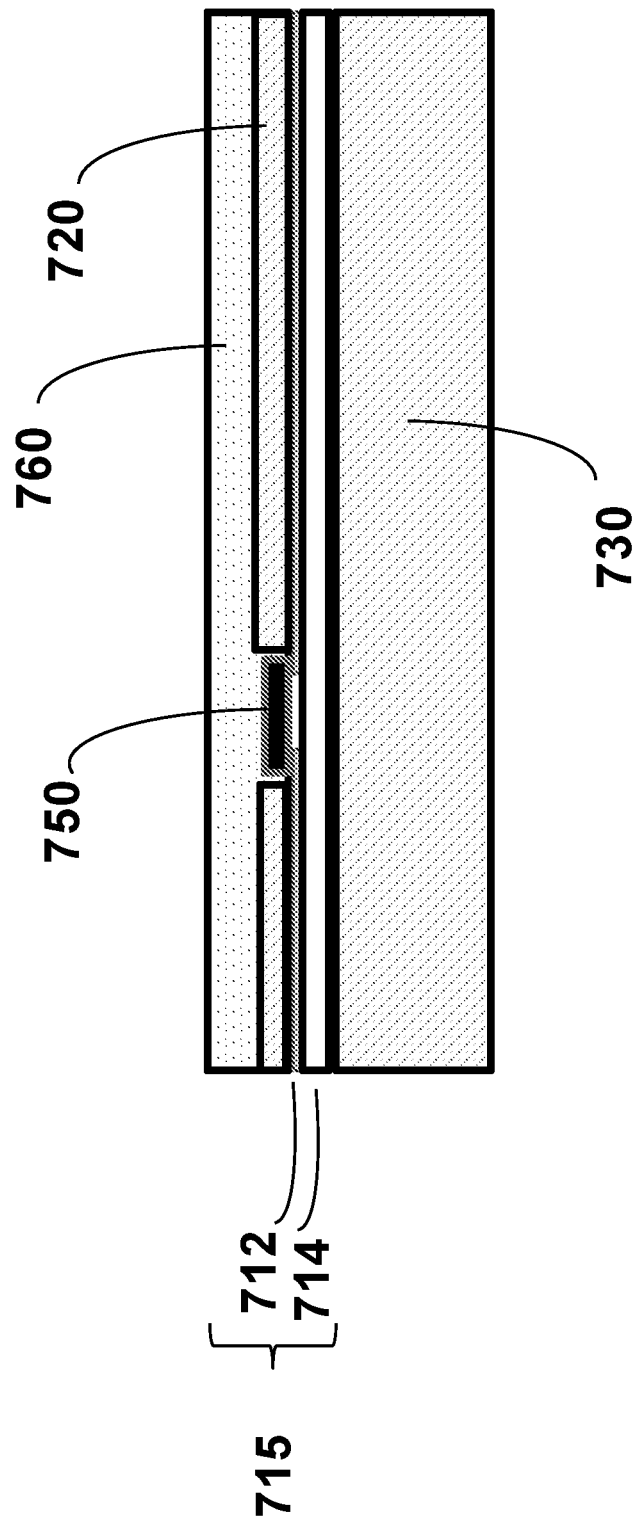
FIG. 7A and FIG. 7B provide schematic illustrations showing cross-sections of flexible UV light generation sheets in accordance with some embodiments.

In some embodiments, a flexible UV light generation sheet makes use of a flexible circuit rather than a ribbon or flat flexible cable for providing electrical connections to one or more UV-LEDs. For example, FIG. 7A provides a schematic cross-sectional illustration of a flexible circuit-based UV light generation sheet 700. Here, flexible UV light generation sheet 700 includes flexible circuit 715, which corresponds, for example to a flexible conductive trace 712 supported on a flexible substrate film 714. As an example, flexible conductive trace 712 may correspond to a thin copper layer and flexible film 714 may correspond to a polymer film, such as polyimide. UV-LEDs 750 may be positioned in electrical communication with portions of flexible conductive trace 712 and supported by flexible film 714. An overlayer 760, such as a UV transparent layer or a UV transmissive scattering layer, may be included, depending on the particular configuration. The overlayer 760 may protect the UV-LEDs from the environment including, for example, immersion in water. Advantageous properties may include electrically insulation, low water and oxygen transmission rates, high mechanical toughness, and high thermal conductivity. A reflective underlayer 730, and a reflective layer 720, may be included, depending on the particular configuration.

Figure 7B:
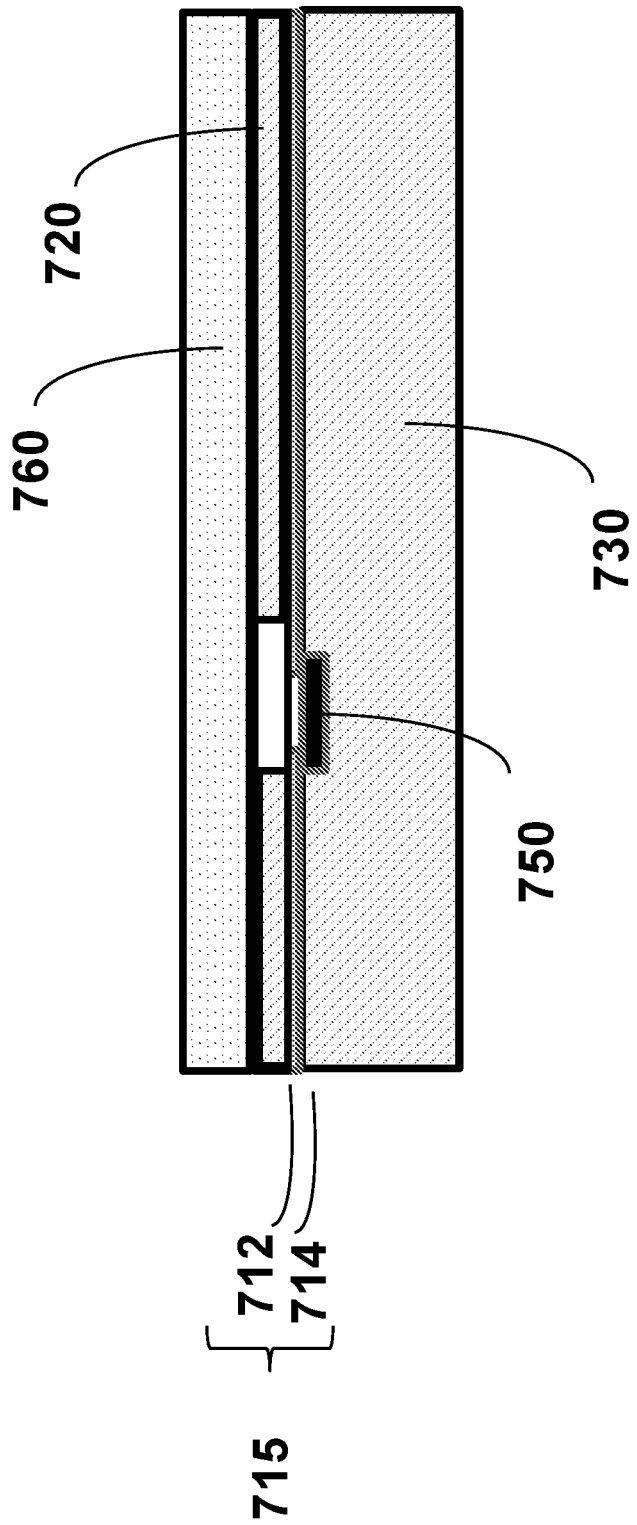

Another embodiment depicting a flexible UV light generation sheet 700 using a flexible circuit rather than a ribbon or flat flexible cable is shown in FIG. 7B. Here, flexible UV light generation sheet 700 includes flexible circuit 715, which corresponds, for example to a flexible conductive trace 712 supported on a flexible film 714. As an example, flexible conductive trace 712 may correspond to a thin copper layer and flexible film 714 may correspond to a polymer film, such as polyimide. UV-LEDs 750 may be positioned in electrical communication with portions of flexible conductive trace 712 and supported by flexible film 714. Openings may be included in in flexible film 714, to allow UV light generated by UV-LEDs 750 to be transmitted away from flexible UV light generation sheet 700. Alternatively, flexible film 714 may be transparent to the emitted light from UV-LEDs so openings are not required. A reflective underlayer 730, and a reflective layer 720, may be included, depending on the particular configuration.

UV Light Generation Assembly Configurations

Figure 8A:
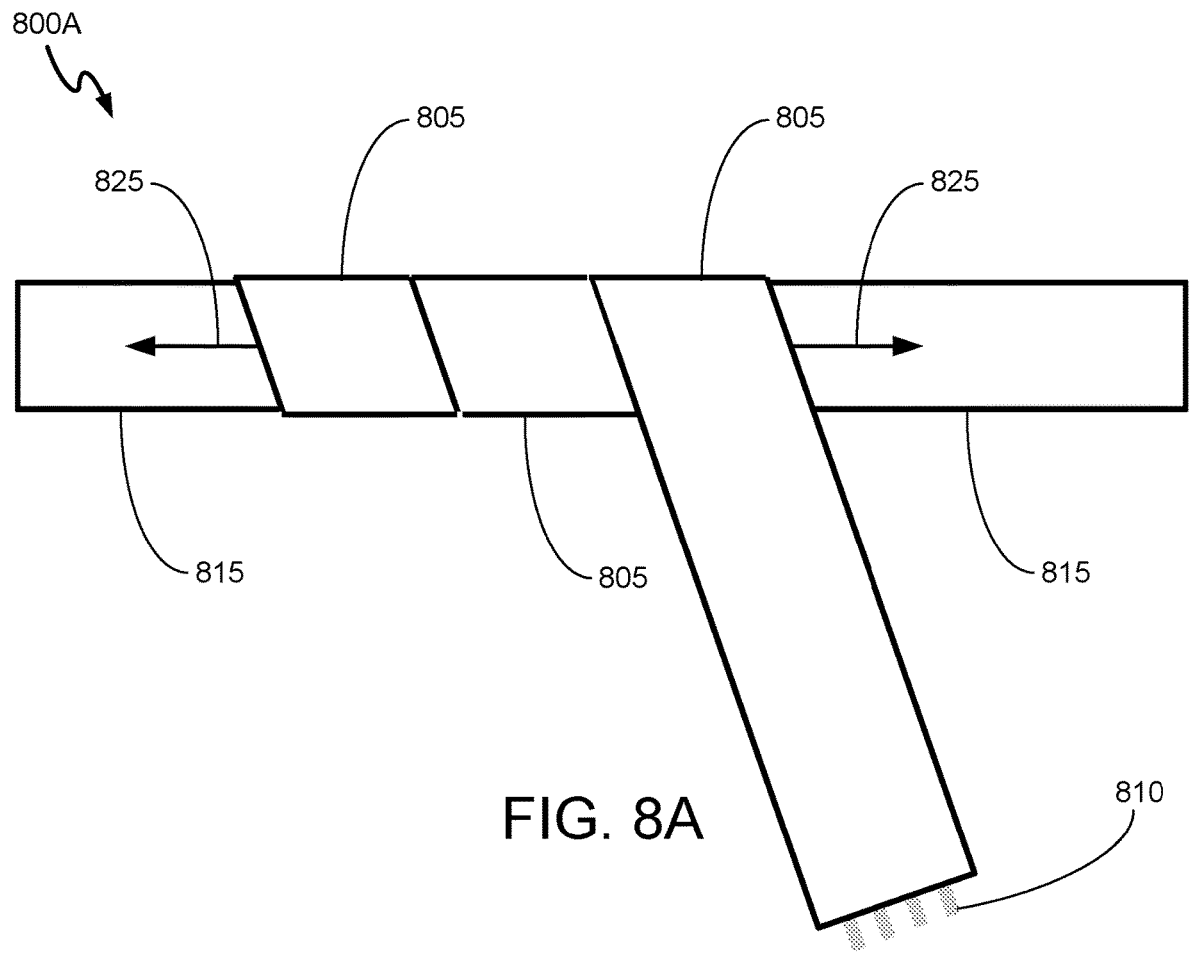
FIG. 8A and FIG. 8B provides a schematic illustration showing a flexible UV light generation sheet arranged in a helical wrapped configuration in accordance with some embodiments.

A variety of UV light generation systems using the flexible UV light generation sheets described herein are contemplated. As an example, FIG. 8A depicts a UV light generation system 800A including a flexible UV light generation sheet 805 wrapped in a helical configuration around a tubular structure 815. In one embodiment, the UV light generation sheet 805 has opposing longitudinal sides that are adjacent or partially overlap. The tubular shape may correspond to the fluid path 825. In this way, flexible UV light generation sheet may be arranged to enclose a fluid path 825, corresponding to an interior region of tubular structure 815, for example. The fluid path 825 may be useful for flowing liquids or gases through a region illuminated by UV light for disinfecting or purifying the liquids or gases. Optionally, particles or objects may be suspended in the fluid and exposed to the UV light for disinfecting or purifying the particles or objects. Optionally, flexible UV light generation sheet 805 and tubular structure 815 are flexible, allowing treatment system 800A to adopt a bent or curved configuration. Optionally, tubular structure 815 is a mandrel used to form a tubular shape when the flexible UV light generation sheet is wrapped. In this embodiment, the mandrel is removed to form a fluid pathway. In embodiments, tubular structure 815 is a UV transparent tube, permitting UV light generated by UV-LEDs of flexible UV light generation sheet 805 to transmit into an interior of tubular structure 815. In this embodiment, the UV transparent tube may be considered part of the UV light generation system. In one embodiment, UV-LEDs of flexible UV light generation sheet 805 are arranged to position at least a first UV-LED in a configuration that is not directly opposed, across the fluid path 825, to any other UV-LED. Incidentally, UV-LEDs of flexible UV light generation sheet 805 are arranged to position at least a first UV-LED in a configuration that is directly opposed, across the fluid path 825, to a UV diffuse reflective layer of flexible UV light generation sheet 805. This allows the UV light to reflect and become more uniformly distributed in the fluid pathway. In FIG. 8A, conductors 810 are also illustrated as extending from flexible UV light generation sheet 805 and may be connected to circuits or power sources. It will be appreciated that for direction of UV light into fluid path 825, UV-LEDs will be positioned facing tubular structure 815. UV-LEDs are on the side of the sheet facing the interior and are not visible from the exterior as shown in FIG. 8A.

Figure 8B:
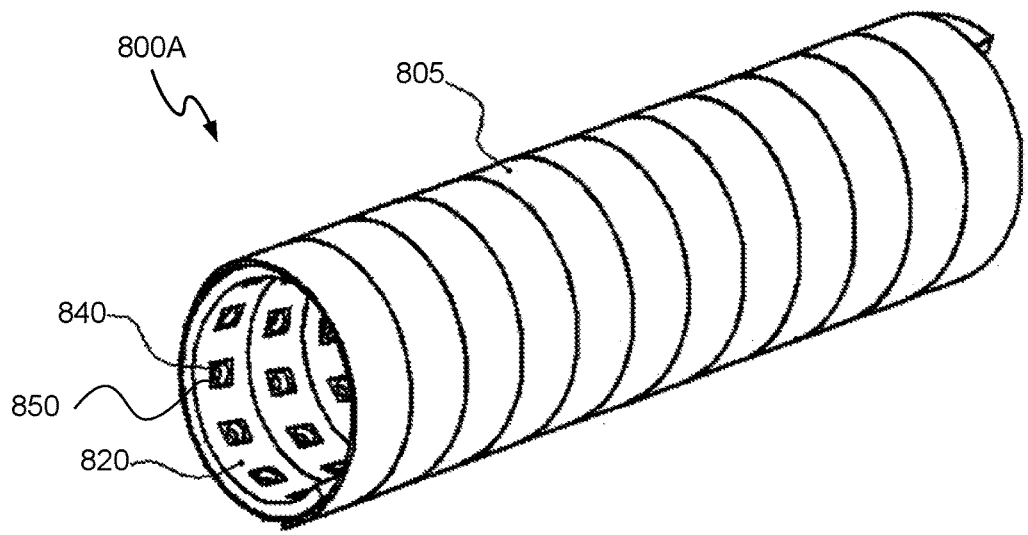

FIG. 8B is a perspective view to show the interior region of the UV light generation sheet 805. For purposes of illustration the tubular structure 815 is not shown in FIG. 8B. The UV light generation sheet 805 has openings 840 that align with UV-LEDs 850 on the conductors (not shown in FIG. 8B). The UV light generation sheet 805 may be constructed of a diffuse UV reflective layer 820. It will be appreciated that additional overlayers or underlayers may optionally be included in UV light generation sheet 805, e.g., such as a reinforcing underlayer, a UV transparent overlayer, and/or a UV transmissive scattering overlayer. In one embodiment, the UV transparent overlayer has a UV transmission of at least 80% at 250 nm. As shown in FIGS. 8A and 8B, the sheet 805 is wrapped closely together and may partially overlap to prevent a gap between the adjacent longitudinal sides.

Optionally, a surface at the fluid pathway may be coated with or treated with $TiO_2$ or another UV active photocatalytic material. Other photocatalytic materials include metal oxides such as $SiO_2$, $ZnO$, $Bi_2WO_6$, $Bi_2OTi_2O$, $Fe_2O_3$, $Nb_2O_5$, $BiTiO_3$, $SrTiO_3$, or $ZnWO_4$, and other metal catalysts such as $CuS$, $ZnS$, $WO_3$, or $Ag_2CO_3$. Upon exposing $TiO_2$ or another light active photocatalytic material UV light generated by LEDs, electrons and holes may be generated to allow oxidation and/or reduction of material coming into contact with the $TiO_2$ or active photocatalytic material. For example, contacting a light activated photocatalyst with water or oxygen may result in generation of reactive oxygen species, such as hydroxyl radicals (OH) and superoxide ($O_2^-$). These reactive oxygen species may be useful for degrading or destroying pathogens, toxins, or impurities.

Figure 8C:
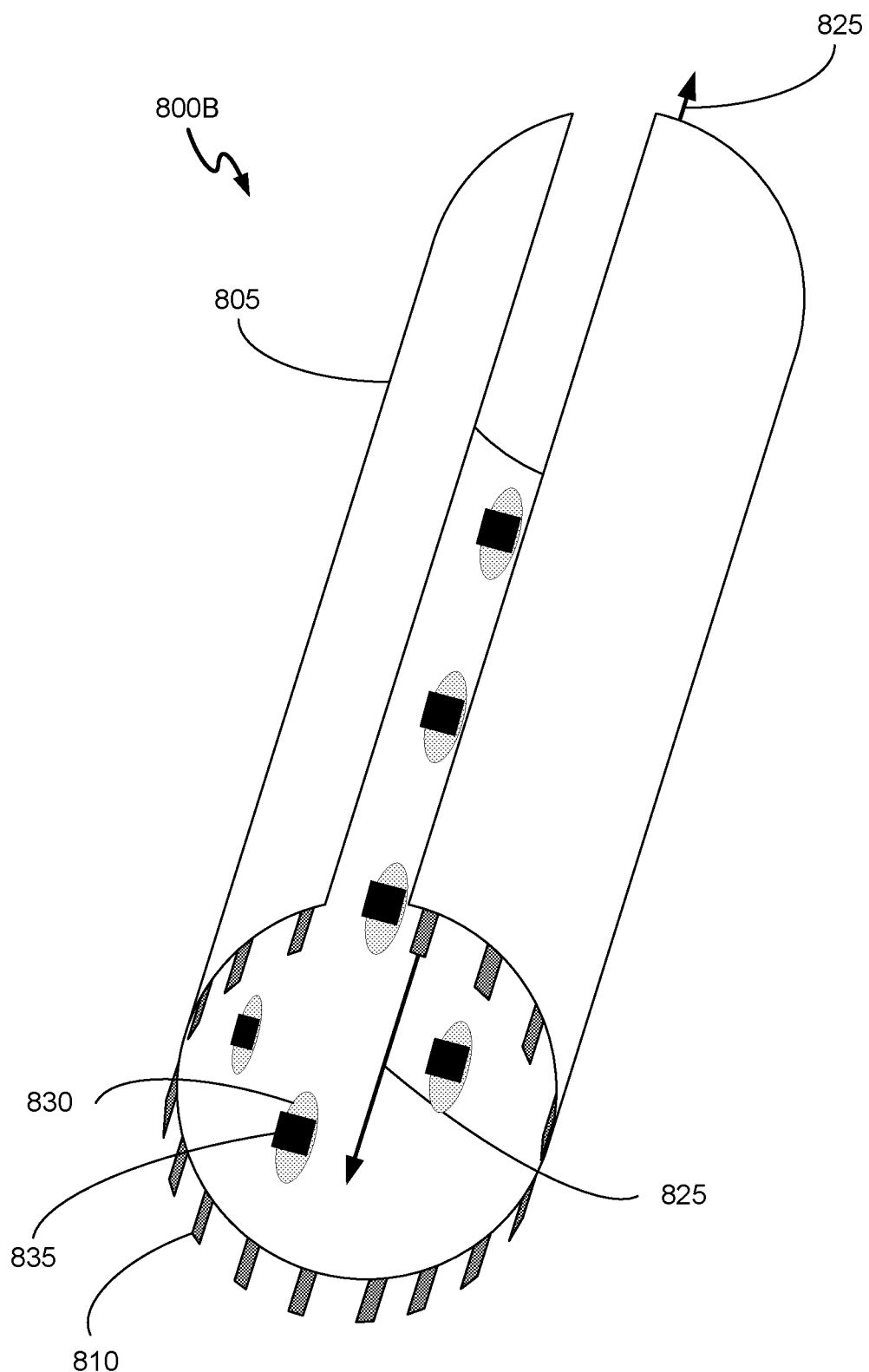
FIG. 8C provides a schematic illustration showing a flexible UV light generation sheet arranged in a longitudinal wrapped configuration in accordance with some embodiments.

An alternative arrangement of a UV light generation treatment system 800B including flexible UV light generation sheet 805 is depicted in FIG. 8C, where instead of being helically wrapped around the fluid path 825, the flexible UV light generation sheet 805 is longitudinally wrapped around the fluid path 825. It will be appreciated that in the illustration depicted in FIG. 8C the longitudinal wrap around fluid path 825 is shown as incomplete for purposes of illustration. In practice, ends of flexible UV light generation sheet 805 may optionally be attached and/or joined to form a complete enclosed fluid path 825. This prevents a gap between the sides of the sheet 805 in FIG. 8C. In FIG. 8C, conductors 810 are also illustrated as extending from flexible UV light generation sheet 805. There are various openings 840 in the UV light generation sheet 805 that are positioned to align with the UV-LEDs 850 connected to the conductors 810. It will be appreciated that additional overlayers or underlayers may optionally be included in UV light generation sheet 805, e.g., such as a reinforcing underlayer, a UV transparent overlayer, and/or a UV transmissive scattering overlayer. In addition, the UV light generation sheet 805 shown in FIG. 8C may be wrapped around a transparent tube.

Figure 9A:
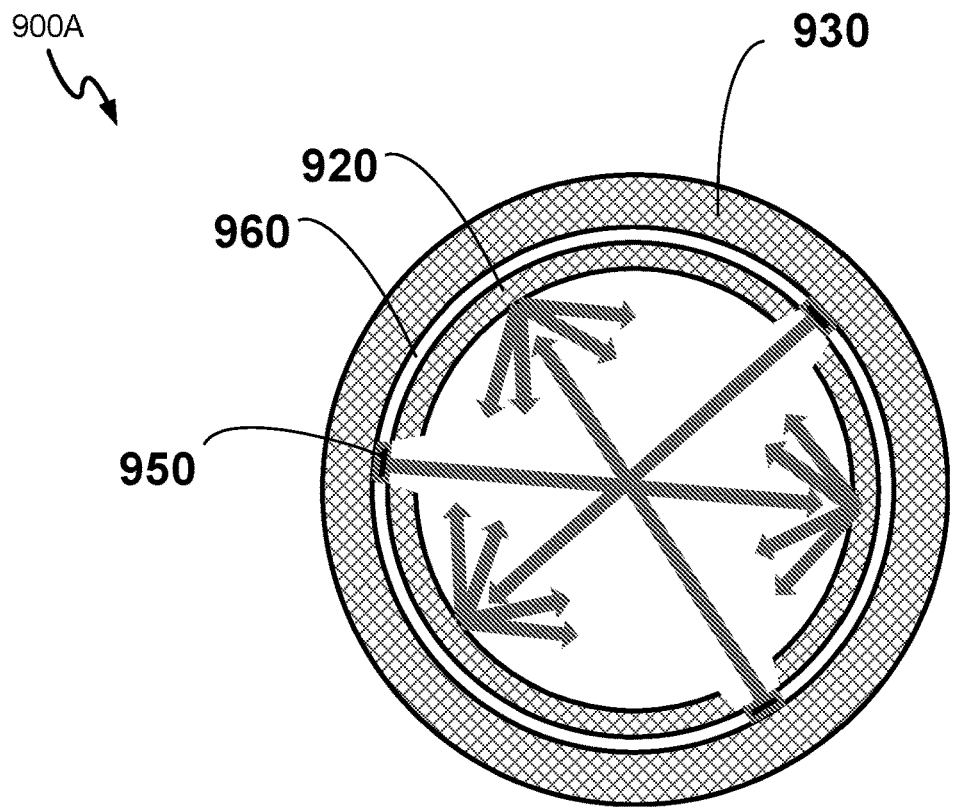
FIG. 9A and FIG. 9B provide a schematic illustrations showing cross-sectional views of UV treatment systems in accordance with some embodiments.
Figure 9B:
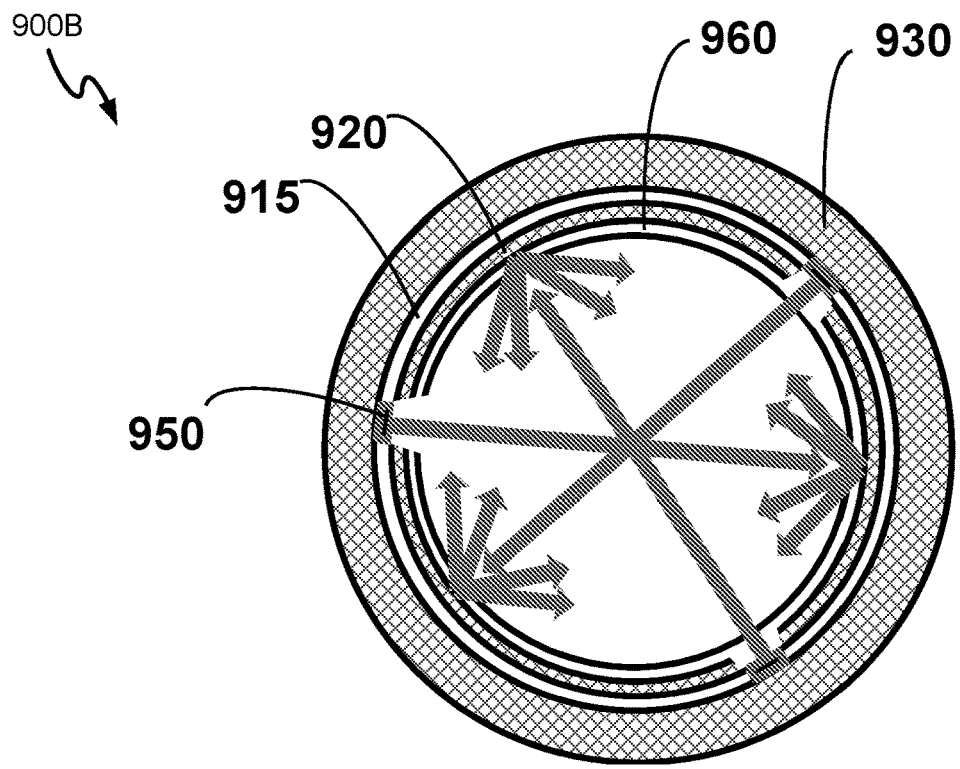

FIGS. 9A and 9B depict schematic cross-sectionals illustration of UV light generation systems 900A and 900B, such as using the flexible UV light generation sheet depicted in FIG. 5, including UV diffuse reflective layer 920, underlayer 930, UV-LEDs 950, flex circuit 915 and overlayer 960, which may be positioned in various adjacencies, depending on the configuration. It will be appreciated that FIGS. 9A and 9B may represent a cross-sectional views of treatment system 800 of FIGS. 8A and 8B, for example. Light generated by UV-LEDs 950 is directed into a fluid path defined as an interior space surrounded by the flexible UV light generation sheet. When UV light reaches the UV diffuse reflective layer 920, the UV light is reflected back into the fluid path, allowing for high levels of UV light intensity to be generated in the fluid path. In embodiments, reflective layer 920 is a highly diffuse reflective material, such as a material that reflects 98% or more of incident UV light, such as UV light having wavelengths between 100 nm and 400 nm, or any subrange thereof. As illustrated, each UV-LED 950 is positioned in a configuration that is not directly opposed to any other UV-LED 950. Stated another way, each UV-LED 950 is positioned in a configuration that is directly opposed to reflective layer 920 to allow UV light to reflect off reflective layer 920 and become more uniformly distributed. It will be appreciated that, in the configuration illustrated in FIGS. 9A-9B, the flexible UV light generation sheet may not include openings in a UV diffuse reflective layer. Overlayer 960 is UV transparent and optionally UV scattering (e.g., hazy) or comprises photocatalysts on the surface. Overlayer 960 may optionally provide for protection of underlying or adjacent layers, and may, for example, provide protection against penetration by water or another fluid.

Figure 10:
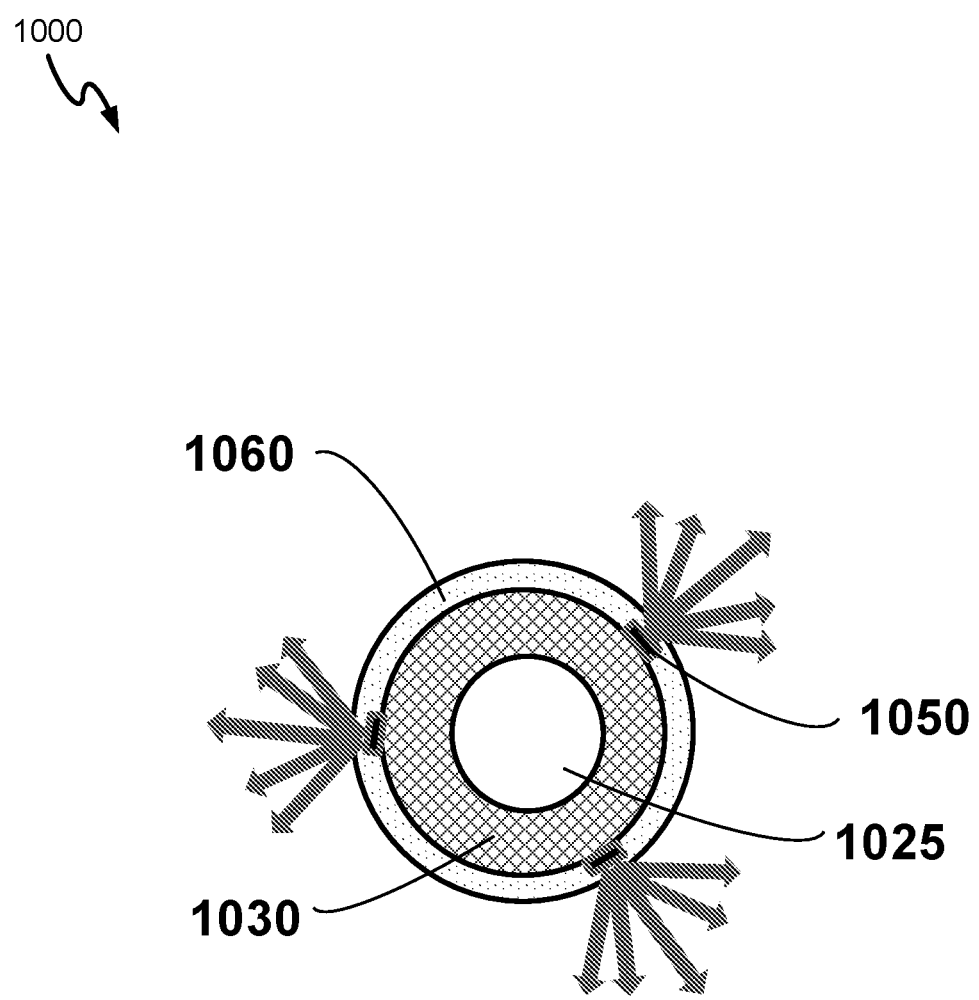
FIG. 10 provides a schematic illustration showing a cross-sectional view of a UV treatment system in accordance with some embodiments.

FIG. 10 depicts a schematic cross-sectional illustration of a light generation treatment system 1000. Such a configuration may be constructed similar to the system 800 illustrated in FIGS. 8A and 8B, where a flexible UV light generation sheet is helically wrapped around a tubular structure or where a flexible UV light generation sheet is longitudinally wrapped around a tubular structure. However, for light generation treatment system 1000, the structure of the flexible UV light generation sheet is reversed from the other embodiments. This enables the generation of an uniform UV emission field at a distance from the outer surface. For example, treatment system 1000 includes overlayer 1060, UV-LEDs 1050, reflective underlayer 1030, and interior region 1025. In FIG. 10, UV-LEDs 1050 are depicted as arranged to direct light away from a central shaft 1025 defined by the flexible UV light generation sheet. Advantageously, overlayer 1060 may be a UV transmissive scattering layer allowing light generated by UV-LEDs 1050 to be scattered diffusely across a range of directions. Overlayer 1060 may also serve as an encapsulating layer, providing water repellency and environmental protection to underlying UV-LEDs, conductors, and other components.

Interior region 1025 may correspond to a tubular structure, such as a hollow tube or solid cylindrical structure, for example. An adhesive may be used to mount the flexible UV light generation sheet to the interior region 1025. As an example, interior region may include a central shaft. Alternatively, the interior region may be open. In one example of a construction method an open interior region 1025 may be formed by wrapping a flexible UV light generation sheet around a mandrel. Herein the light generation sheet may be formed by first wrapping the reflective underlayer 1030 around the mandrel without an adhesive. A second underlayer 1030 may then be wrapped around the first underlayer 1030 which includes a thin adhesive layer so as to secure the form factor of the two underlayers 1030 in the shape of the mandrel but allowing the mandrel to be removed thereby forming an open interior region 1025.

Such a configuration is useful, for example, in embodiments where the flexible UV light generation treatment system 1000 is inserted into a container or fluid pathway and used to expose fluid, particles, or objects in the container or fluid pathway to UV light. Treatment system 1000 may correspond to a rod or stick that may be moved within the container or fluid pathway to target impurities in the stream. The movement may also induce turbulence and/or promote mixing.

Figure 11:
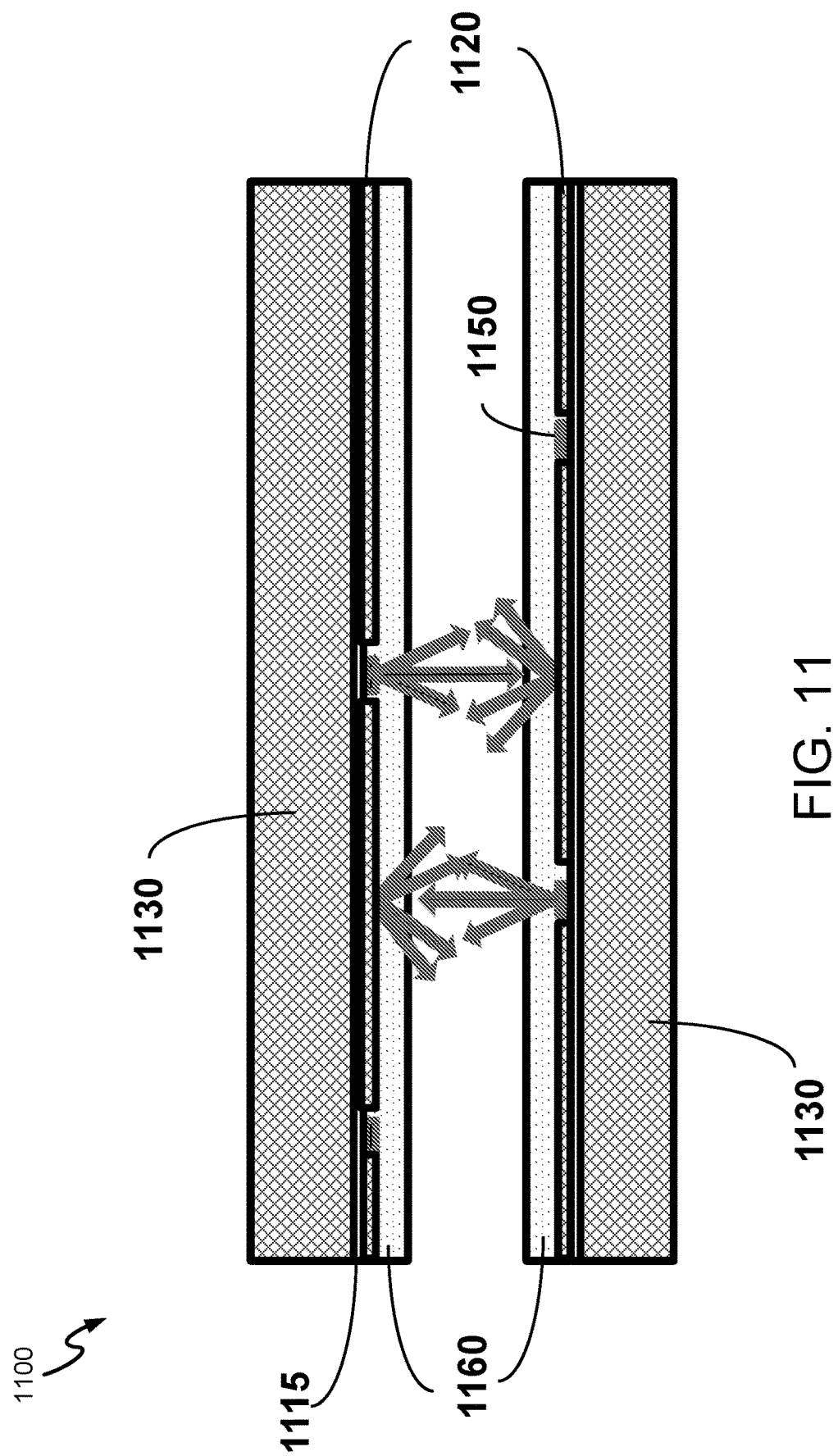
FIG. 11 provides a schematic illustration showing a cross-sectional view of a UV treatment system in accordance with some embodiments.

FIG. 11 corresponds to two flexible UV light generation sheets opposing each other and depicts a schematic cross-sectional illustration of a flexible UV light generation sheet useful for generating an uniform UV emission field at a distance from the flexible UV light generation sheet. As illustrated, the flexible UV light generation sheet 1100 includes an underlayer 1120, UV-LEDs 1150 supported by the substrate and an overlayer 1160 positioned over underlayer 1120 and UV-LEDs 1150. Underlayer 1120 may correspond, for example, to a UV diffuse reflective layer. It will be appreciated that additional layers may be included in a flexible UV light generation sheet 1100. For example multiple flexible UV light generation sheets may be used together to form a system. Flexible UV light generation sheet 1100 may be useful, for example, for lining walls of a container or vessel to allow fluids, particles, or objects within the container or vessel to be exposed to UV light for disinfection, purification, or other treatment purposes. Optionally, devices within a container or vessel, such as used for mixing a fluid or objects or particles suspended in a fluid, may have one or more surfaces lined with flexible UV light generation sheet 1100 to allow exposure of the fluid, objects, or particles to UV light for disinfection or purification purposes. As an example, one or more walls of a vessel, conduit, or pipe may be lined with flexible UV light generation sheet 1100 and/or a surface of a mixing vane may be lined with flexible UV light generation sheet 1100.

As another example, one or more flexible UV light generation sheets may be arranged in a pouch or pocket configuration, where a surface of a first flexible UV light generation sheet faces a surface of a second flexible UV light generation sheet. Such a configuration may correspond to two separate flexible UV light generation sheets or may correspond to a single flexible UV light generation sheet folded back on itself to form a pouch or pocket like configuration. As an example, for a rectangular pouch configuration, three sides of facing rectangular flexible UV light generation sheets may be joined or attached to make a rectangular pouch. Other shapes are possible.

Figure 12:
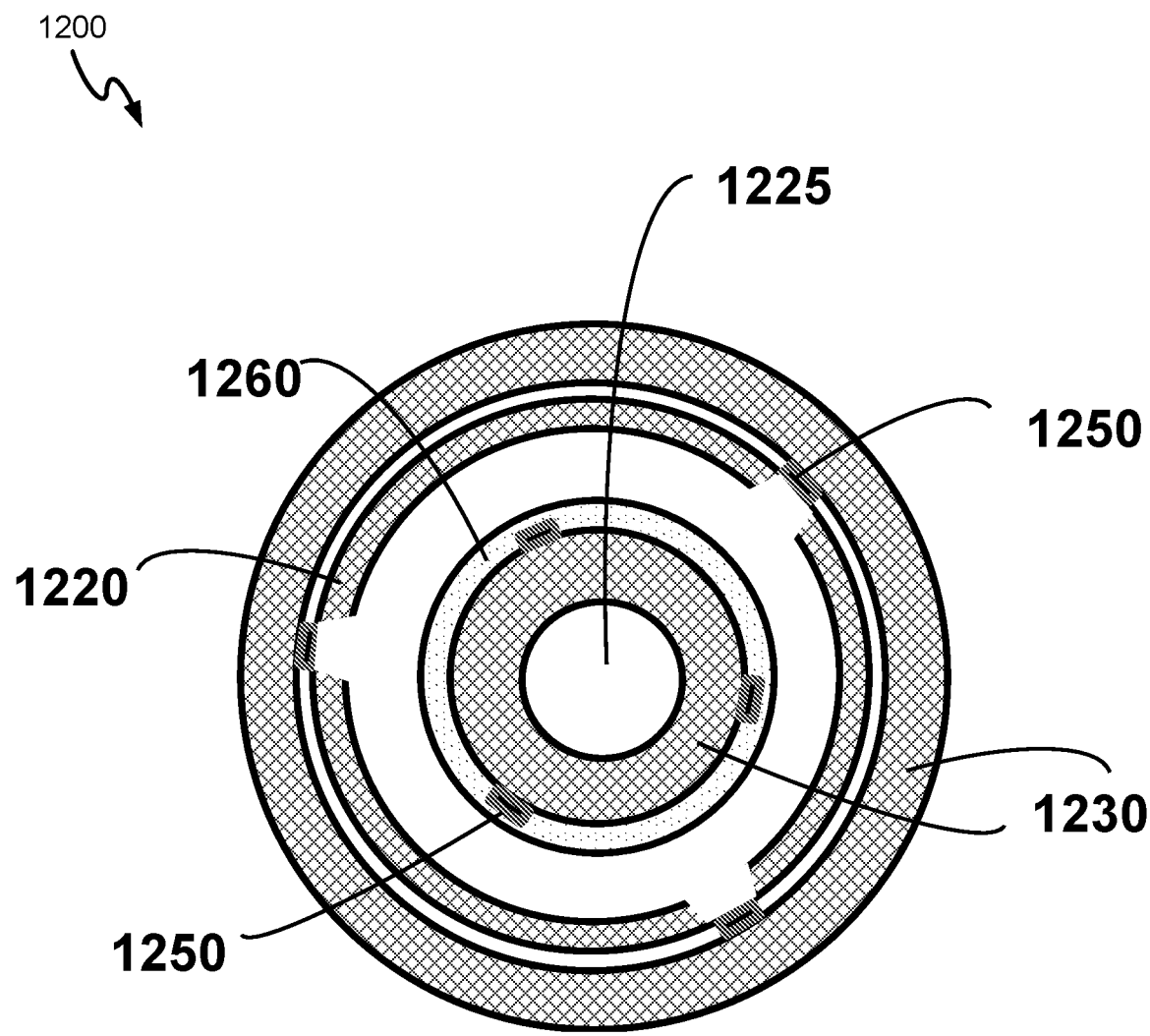
FIG. 12 provides a schematic illustration showing a cross-sectional view of a UV treatment system in accordance with some embodiments.

As another example, multiple flexible UV light generation sheets may be combined to form a UV light generation system 1200, as depicted FIG. 12. In FIG. 12, UV light generation system 1200 includes a first flexible UV light generation sheet 1205 and a second flexible UV light generation sheet 1210. First flexible UV light generation 1205 sheet may correspond to flexible UV light generation sheet 900 as depicted in FIG. 9. Second flexible UV light generation sheet 1210 may correspond to flexible UV light generation sheet 1000 as depicted in FIG. 10. As illustrated, first flexible UV light generation sheet 1205 and second flexible UV light generation sheet 1210 are arranged so that second flexible UV light generation sheet 1210 is positioned inside first flexible UV light generation sheet 1210. In addition, the UV-LEDs of each flexible UV light generation sheet are depicted as not directly opposed one another UV-LEDs. For example, UV light from UV-LEDS of first flexible UV light generation sheet 1205 is directed towards a scattering layer or a reflective layer of second flexible UV light generation sheet 1210. Similarly, UV light from UV-LEDS of second flexible UV light generation sheet 1210 is directed towards a reflective layer of first flexible UV light generation sheet 1205. In this way, an annular region 1215 may be formed between first flexible UV light generation sheet 1205 and second flexible UV light generation sheet 1210, such as to allow fluid to flow between them and be treated by UV light.

Figure 13A:
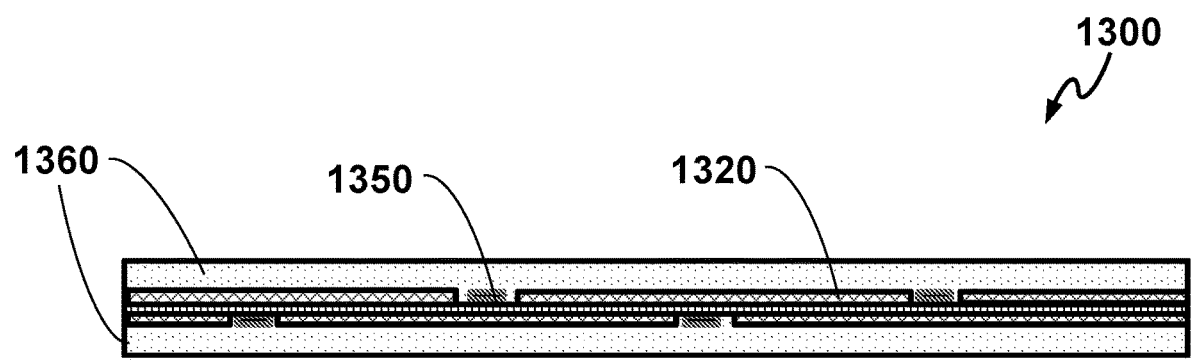
FIG. 13A and FIG. 13B provides schematic illustrations showing cross-sectional and side views of a UV treatment system in accordance with some embodiments.
Figure 13B:
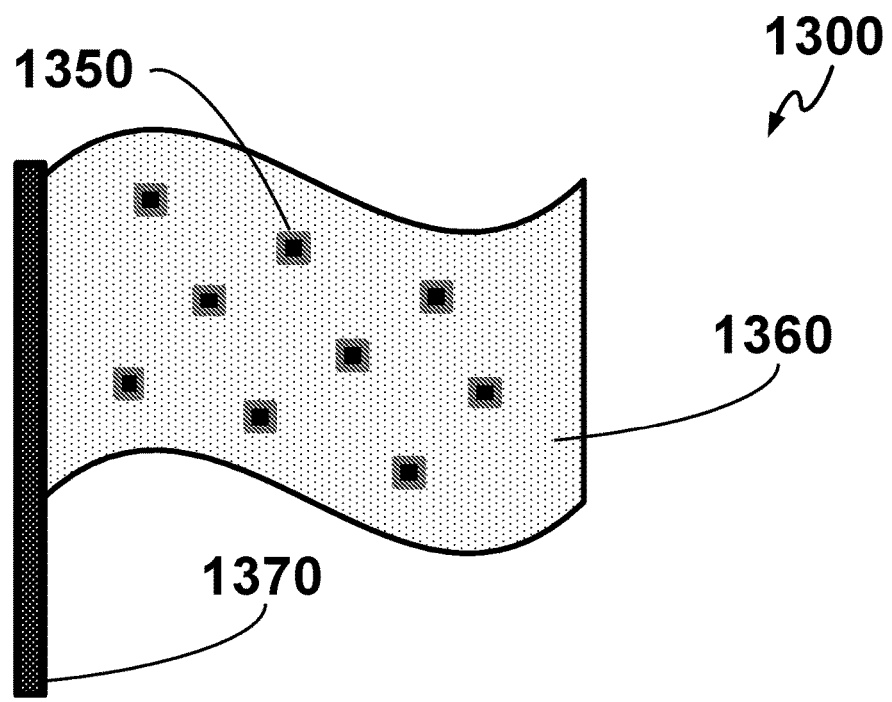

As another example, a flexible UV light generation sheet may optionally be a two-sided sheet. Flexible two-sided flexible UV light generation sheet 1300 is depicted in FIGS. 13A and 13B. FIG. 13A shows a cross-sectional schematic illustration of two-sided flexible UV light generation sheet 1300 including reflective layer 1320 and scattering overlayer 1360 covering reflective layer 1320 and UV-LEDs 1350. As illustrated, UV-LEDs 1350 are mounted on both sides of two-sided flexible UV light generation sheet 1300 with the reflective layer 1320 and scattering overlayer positioned on each side of two-sided flexible UV light generation sheet 1300. In this embodiment, UV-LEDs 1350 positioned on a first side of the two-sided flexible sheet 1300 do not back to any UV-LEDs positioned on a second side of the two-sided flexible sheet 1300. Flexible UV light generation sheet 1300 may be correspond to a flag type configuration, where flexible UV light generation sheet 1300 is fixed on one end with the other end free to move, such as in a fluid. FIG. 13B also shows a supporting structure 1370 and that flexible UV light generation sheet 1300 is supported only, for example, on one end by supporting structure 1370. In some embodiments, however, a flexible UV light generation sheet may be supported on two or more or all ends by various supporting structures. Supporting structure 1370 may include power and communications connections, such as power/voltage supplies, control circuitry, or communications feeds, for example between UV-LEDs and/or UV photodetectors and external circuitry by way of one or more conductors. It will be appreciated that FIG. 13B depicts a regular array of multiple UV-LEDs 1350 and that any conductors included with the array are not illustrated.

UV Diffuse Reflective Layer

A variety of materials are useful as a UV diffuse reflective layer for various flexible UV light generation sheets and treatment systems described herein. For example, a UV diffuse reflective layer may comprise one or more polymers or a polymer layer, such as a polymer selected from the group consisting of a fluoropolymer, a polyimide, a polyolefin, a polyester, a polyurethane, a polyvinyl, polymethyl methacrylate, or variations or derivatives thereof. Example polymers include, but are not limited to, polyethylene terephthalate (PET), polyethylene naphthalate (PEN), poly ether ether ketone (PEEK), cyclic olefin copolymer (COC), polycarbonate (PC), polyphenylene sulfide (PPS), polyetherimide (PEI), polyamideimide (PAI), polychloroprene, polyvinyl chloride (PVC), polyvinylidene chloride (PVDC), vinylidene chloride-vinyl chloride copolymers, vinyl chloride copolymers, vinylidene fluoride polymers, polyvinylidene fluoride (PVDF), fluorinated ethylene propylene (FEP), perfluoroalkoxy alkane (PFA), or polytetrafluoroethylene (PTFE). In one embodiment, the UV diffuse reflective layer may comprise an expanded polytetrafluoroethylene (ePTFE). In some embodiments, a UV reflective layer comprises a thin metal film. In some embodiments, a UV reflective layer comprises a dielectric stack. In some embodiments, a UV diffuse reflective layer exhibits a diffuse reflectivity of 50% or greater, 60% or greater, 70% or greater, 80% or greater, 90% or greater, 95% or greater, 97% or greater, 98% or greater, or 99% or greater for UV light, such as light having wavelengths between 200 nm and 400 nm. Example UV diffuse reflective layers include those exhibiting a diffuse reflectivity (diffuse reflective scattering) percentage for UV light, such as light having wavelengths between 200 nm and 400 nm, 50% or more (i.e., 50-100%), 60% or more, 70% or more, 80% or more, or 90% or more. In some embodiments, a UV diffuse reflective layer functions as an encapsulating, water resistance, or environmental protection layer.

Figure 18:
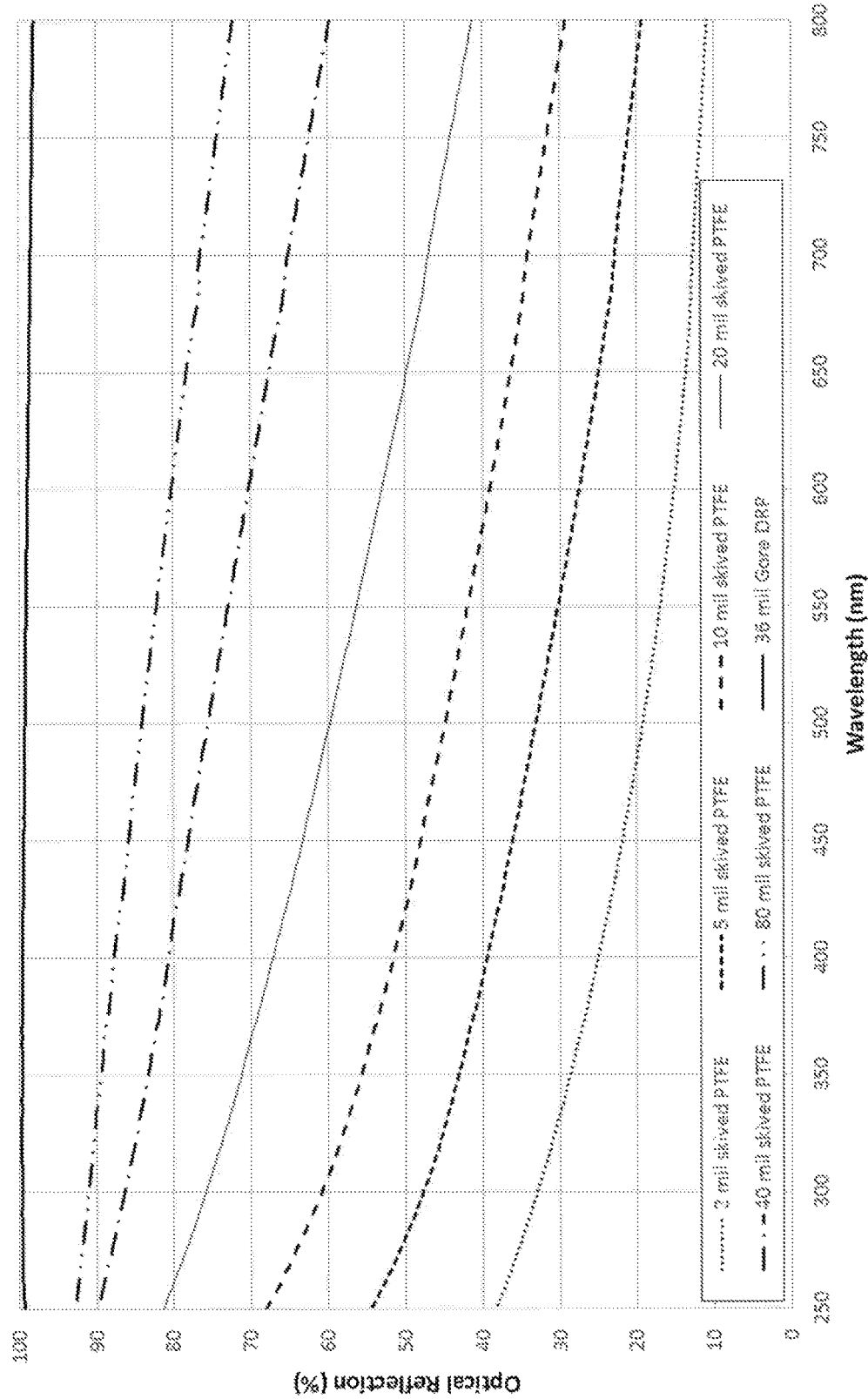
FIG. 18 provides a plot showing total reflectivity of a UV diffuse reflective layer as a function of wavelength.

A variety of exemplary materials that may be used as either a reflective layer, such as a reflective layer or a reflective underlayer. In publication "Reflectivity Spectra for Commonly Used Reflectors" by Martin Janacek, incorporated herein by reference, the author lists several materials which have greater than 97% reflectivity. In one embodiment the UV diffuse reflective layer comprises ePTFE. The ePTFE material comprises a microstructure of polymeric nodes and fibrils that demonstrates exceptional diffuse reflectivity in the UV spectrum. An exemplary ePTFE for the UV diffuse reflective layer, Gore DRP®, is produced by W.L. Gore & Associates of Newark, Del. FIG. 18 shows a plot of total reflectivity from 250 nm to 800 nm of various thicknesses of skived PTFE along with Gore DRP®. This material is described in U.S. Pat. No. 5,596,450 or 6,015,610, the entire contents and disclosures of which is hereby incorporated by reference. While packed granular based PTFE material provides good diffuse reflectance properties, the node and fibril structure of ePTFE provides a much higher diffuse reflectance property and has higher mechanical strength.

The UV diffuse reflective layer may be thin and lightweight. Making the UV diffuse reflective layer lighter and less expensive to employ expands the applications for the flexible UV light generation sheet. In one embodiment the UV diffuse reflective layer, including any coating or filler, may have a thickness from 0.01 mm to 2 mm, e.g., from 0.05 to 1.5 mm or from 0.1 to 1.2 mm. In one embodiment, the UV diffuse reflective layer has a high index of light reflection at a thickness of less than 0.3 mm.

UV Transparent and Scattering Layers

A variety of materials are useful as a UV transparent layers or UV transmissive scattering layer for various flexible UV light generation sheets and systems described herein. As noted above, UV transparent layers and scattering layers are useful, for example, as overlayers.

In embodiments, a UV transparent layer or UV transmissive scattering layer may comprise one or more polymers or a polymer layer, such as a polymer selected from the group consisting of a fluoropolymer, a polyimide, a polyolefin, a polyester, a polyurethane, a polyvinyl, polymethyl methacrylate, or variations or derivatives thereof. Example polymers include, but are not limited to, polyethylene terephthalate (PET), polyethylene naphthalate (PEN), poly ether ether ketone (PEEK), cyclic olefin copolymer (COC), polycarbonate (PC), polyphenylene sulfide (PPS), polyetherimide (PEI), polyamideimide (PAI), polychloroprene, polyvinyl chloride (PVC), polyvinylidene chloride (PVDC), vinylidene chloride-vinyl chloride copolymers, vinyl chloride copolymers, vinylidene fluoride polymers, polyvinylidene fluoride (PVDF), fluorinated ethylene propylene (FEP), perfluoroalkoxy alkane (PFA) or polytetrafluoroethylene (PTFE). In some embodiments, a polymer useful as a UV transparent layer corresponds to a PTFE, such as an ePTFE, which is a highly inert hydrophobic material. Accordingly, the PTFE is chemically resistant and liquid-proof which is useful when the UV transparent layer or UV transmissive scattering layer is in contact with the fluid stream. In some embodiments, a UV transparent layer or UV transmissive scattering layer functions as an encapsulating, water resistance, or environmental protection layer.

Preferably, a UV transparent layer has a very low optical absorption (e.g., less than 10%, less than 5%, or less than 1%) so that a very high percentage of the light is transmitted through the UV transparent layer. In some embodiments, a UV transparent layer exhibits a transparency for UV light of 50% or greater, 75% or greater, or 90% or greater, such as light having wavelengths between 100 nm and 400 nm. In one embodiment, the UV transparent overlayer has a UV transmission of at least 80% at 250 nm.

In addition to low optical absorption, an optional but desirable property for an overlayer is haze or scattering character. Haze is forward scattering of light greater than 2.5 degrees from the optical transmission axis. This property will defocus the light thereby increasing the uniformity of the photon density in the fluid stream. In embodiments, UV transmissive scattering layers comprise UV transparent materials. Inclusion of surface features or one or more fibrils, nodes, pores, and the like in a transparent material provides more opportunities for scattering of light at surfaces or transitions between materials of different indices of refraction (e.g., air and polymer), and may provide a scattering character or haze to a material. Haze and scattering are further described in ASTM standard D1003, hereby incorporated by reference.

Figure 19:
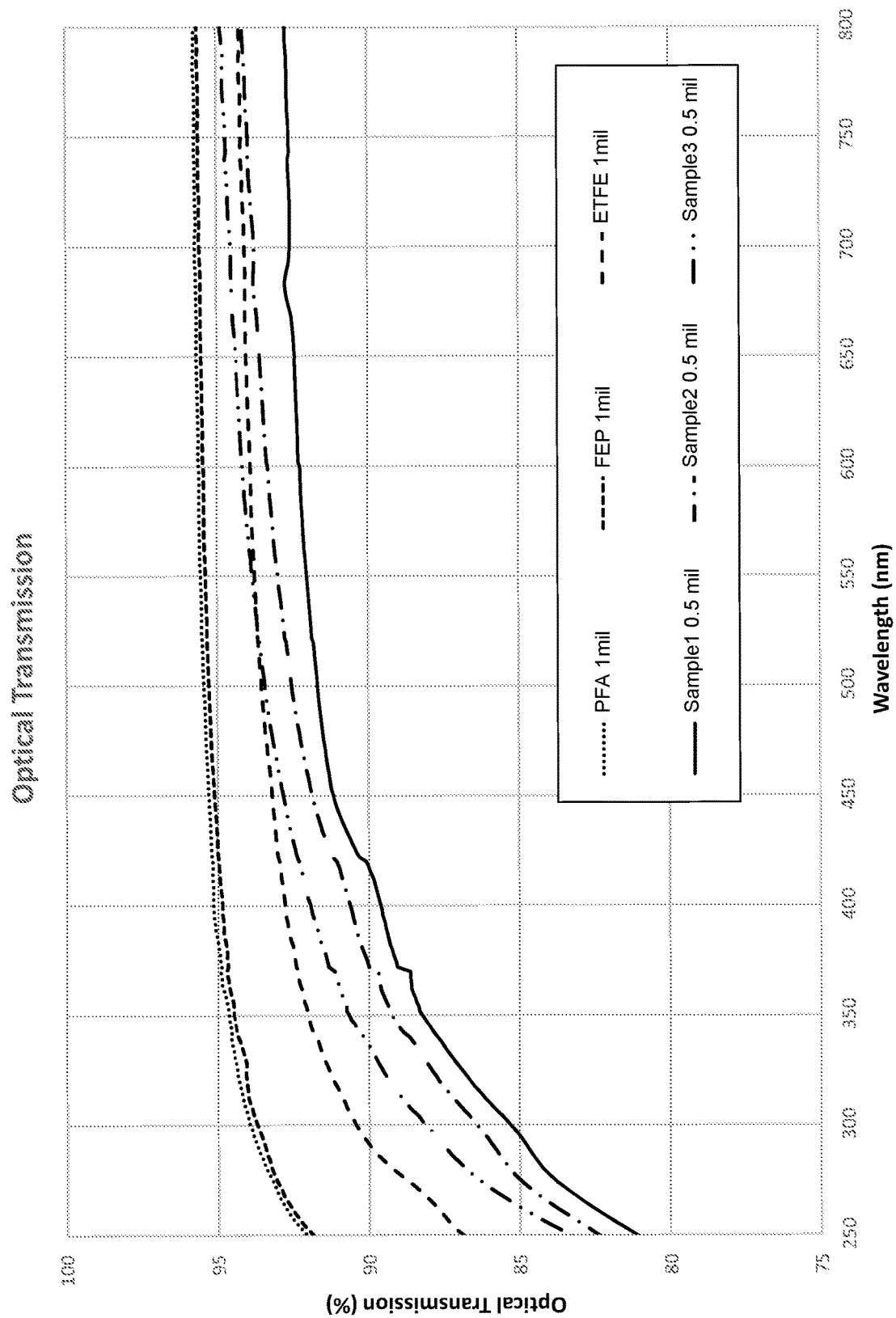
FIG. 19 provides a plot showing total transmission of different materials as a function of wavelength.
Figure 20:
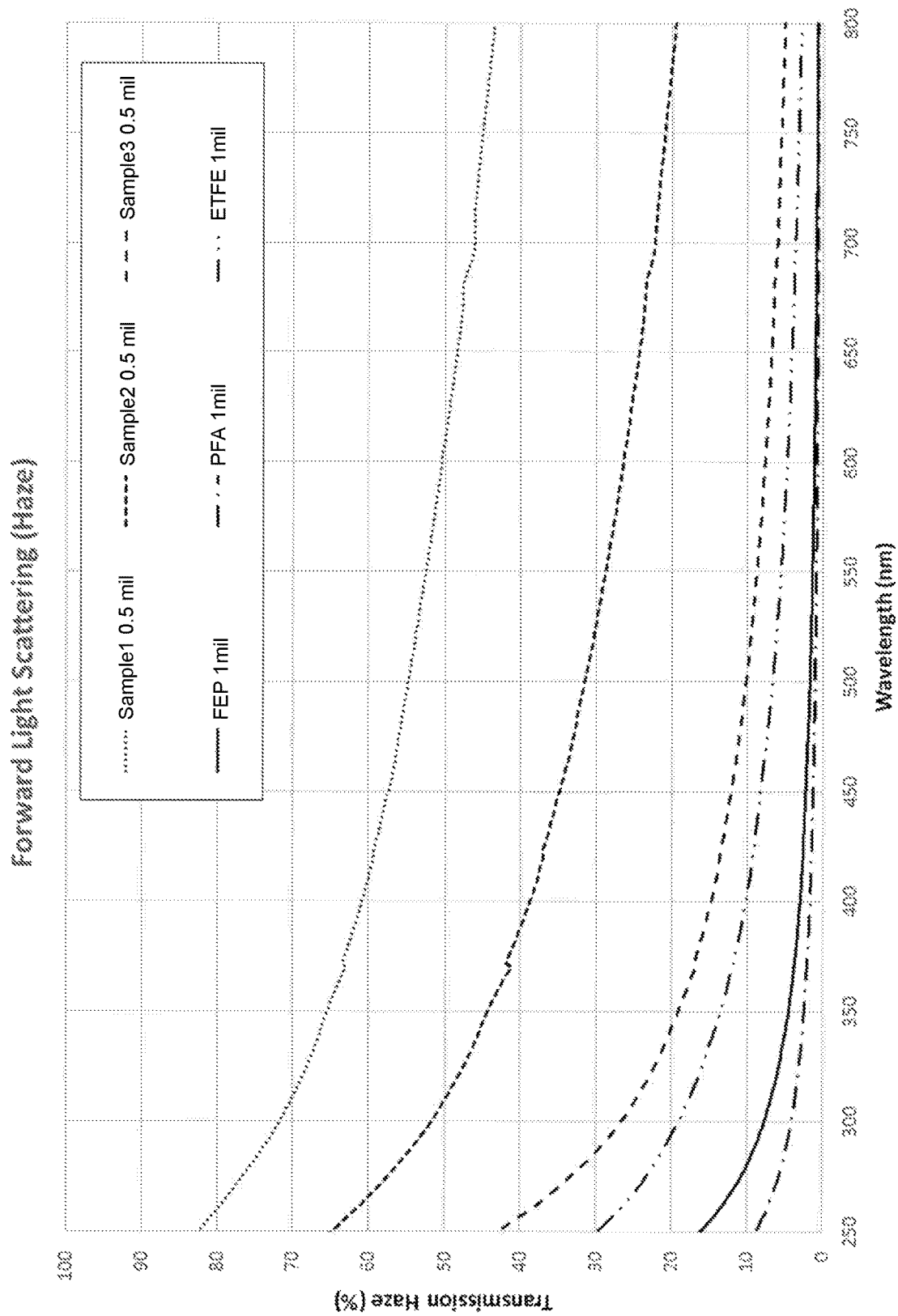
FIG. 20 provides a plot showing haze percent of different materials as a function of wavelength.

Exemplary overlayer materials are described in U.S. Pat. Nos. 5,374,473 and 7,521,010, the entire contents and disclosures of which is hereby incorporated by reference. The patents describe a compressed ePTFE article which has improved properties over conventional cast or skived PTFE. FIG. 19 shows a plot of transmission vs. wavelength for three samples (S1, S2, S3) of a compressed ePTFE article as described in the patents, along with FEP, PFA and ETFE (Tefzel™). The compressed ePTFE articles have a thickness of 0.5 mil, while the FEP, PFA and ETFE have a thickness of 1 mil. In general, thinner thicknesses will have higher transmission percentages due to lower absorption losses. However, T=1−R−A (Transmission calculates as 100% minus reflection losses R minus absorption losses A) and in these films the reflection coefficient is much larger than the absorption coefficient (as calculated from this equation using optical transmission and reflection data on the same films). So even higher transmission numbers can be attained by not using air in the transmission path from the LED to the fluid medium. FIG. 20 shows a plot of haze vs. wavelength for the same six articles. It will be appreciated that in these samples the higher percent transmission material has the lower haze. Depending on the application, one may choose to use a material with more scattering to promote light diffusion and reduce dark spots in the fluid stream even though the total optical power has been reduced. The overlayer material may have an optical transmission coefficient (T) of greater than 70% and a haze coefficient (H) of greater than 20% or preferably T>80% and H>50%.

An overlayer may be adhered or laminated to a UV diffuse reflective layer, a flex circuit, a substrate or supporting layer, the UV-LEDs, or any other material or layer in a flexible UV light generation sheet. In one embodiment, an overlayer covers openings in a UV diffuse reflective layer that expose corresponding UV-LEDs.

Example UV transparent layers and UV transmissive scattering layers may have thicknesses of 7 microns to 100 microns.

UV transparent tube. In one embodiment, the assembly comprises a UV transparent tube and the flexible UV light generation sheet is wrapped around the tube. In one embodiment the flexible UV light generation sheet is wrapped along the outer surface of the tube. In other embodiments, the flexible UV light generation sheet is wrapped and is placed along the inner surface. The flexible UV light generation sheet is flexible and lack a structural rigidity to maintain the fluid pathway. A tube provides the necessary rigidity for the fluid pathway. This may be advantageous for in-line use for disinfection, purification, sterilization, or other treatment systems. The tube should be sufficient to withstand the temperature of the stream being treated and chemically resistant as needed.

In one embodiment, the UV transparent tube comprises a polymer, such as a fluoropolymer, a polyimide, a polyolefin, a polyester, a polyurethane, a polyvinyl, polymethyl methacrylate, polyethylene terephthalate (PET), polyethylene naphthalate (PEN), poly ether ether ketone (PEEK), cyclic olefin copolymer (COC), polycarbonate (PC), polyphenylene sulfide (PPS), polyetherimide (PEI), polyamideimide (PAI), polychloroprene, polyvinyl chloride (PVC), polyvinylidene chloride (PVDC), vinylidene chloride-vinyl chloride copolymers, vinyl chloride copolymers, vinylidene fluoride polymers, polyvinylidene fluoride (PVDF), fluorinated ethylene propylene (FEP), perfluoroalkoxy alkane (PFA) or polytetrafluoroethylene (PTFE). The material may be selected to provide a rigidity to the flexible UV light generation sheet. However, in other embodiments, the UV transparent tube may also be flexible.

Composite Structures

It will be appreciated that the various layers and components described above may be joined, adhered, or otherwise configured in a variety of manners to form a composite structure. For example, any one or more of a support layer, a substrate, a conductor, a UV-LED, a UV diffuse reflective layer, a UV transparent layer, a UV transmissive scattering layer, an encapsulating layer, and other components may be attached or positioned adjacent to one another using any suitable means. In some embodiments, layers may be laminated to one another to allow for layers to be joined or attached in a composite structure. Example lamination processes include thermal-based lamination processes and adhesive-based lamination processes. In some embodiments, layers or components may be attached or adjoined using one or more adhesives. Optionally, a continuous adhesive layer is positioned between two objects to allow the two objects to be adjoined, such as where an adhesive layer is positioned completely between the two objects at all points where the two objects are adjacent to one another. Optionally, a discontinuous adhesive layer, i.e. adhesive dots or adhesive lines, is positioned between two objects to allow the two objects to be adjoined, such as where a one or more adhesive layers are positioned between the two objects at only a subset of points where the two objects are adjacent to one another. Example adhesives include, but are not limited to, acrylics, polyamides, polyacrylamides, polyesters, polyolefins, polyurethanes, polysilicones or the like. Useful adhesives include those that do not impact the flexibility of the joined materials.

In embodiments, advantageous adhesives include UV stable adhesives. As used herein, the term "UV stable" indicates that a material, such as an adhesive, is resistant to UV light, allowing long term use without degrading. In some embodiments, a UV stable material may not significantly degrade when exposed to long durations of UV light, such as years or more. Suitable UV stable adhesives include silicones, acrylates or adhesives with UV absorbers or inhibitors added thereto. In addition, UV stable material may advantageously be non-absorbing (i.e., transparent) in the UV region or may exhibit only small amounts of absorption. Example UV stable materials include PTFE, ePTFE, fluorinated ethylene propylene (FEP) or perfluoroalkoxy alkane (PFA). Example UV stable adhesives include thermoplastic fluoropolymers. Preferred adhesives are FEP, a copolymer of tetrafluoroethylene and hexafluoropropylene; PFA, a copolymer of tetrafluoroethylene monomers containing perfluoroalkoxy side chains, and EFEP, a copolymer of ethylene, tetrafluoroethylene, and hexafluoropropylene. Alternatively, copolymer resins of tetrafluoroethylene and perfluoroethylene-alkyl ether monomers (e.g., PAVE, PMVE, and/or CNVE) can be made with compositions and molecular weights to act as adhesives that exhibit excellent thermal and UV resistance (pressure sensitive, thermoplastic, or crosslinked). Such copolymer resins are disclosed, for example, in U.S. Pat. Nos. 7,488,781; 8,063,150; 8,623,963; 7,462,675; and 7,049,380.

UV-LED Configurations

Figure 14:
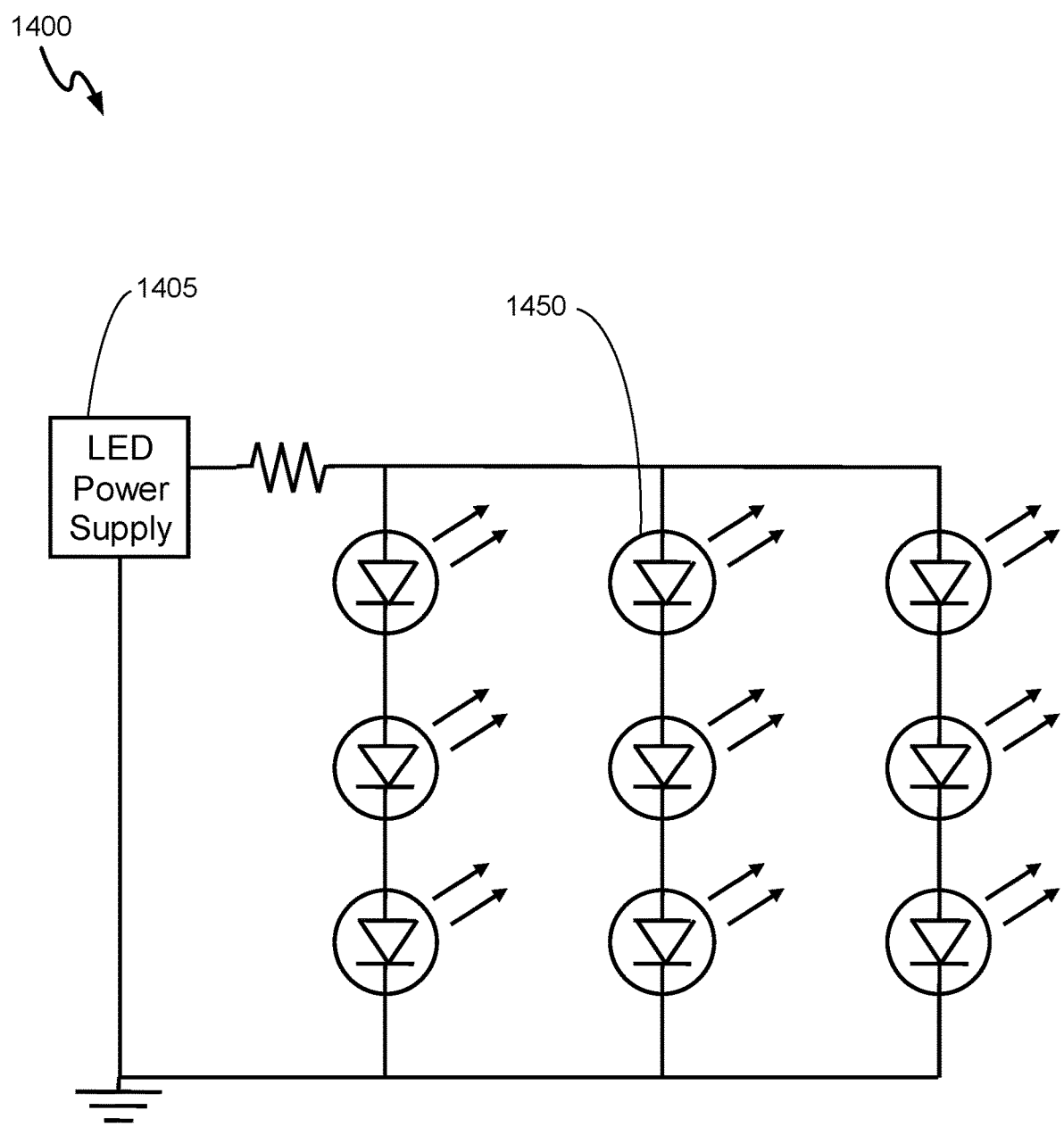
FIG. 14 provides an example circuit for driving LEDs in a series configuration.
Figure 15:
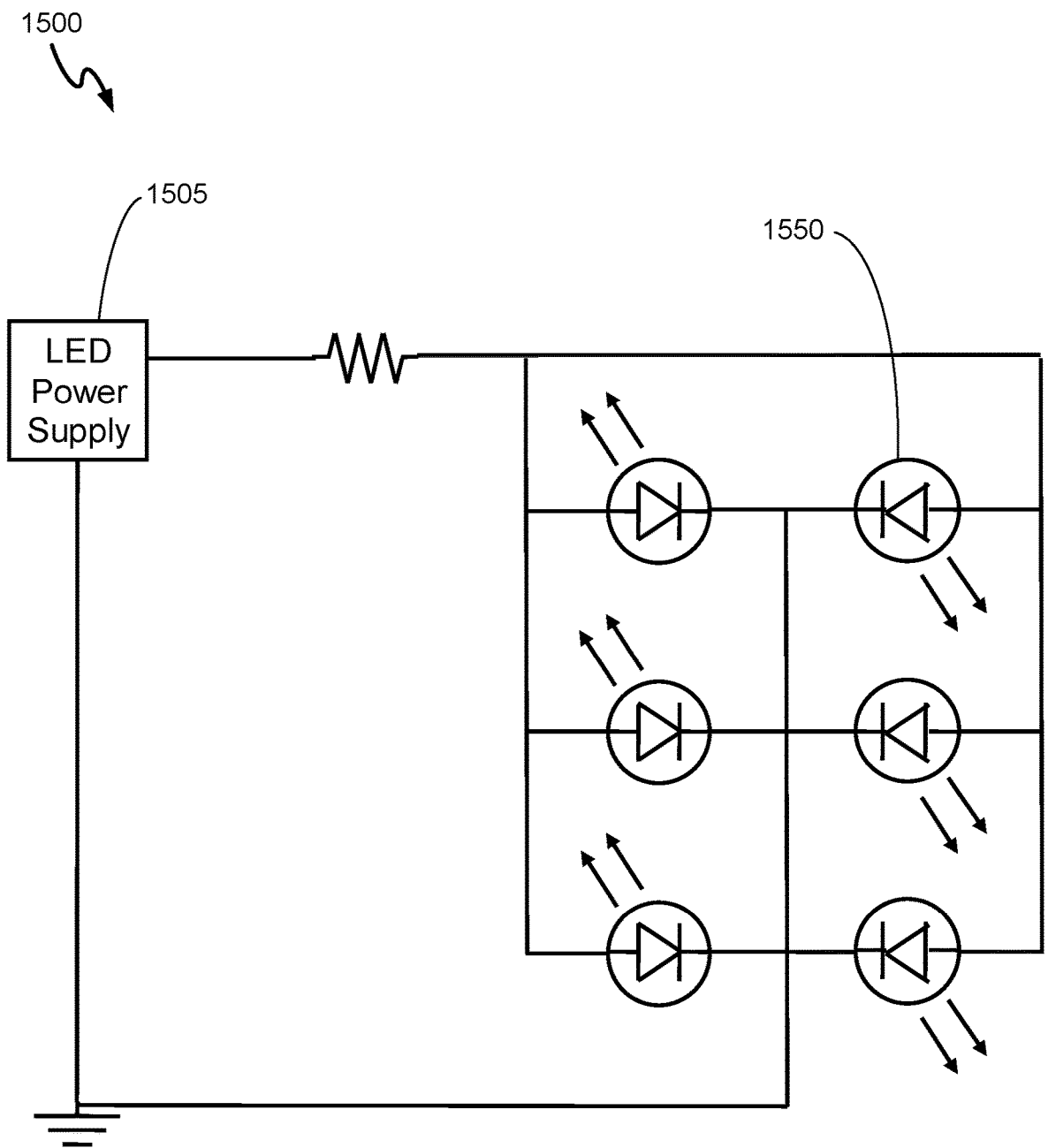
FIG. 15 provides an example circuit for driving LEDs in a parallel configuration.

UV-LEDs may be incorporated in the flexible UV light generation sheets and treatment systems described herein in a variety of manners. To distribute the UV light within the fluid pathway the UV-LEDs are arranged to form a regular spacing about the flexible UV light generation sheet. In other embodiment, non-regular spacing of the UV-LEDs may also be used. Multiple UV-LEDs are arranged in a parallel or series configuration. For example, FIG. 14 provides an example circuit diagram 1400 showing multiple UV-LEDs 1450. As illustrated, an LED power supply 1405 is shown driving three sets of three series connected UV-LEDs 1450, such that each UV-LED 1450 in a series is driven by the same amount of current. FIG. 15 provides another example circuit diagram 1500 showing multiple UV-LEDs 1550. As illustrated, LED power supply 1505 drives the UV-LEDs 1550 in parallel, such that each UV-LED 1550 is driven by the same voltage, for example. It will be appreciated that the configuration illustrated in FIG. 14 depicts not only UV-LEDs connected in series, but also series connected UV-LEDs that are also connected in a parallel configuration.

In some embodiments, UV-LEDs incorporated into flexible UV light generation sheets and treatment systems correspond to surface mounting devices, which may be advantageous for some implementations. For example, in some embodiment where flat flexible cable-based conductors are used, surface mounting of UV-LEDs may have dimensions that match the pitch between conductors, allowing for seamless integration and manufacture of a flexible UV light generation sheet.

In some embodiments, UV-LEDs useful with the flexible UV light generation sheets and treatment systems described herein include UVA LEDs, exhibiting emission between wavelengths of 315 nm and 400 nm. In some embodiments, UV-LEDs useful with the flexible UV light generation sheets and treatment systems described herein include UVB LEDs, exhibiting emission between wavelengths of 280 nm and 315 nm. In some embodiments, UV-LEDs useful with the flexible UV light generation sheets and treatment systems described herein include UVC LEDs, exhibiting emission between wavelengths of 100 nm and 280 nm. Exemplary UV-LEDs emit UV light with wavelengths between 260 nm and 265 nm, between 270 nm and 280 nm, 305 and 315 nm. It will be appreciated, however, that the wavelength of UV light and the associated UV-LEDs may be selected that best matches or at least partially overlaps a destruction effectiveness curve of a target toxin or target pathogen, for example. As an example, a germicidal effectiveness curve for *Escherichia coli* may exhibit a peak at about 265 nm, and use of UV-LEDs emitting at this wavelength may provide an advantage for destroying these pathogens or toxins in the fluid pathway.

A variety of UV-LED structure types are suitable for use with the flexible UV light generation sheets and treatment systems described herein. In some embodiments, a UV-LED, one or more UV-LEDs or each UV-LED corresponds to a surface-mount device. Use of surface-mount devices are advantageous when making a flexible UV light generation sheet or a treatment system using a flat flexible cable, as certain flat flexible cables have standard pitches between conductors or widths that may match commercially available surface-mount type UV-LEDs. Other advantages provided by the use of surface-mount structures include the ability to use pick-and-place machinery to assemble portions of a flexible UV light generation sheet or treatment system. Other types of UV-LED structures are useful for some embodiments described herein, including through-hole LEDs, miniature LEDs, high-power LEDs, round, square, etc. In addition, any LED structure capable of generating UV light of a desired wavelength or wavelength region are useful with the embodiments described herein. For example, in some embodiments, a UV-LED has an AlGaN-structure, AlN structure, a GaN structure, or combinations of these.

It is to be understood that other UV light emitting semiconductors, such as laser diodes, for example VCSELs (vertical cavity surface emitting lasers), are considered UV-LEDs for the purposes of this patent application Feedback and Intensity Control It will be appreciated that exposure of toxins or pathogens to a particular dose of UV light may result in destruction of the toxins or pathogens, while lower doses may not completely destroy the toxins or pathogens. Similarly, if the toxin or pathogen is present in higher concentrations, the particular dose may not sufficiently destroy the toxins or pathogens. Advantageously, flexible UV light generation sheets and treatment systems described herein optionally include feedback mechanisms that permit control over the dose or output intensity of UV light generated. As an example, in some embodiments, a flexible UV light generation sheet or treatment system may include one or more UV sensors. For example, in the configurations illustrated in FIGS. 1-13B, one or more UV-LEDs may be substituted for a UV sensitive photodetector, such as a photodiode, that is positioned in electrical communication with a monitoring circuit that is used to provide feedback for increasing or decreasing a current and/or voltage used to drive one or more UV-LEDs in order to maintain a suitable UV light field.

Figure 16:
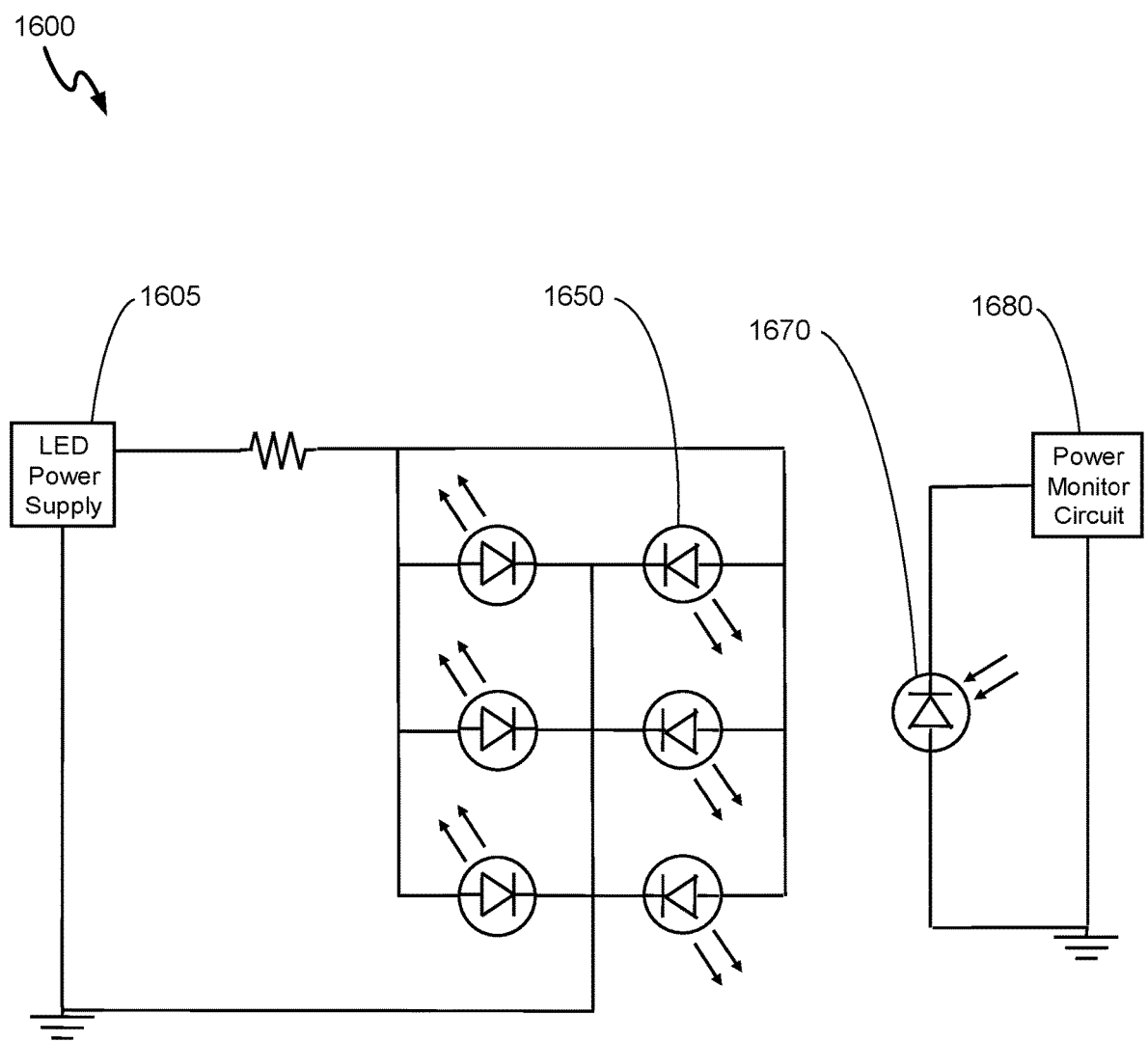
FIG. 16 provides an example circuit for driving LEDs and monitoring UV light output using a UV sensitive photodetector.

FIG. 16 provides an example circuit diagram 1600 in which multiple UV-LEDs 1650 are driven by LED power supply 1605. A UV sensitive photodetector 1670 is depicted as connected to a power monitor circuit 1680 that may be used to monitor a UV light intensity or power as output by the UV-LEDs 1650. By monitoring a UV light intensity or power, the power monitor circuit 1680 may provide information, used, such as by the power monitor circuit or another computer or control circuitry, to adjust the voltage or current generated by LED power supply 1605. In this way, the intensity of UV light can be monitored and adjusted to accommodate a target UV light dose or intensity useful for destroying toxins or pathogens.

Methods of Making Treatment Systems

It will be appreciated that a variety of techniques may be employed for making the treatment systems and flexible UV light generation sheets described herein. FIGS. 17A-17F provide schematic overviews of an example aspects of an embodiment of a method of making a flexible UV light generation sheet. FIGS. 17A-17F provide schematic cross-sectional front views (1), side views (2), and top views (3) of a flexible UV light generation sheet during steps of a fabrication method. In FIG. 17A, multiple conductors 1702 are illustrated, each corresponding to a flat conductor of a flat flexible cable 1704. For purposes of illustration, only a section of a conductor cable is shown, but it will be appreciated that conductors of any number and size may be useful with various embodiments of the invention. Optionally, the jacketing surrounding the conductors may be UV transmissive or reflective polymers. In FIG. 17B, the flat flexible cable 1704 is positioned adjacent to a substrate 1706. In FIG. 17C, a UV diffuse reflective layer 1708 is positioned adjacent to the flat flexible cable 1704. In FIG. 17D, openings 1710 are created at locations over two of the flat conductors 1702, through both the UV diffuse reflective layer 1708 and the jacketing of the flat flexible cable 1704. In addition, in FIG. 17D, two of the flat conductors 1702 are segmented. Openings may be created using known processes in the industry, such as laser ablating or mechanical cutting. In FIG. 17E, UV-LEDs 1712 are positioned in each opening and joined to the respective flat conductor segments 1702. UV-LEDs may be attached using known processes in the industry, such as soldering or epoxying. In FIG. 17F, an overlayer 1714 is provided adjacent to the UV diffuse reflective layer, such as a UV transmissive scattering layer or a UV transparent layer. The attachment of the substrate, reflective, or transparent layers may be facilitated with the use of adhesives.

It will be appreciated that, for some embodiments, a separate substrate may not be required. For example a jacketing of a conductor may provide a suitable support structure for the conductors. Alternatively or additionally, an overlayer may not be required for some embodiments. It will further be appreciated that some embodiments may not require a UV diffuse reflective layer and so the UV diffuse reflective layer may be substituted for a UV transparent layer or a UV transmissive scattering layer.

The so formed flexible UV light generation sheets may be arranged in a configuration for exposing a fluid to UV light generated by the flexible UV light generation sheet. For example, the flexible UV light generation sheet may be arranged to enclose a fluid pathway. As another example, the flexible UV light generation sheet may be arranged to form a tubular shape. Optionally, the flexible UV light generation sheet may be helically wrapped, longitudinally wrapped, or circumferentially wrapped around a tube or central shaft. Optionally, the flexible UV light generation sheet may be arranged along an interior surface of a vessel or along a surface of a structure positioned within a vessel.

Figure 21:
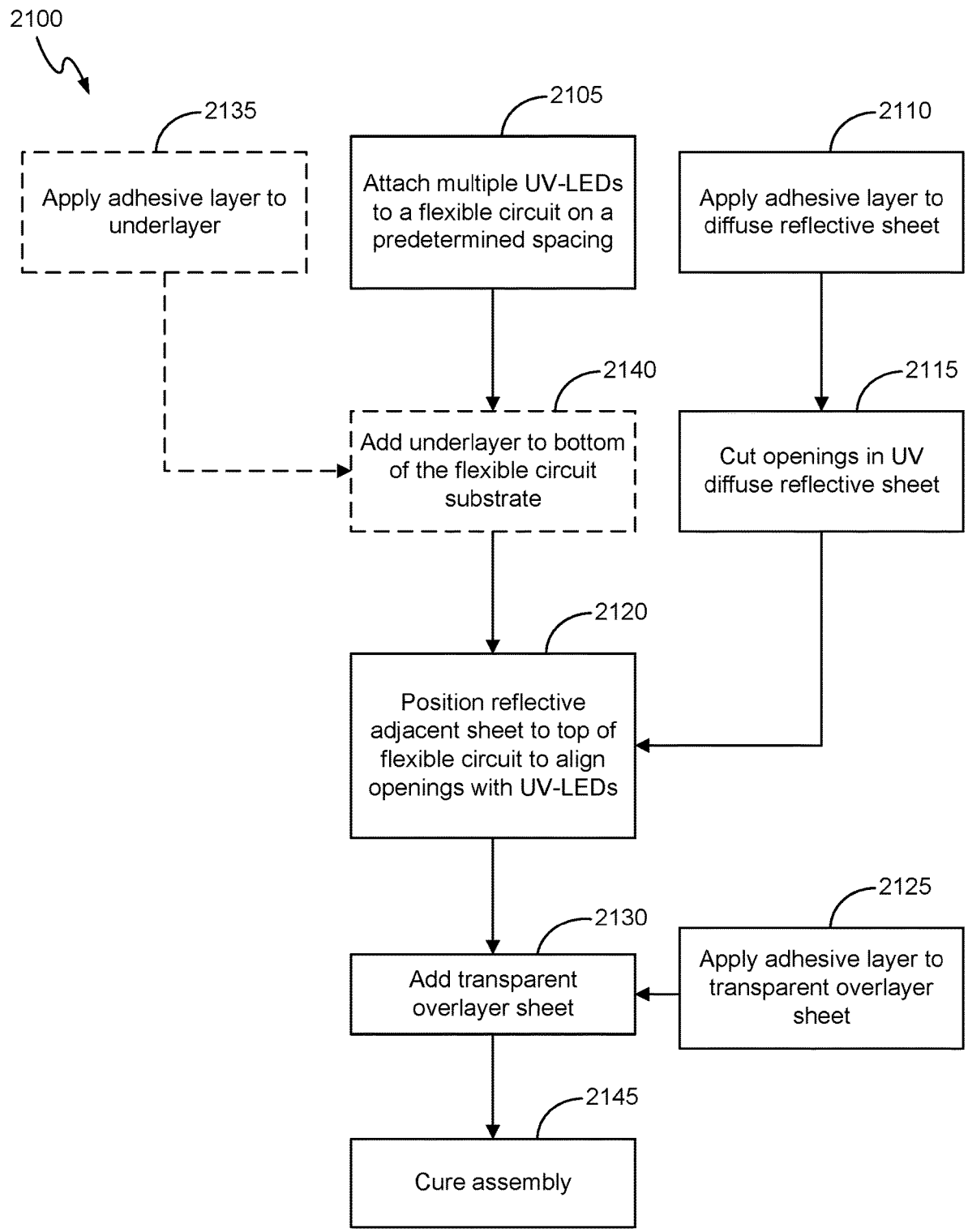
FIG. 21 provides an overview of an example method of making a UV light generation system in accordance with some embodiments.

An overview of a method 2100 for the assembly of a UV light generating sheet, such as depicted in FIG. 7A, is shown in FIG. 21. At block 2105, multiple UV-LEDs are attached to the flexible circuit via known practices in the industry, such as surface mounting technology, which includes chip on board and SMD attachment. The UV-LEDs may be in semiconductor die form and flip-chipped or wirebonded to the flex circuit conductive traces in a chip on board process. Alternatively, the UV-LEDs may be already packaged in a SMD (surface mount device) carrier package, where the UV-LED packages are attached to the flexible circuit with conductive adhesives or solders. In some embodiments, the flexible circuit is made by a method that includes removing portions of a jacketing of the ribbon cable or flat flexible cable to expose UV-LEDs or attachment locations for the UV-LEDs. It will be appreciated that the flexible circuit may be substituted by a ribbon cable or other flexible conductor assembly, as described above. The UV LEDs have a predetermined spacing that is used to create the openings in block 2115. At block 2110, an adhesive layer is applied to a surface of the UV diffuse reflective sheet. As described herein the adhesive layer for each layer or sheet may be a continuous layer of film or a pattern of dots or lines. Preferable adhesives are thermoplastic fluoropolymers such as FEP (melting point (mp) 260° C.), PFA (mp 305° C.), THV (mp 120-230° C.), and EFEP (mp 158-196° C.). In other embodiments, an adhesive layer may alternatively or additionally be applied to the top of the flexible circuit. Openings are cut into the UV diffuse reflective sheet at block 2115. Next, the UV diffuse reflective sheet is positioned to align openings with the UV-LEDs, at block 2120. By a similar method, an adhesive layer is applied to one surface of a transparent overlayer sheet, as depicted at block 2125. In block 2130, the transparent overlayer sheet is positioned adjacent to a surface of the UV diffuse reflective sheet opposite to the flexible circuit. At block 2145, the assembly is cured in an oven or preferably in a heated press at a temperature from 125 to 325° C. In one optional embodiment, the underlayer sheet can be added by a similar method at blocks 2135 and 2140. Although optional block 2135 indicates that the adhesive layer may be attached to the underlayer sheet, the adhesive layer may alternatively or additionally be applied to the bottom of the flexible circuit.

The assembly of the double-sided UV light generating sheet, such as the flag configurations shown in FIGS. 13A and 13B, is similar to method 2100 as depicted in FIG. 21. In this case the UV-LEDs are mounted on two sides of the flexible circuit and there is no optional reflective underlayer sheet. In this design, the UV-LEDs are not back-to-back so, for practical purposes, the UV diffuse reflective sheet next to the top UV-LEDs functions as the UV diffuse reflective sheet underlying the UV-LEDs on the opposite side. Alternatively, a single-sided UV light generating sheet may be folded back on to itself to create the flag configurations in FIGS. 13A and 13B.

A method for making a light generating tube, such as depicted in FIGS. 8A and 8B, involves wrapping a light generating sheet around a mandrel, such as a mandrel of the desired tubular shape. The wrapping may be helical, longitudinal, or circumferential to form the desired tubular shape. The mandrel is a cylindrical rod made of a material, such as a metal, that can withstand the cure temperatures used in the method. The wrapped sheet is then further wrapped with an underlayer, such as a reinforcing layer, optionally with an adhesive, and cured to solidify the assembly. Further protective coatings may be applied over the tube assembly. Cure steps may optionally be done at different points in the method. The mandrel is then removed from the tube assembly to create the fluid path.

Figure 22:
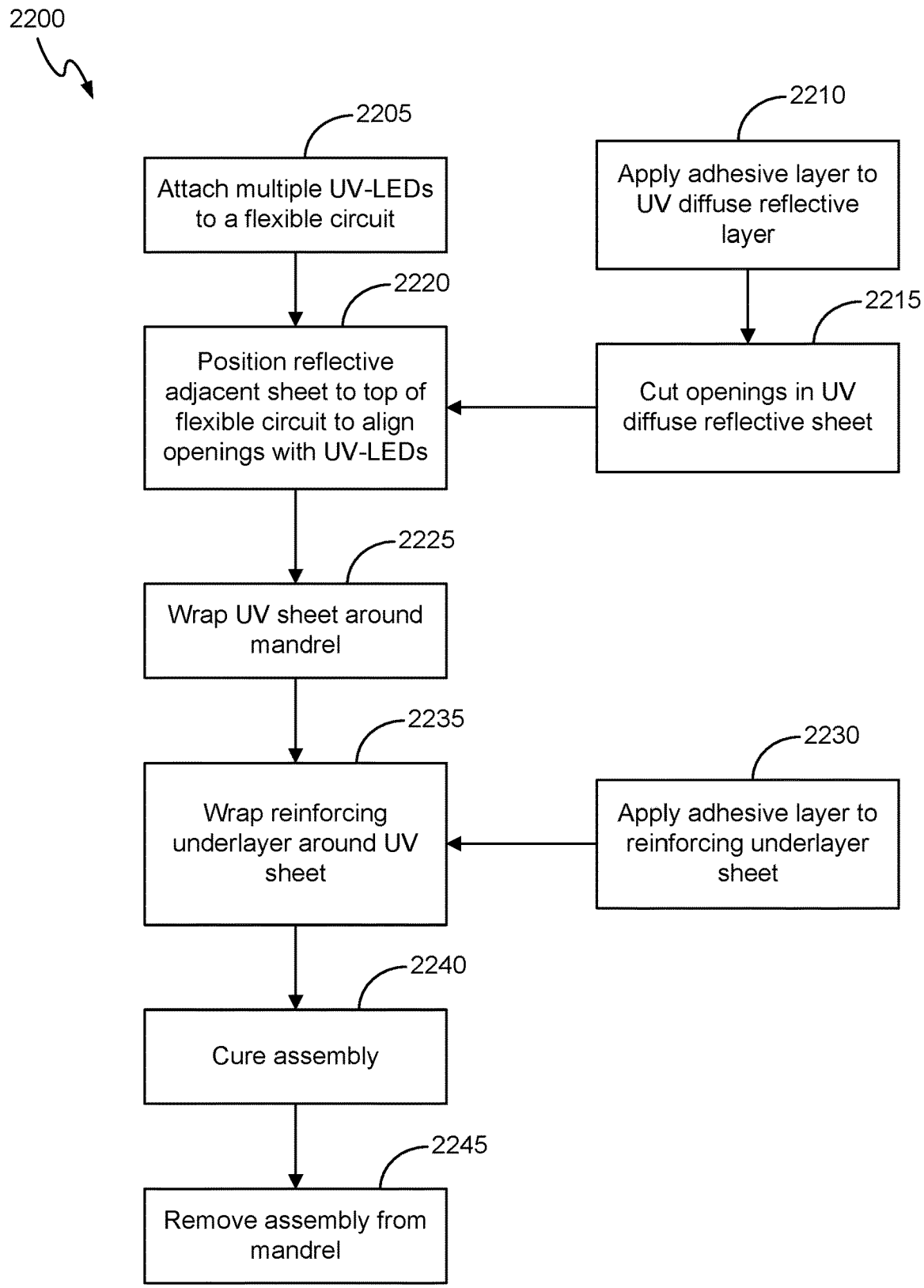
FIG. 22 provides an overview of an example method of making a UV light generation system in accordance with some embodiments.

A method 2200 is shown in FIG. 22 for wrapping a light generating sheet in tubular form. A flexible circuit comprising multiple UV-LEDs is assembled, in a manner described herein, at block 2205. An adhesive is applied to one surface of a UV diffuse reflective layer at block 2210, and openings are cut in the UV diffuse reflective layer at block 2215. The flexible circuit is aligned with the UV diffuse reflective layer at block 2220 such that the openings align with the UV-LEDs to form a UV light generating sheet. The UV light generating sheet is then wrapped around a mandrel at block 2225. An underlayer, which optionally may be a reinforcing layer with reflective properties, is wrapped around the UV light generating sheet with an adhesive, as shown at blocks 2230 and 2235. Additional layers or coatings may optionally be added to the outside of the tubular assembly. At block 2240, the assembly is then cured, for example in an oven, and the mandrel is removed, at block 2245. In one embodiment, a lower melting point fluoropolymer adhesive EFEP is used so the curing temperature does not harm the flexible circuit. The product embodiment of this method may correspond to, for example, that shown in FIG. 9A.

Figure 23:
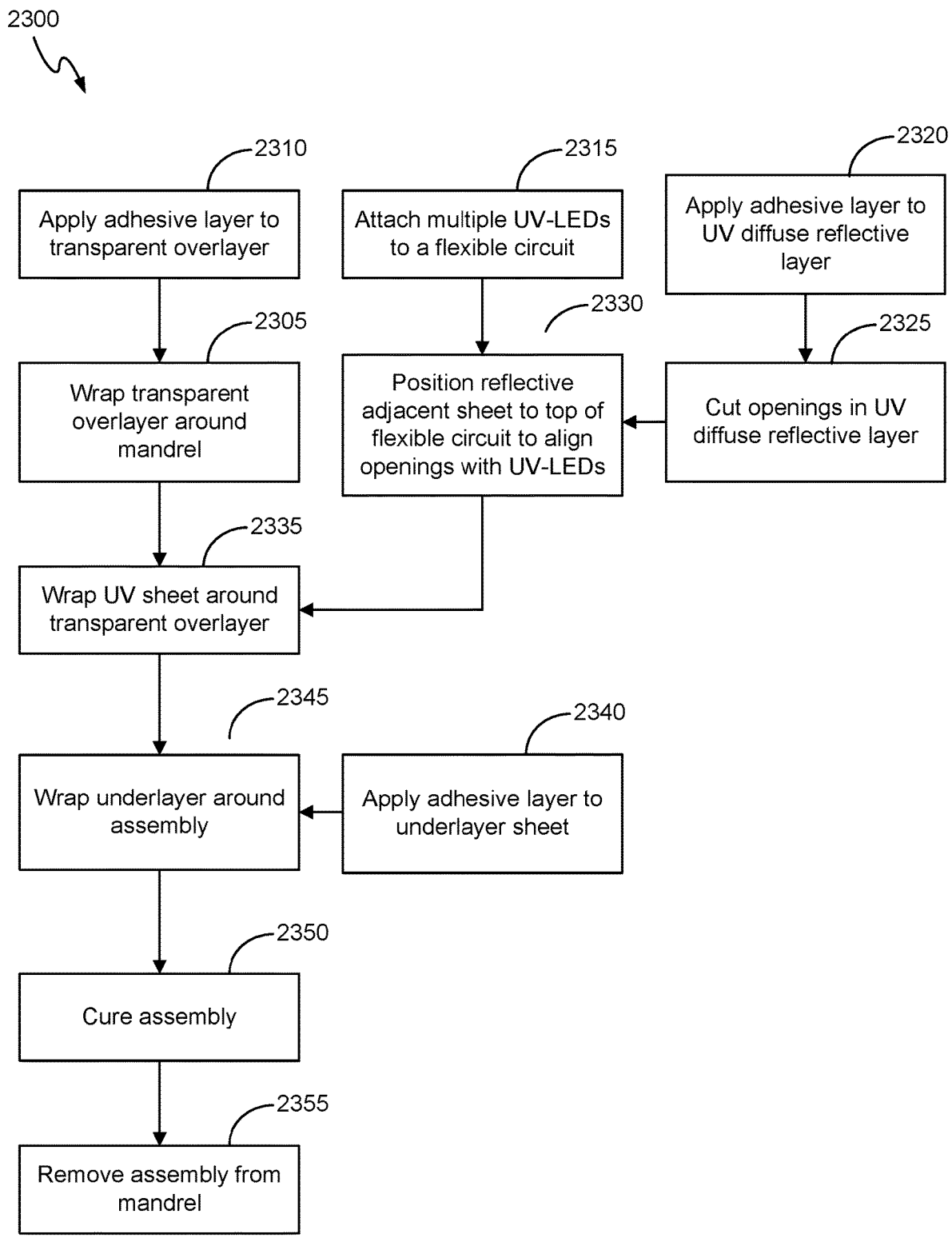
FIG. 23 provides an overview of an example method of making a UV light generation system in accordance with some embodiments.

Another method 2300 is shown in FIG. 23, which may form a product corresponding to, for example, that shown in FIG. 9B. At block 2305, a transparent overlayer (e.g., layer 960 in FIG. 9B), is wrapped around a mandrel to form a tube, optionally with an adhesive applied at block 2310. The transparent overlayer can be made of materials described previously. The transparent overlayer can optionally be multilayer wrapped several times with an adhesive to secure the transparent overlayer to itself but not to the mandrel. In other embodiments, the transparent overlayer is a tube that is slid over the mandrel. The transparent overlayer is optionally cured at this stage. In an exemplary method, a preferred transparent overlay material is the aforementioned compressed ePTFE material, the adhesive is FEP, and the tubular structure is cured at 280° C. (a temperature greater than the adhesive melting temperature but less than the melting temperature of the transparent overlay material). An alternative method of fabricating the transparent overlayer (e.g., layer 960 in FIG. 9B), is to slide a pre-manufactured FEP tube over the mandrel. In this example, the following cure temperature steps should be less than the melting temperature of the FEP so as to enable the mandrel to be removed from the tubular assembly. After the transparent tube is formed, the rest of the method is similar to that described in FIG. 22. For example, a flexible circuit comprising multiple UV-LEDs is assembled at block 2315. An adhesive is applied to one surface of a UV diffuse reflective layer at block 2320, and openings are cut in the UV diffuse reflective layer at block 2325. The flexible circuit is aligned with the reflective layer at block 2330 such that the openings in the layer align with the UV-LEDs to form the UV light generating sheet. The UV light generating sheet is then wrapped around the transparent overlayer at block 2335. An additional underlayer, which optionally may be a reinforcing layer or UV diffuse reflective layer, is wrapped around the assembly using an adhesive layer, as shown at blocks 2340 and 2345. Additional layers or coatings may optionally be added to the outside of the UV light generating sheet. At block 2350, the assembly is then cured, for example in an oven, and the mandrel is removed, at block 2355.

The methods shown by FIGS. 21-23 create openings in the UV diffuse reflective sheet. In other embodiments, openings may be created by gaps between adjacent longitudinal sides as described by the methods in FIGS. 24-26. Regardless of the method of making UV light generating system, once in use the process may comprise energizing the multiple UV-LEDs to generate UV light, wherein at least a portion of the generated UV light from the multiple UV-LEDs passes through the corresponding openings and into the fluid pathway.

Figure 24A:
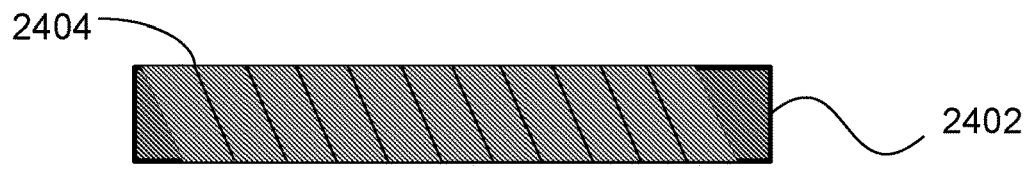
FIGS. 24A-24F provide schematic illustrations of methods of making a UV light generation system using one UV diffuse reflective layer in accordance with some embodiments.
Figure 24B:
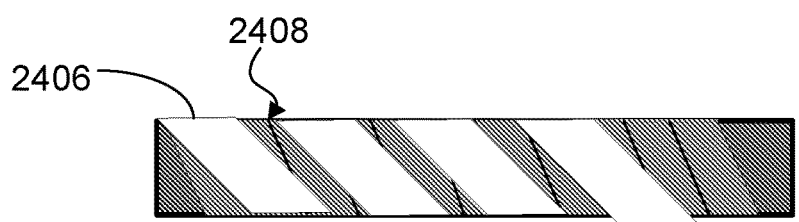
Figure 24C:
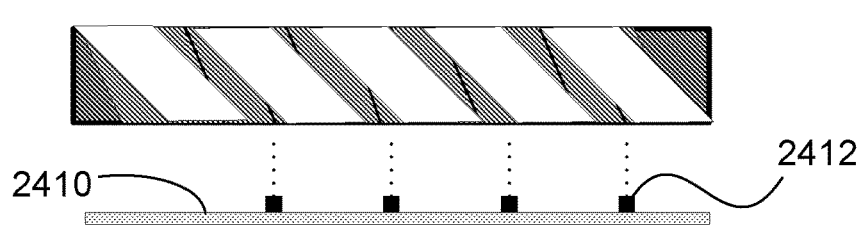
Figure 24D:
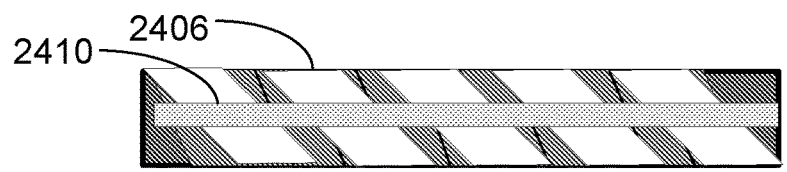
Figure 24E:
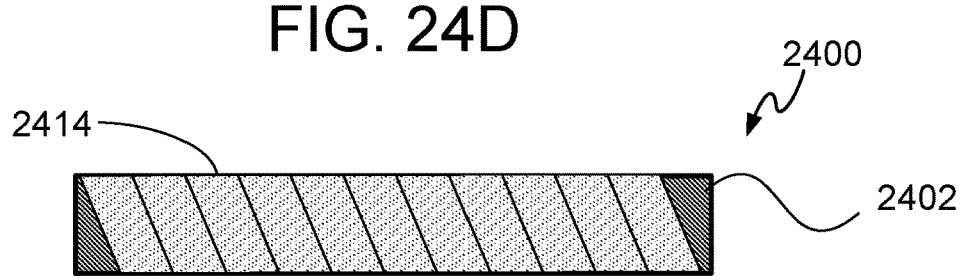

In one embodiment, reflective layers may be wrapped by the method that is shown by FIGS. 24A-24E. A mandrel 2402, e.g., a cylindrical rod, is used to form a tubular UV light generation system 2400 and once formed the mandrel 2402 is removed to form the fluid path. In one embodiment as shown in FIG. 24A, a transparent material 2404 is wrapped around the mandrel 2402 to form an overlayer. The wrapping is done to prevent gaps between the adjacent longitudinal sides of the transparent material 2404. Optionally, adjacent longitudinal sides of the transparent material overlap. In other embodiments, a transparent overlayer that is tubular may be fitted around the mandrel 2402, by sliding the transparent overlayer over the mandrel 2402. The overlayer may have an adhesive surface of a continuous transparent adhesive or by a pattern of adhesive dots or adhesive lines facing outward. Next, a UV diffuse reflective layer 2406 is wrapped around the mandrel 2402, or overlayer if present. When being wrapped, a gap 2408 is formed between adjacent, e.g., nearby, longitudinal sides of the UV diffuse reflective layer 2406. The UV diffuse reflective layer 2406 is wrapped along the length of the mandrel to the desired size. The UV diffuse reflective layer 2406 may have an adhesive surface of a transparent adhesive or by a pattern of adhesive dots or adhesive lines facing outward. In one embodiment, the UV diffuse reflective layer 2406 is flexible and may be made of a UV stable material, e.g., expanded polytetrafluoroethylene. The gap 2408 may be substantially uniform between the adjacent sides to provide a separation distance between the adjacent sides from 0.5 to 100 mm, preferably 0.5 to 20 mm, e.g., 1 to 25 mm, or from 3 to 15 mm. A flexible circuit 2410 having multiple UV-light emitting diodes 2412 is positioned to align the UV-light emitting diodes 2412 with the gap 2408. This allows the UV light to be transmitted into the interior of the UV light generating system 2400 when in use. Although one flexible circuit is shown in FIG. 24C, in further embodiments, multiple flexible circuits may be used adjacent to the UV diffuse reflective layer 2406. When multiple flexible circuits are used, UV-light emitting diodes are off-set to achieve a wide distribution of UV light within the UV light generating system 2400. In FIG. 24D, an underlayer 2414 is wrapped over the UV diffuse reflective layer and flexible circuit. The wrapping is done to prevent gaps between the adjacent longitudinal sides of the underlayer 2414. Optionally, adjacent longitudinal sides of underlayer 2414 overlap. One or more curing processes may optionally be included in the method depicted in FIGS. 24A-24E, and following FIG. 24E, the mandrel 2402 may be removed to create an internal fluid path.

Figure 24F:
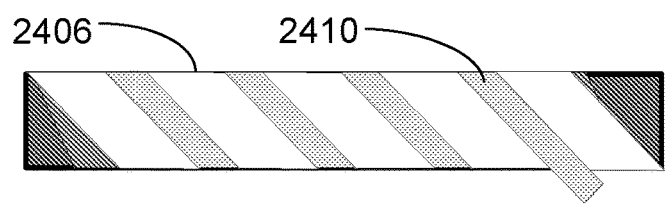

Optionally, flexible circuit 2410 may itself include a diffuse UV reflective overlayer with openings included at the positions of UV LEDs 2412, as described above. Such a flexible circuit may alternatively be wrapped in a helical fashion around the mandrel 2402, or overlayer 2404 if present, with the gap 2408 having a width that is greater than or equal to the width of flexible circuit 2410 to allow flexible circuit 2410 to fit into the helical gap 2408, as indicated in FIG. 24F. This configuration may be used in place of or in addition to that depicted in FIG. 24D. This configuration benefits from a longer flexible circuit 2410 that may include more UV-LEDs and enables tighter curvatures with the tube assembly in a bent configuration.

Figure 25A:
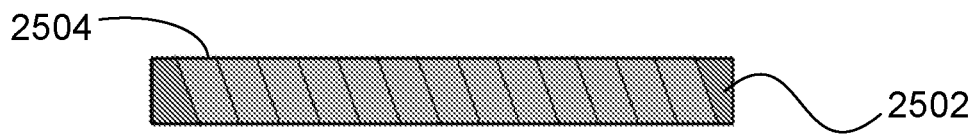
FIGS. 25A-25F provide schematic illustrations of methods of making a UV light generation system using two UV diffuse reflective layers in accordance with some embodiments.
Figure 25B:
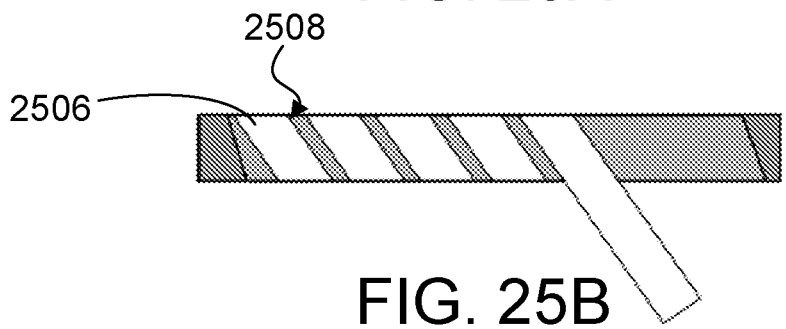
Figure 25C:
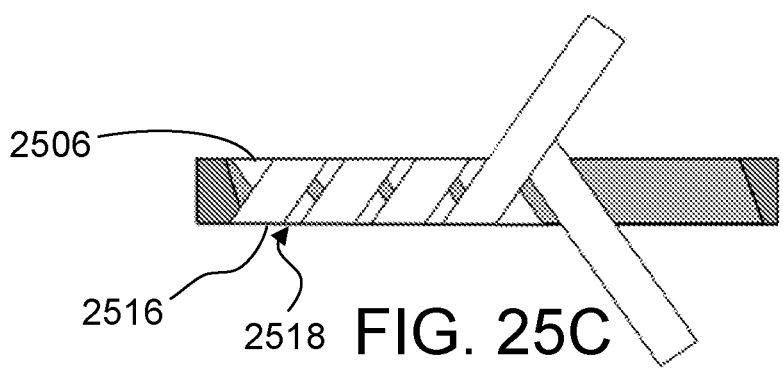

In a further embodiment, the method may involve wrapping a second UV diffuse reflective layer 2516 as shown in FIGS. 25A-25F. As discussed above, a first UV diffuse reflective layer 2506 is wrapped around the mandrel 2502, and optionally, the transparent material 2504 that forms the overlayer, such that a first gap 2508 is present between adjacent, e.g. nearby, longitudinal sides of first UV diffuse reflective layer 2506. In FIG. 25C, the second UV diffuse reflective layer 2516 is wrapped around the first UV diffuse reflective layer 2506. In one embodiment, the second UV diffuse reflective layer 2516 is counter-wrapped in a direction that is opposite to the first UV diffuse reflective layer 2506. In further embodiments, additional UV diffuse reflective layers may be used. The second gap 2518 between adjacent, e.g., nearby, longitudinal sides of the second UV diffuse reflective layer 2516 overlap with the first gap 2508 to form openings 2520. As discussed herein, the openings 2520 may have a variety of shapes and sizes. The openings 2520 correspond to the pitch of the spacing of UV-LEDs 2512 on a flex circuit 2510. In one example, a 0.5 inch wide, 0.01 inch thick, ePTFE layer was wrapped at a pitch of 17 mm with a gap of 4 mm in the right hand direction and then a second ePTFE layer was crossed wrapped in the left hand direction at a pitch of 17 mm with a gap of 4 mm. The resulting opening in the reflective layers is 4 mm diamond on a pitch of 17 mm. In one embodiment, the overlap of the first gap and second gap may create several different openings. For example, there may be additional openings on the back side (not shown in FIG. 25D) that are spaced halfway between the openings on the top side.

Figure 25D:
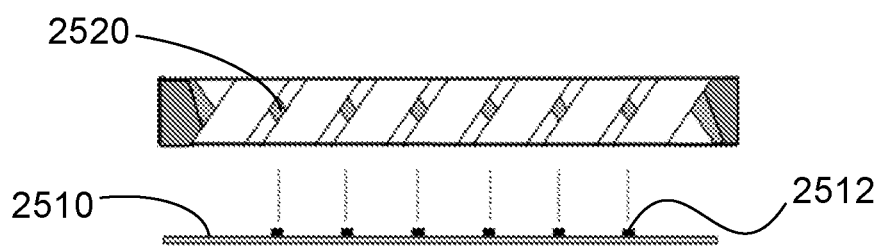
Figure 25E:
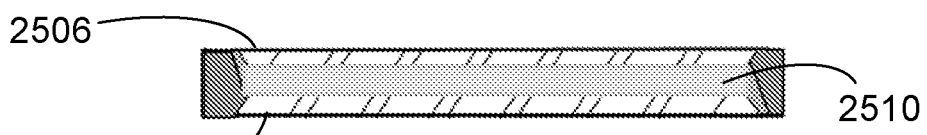
Figure 25F:

FIG. 25D shows the flex circuit 2510 having UV-LEDs 2512 laid straight in a longitudinal manner. In one embodiment, multiple flex circuits may be used. In another embodiment, the method includes helically wrapping a flex circuit having UV-LED in a helical fashion around the tube, the spacing of the UV-LEDs being such that they align with the openings. This embodiment benefits from a longer flexible circuit that enables tighter curvatures with the tube assembly in a bent configuration. As shown in FIG. 25F, optional underlayer 2514 is wrapped around the assembly, which may have reflective or diffuse reflective properties.

To complete the tubular UV light generation system 2500 assembly, the assembly is then cured and the mandrel 2502 is removed to create the internal fluid path.

Figure 26A:
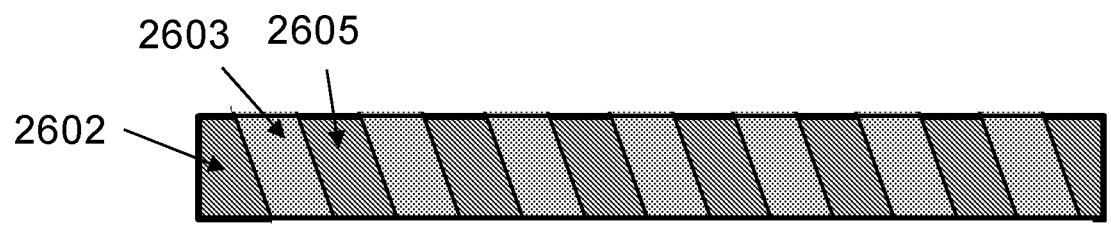
FIGS. 26A and 26B provide schematic illustrations of methods of making a UV light generation system using one UV diffuse reflective layer and one transparent overlayer in accordance with some embodiments.
Figure 26B:
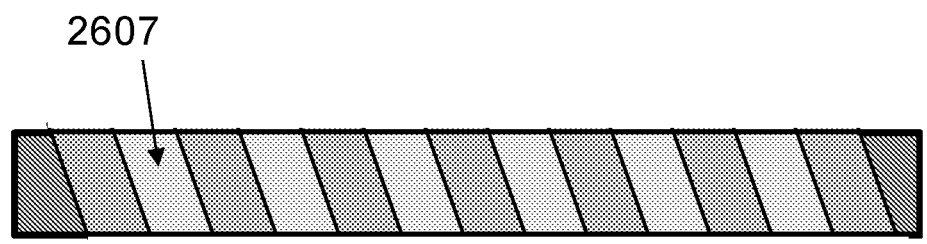

As previously described, an optional embodiment for the transparent overlayer is to include photocatalysts such as $TiO_2$ on the surface that is exposed to the fluid medium. In previously described embodiments, the overlayer is positioned above the UV-LED such that the emitted light path is from LED to photocatalyst to fluid medium. Since the photocatalysts in touch with the fluid medium are generally more effective at generating reactive oxygen species that can disinfect the fluid stream, it may be desirable to have an optical path from LED through fluid stream to surface photocatalysts (e.g., on other side of tube). FIGS. 26A and 26B depict an embodiment of forming the transparent overlayer that will enable the light emitted from the UV-LED to impinge on the photocatalysts from the fluid medium side. A first transparent overlayer 2603 is wrapped around mandrel 2602 with a gap 2605 as shown in FIG. 26A. A second overlayer 2607, comprising a photocatalytic surface layer, optionally of the same width as gap 2605, is then wrapped in the gap of transparent overlayer 2603 as shown in FIG. 26B. At this stage in the process the transparent overlayer equivalent to FIG. 24A or FIG. 25A is finished and the various steps described in FIG. 24B-24F or 25B-25F can be implemented to finish construction of the photocatalytic light generating tube. An optional embodiment is described in FIG. 24F with the addition of a photocatalytic layer to the UV reflective layer 2406.

Additional Examples

Additional non-limiting examples are further described.

E1. A method of making an ultraviolet (UV) light generation system, the method comprising: wrapping a first UV diffuse reflective layer in a first direction around a mandrel with a first gap between adjacent longitudinal sides of the first UV diffuse reflective layer, wherein the first UV diffuse reflective layer is flexible; and positioning a flexible circuit including multiple UV-light emitting diodes (UV-LEDs) adjacent to the first UV diffuse reflective layer, wherein the positioning of the flexible circuit includes aligning the multiple UV-LEDs to correspond to the first gap.

E2. The method of E1, further comprising wrapping a second UV diffuse reflective layer in a second direction around the mandrel and the first UV diffuse reflective layer with a second gap between adjacent longitudinal sides of the second UV diffuse reflective layer, wherein the second UV diffuse reflective layer is flexible, and wherein a portion of the first gap and a portion of the second gap overlap to generate a plurality of openings.

E3. The method of E2, wherein the positioning the flexible circuit includes aligning the multiple UV-LEDs to correspond to the plurality openings.

E4. The method of E2, wherein each of the multiple UV-LEDs is positioned to direct generated UV light through a corresponding opening.

E5. The method of any one of E1-E4, wherein wrapping of the first UV diffuse reflective layer includes helically wrapping.

E6. The method of any one of E1-E5, wherein each of the multiple UV-LEDs is positioned to direct generated UV light through the first gap.

E7. The method of any one of E1-E6, wherein aligning the multiple UV-LEDs includes aligning one or more UV-LEDs of a first flexible circuit at a first subset of the plurality of openings and aligning one or more UV-LEDs of a second flexible circuit at a second subset of the plurality of openings.

E8. The method of E7, wherein the first subset of the plurality of openings and the second subset of the plurality of openings are positioned on opposite sides of the mandrel.

E9. The method of E7, wherein the first subset of the plurality of openings and the second subset of the plurality of openings are offset from one another.

E10. The method of any one of E1-E9, further comprising generating the flexible circuit.

E11. The method of E10, wherein generating the flexible circuit includes attaching the multiple UV-LEDs.

E12. The method of E11, wherein attaching the multiple UV-LEDs includes surface mounting the multiple UV-LEDs on the flexible circuit.

E13. The method of E10, wherein the flexible circuit comprises a ribbon cable or flat flexible cable and wherein generating the flexible circuit includes attaching the multiple UV-LEDs to the ribbon cable or flat flexible cable.

E14. The method of E13, wherein generating the flexible circuit further includes removing portions of a jacketing of the ribbon cable or flat flexible cable.

E15. The method of any one of E1-E14, further comprising wrapping an underlayer around the mandrel, the first UV diffuse reflective layer, and the flexible circuit.

E16. The method of E15, wherein the underlayer is a reinforcing underlayer.

E17. The method of E15, wherein the underlayer is a UV diffuse reflective underlayer.

E18. The method of E15, further comprising applying an adhesive between the underlayer the flexible circuit and the first UV diffuse reflective layer.

E19. The method of any one of E1-E18, further comprising wrapping an overlayer around the mandrel, wherein wrapping the first UV diffuse reflective layer around the mandrel includes wrapping the first UV diffuse reflective layer around the overlayer and the mandrel.

E20. The method of any one of E1-E18, further comprising positioning a tubular overlayer around the mandrel, wherein wrapping includes wrapping the first UV diffuse reflective layer around the tubular overlayer and the mandrel.

E21. The method of any one of E19 or E20, wherein the overlayer or tubular overlayer is a UV transparent overlayer, preferably having a UV transmission of at least 80% at 250 nm.

E22. The method of any one of E19 or E20, wherein the overlayer or tubular overlayer is a UV transmissive scattering overlayer.

E23. The method of any one E19 or E20, wherein the overlayer or tubular overlayer comprises a photocatalyst, preferably comprises TiO2.

E24. The method of any one of E19 or E20, further comprising applying an adhesive between the first UV diffuse reflective layer and the overlayer or tubular overlayer, preferably wherein the adhesive is a fluorinated ethylene propylene (FEP) adhesive.

E25. The method of any one of E1-E24, further comprising energizing the multiple UV-LEDs to generate UV light, wherein at least a portion of the generated UV light from the multiple UV-LEDs passes through the corresponding openings and into the fluid pathway.

E26. The method of any one of E1-E25, further comprising removing the mandrel.

E27. An ultraviolet (UV) light generation system made by the method of any one of E1-E26.

E28. An ultraviolet (UV) light generation system comprising: a first UV diffuse reflective layer arranged about a fluid pathway, wherein adjacent longitudinal sides of the first UV diffuse reflective layer are separated by a first gap, wherein the first gap runs in a first direction, and wherein the first UV diffuse reflective layer is flexible; a second UV diffuse reflective layer arranged about the first UV diffuse reflective layer, wherein adjacent longitudinal sides of the second UV diffuse reflective layer are separated by a second gap, wherein the second gap runs in a second direction, wherein the second UV diffuse reflective layer is flexible, and wherein the first and second gap overlap to generate a plurality of openings; and a flexible circuit including multiple UV-light emitting diodes (UV-LEDs), wherein the flexible circuit is positioned adjacent to the second UV diffuse reflective layer to align the multiple UV-LEDs at the plurality of openings.

E29. The UV light generation system of E28, wherein the first UV diffuse reflective layer is cylindrically wrapped about the fluid pathway, or wherein the second UV diffuse reflective layer is cylindrically wrapped about the first UV diffuse reflective layer, or both.

E30. The UV light generation system of E28 or E29, wherein the first UV diffuse reflective layer is helically wrapped about the fluid pathway, or wherein the second UV diffuse reflective layer is helically wrapped about the first UV diffuse reflective layer, or both.

E31. The UV light generation system of any one of E28-E30, further comprising an overlayer arranged about and defining the fluid pathway, wherein the first UV diffuse reflective layer is wrapped about the overlayer.

E32. The UV light generation system of E31, wherein the overlayer is a UV transparent overlayer, preferably having a UV transmission of at least 80% at 250 nm.

E33. The UV light generation system of E31, wherein the overlayer is a UV transmissive scattering overlayer.

E34. The UV light generation system of E31, wherein the overlayer comprises a photocatalyst, preferably comprises $TiO_2$.

E35. The UV light generation system of E31, wherein the overlayer covers at least a portion of the plurality of openings.

E36. The UV light generation system of E31, wherein the overlayer is UV stable.

E37. The UV light generation system of E31, wherein the overlayer is adhered to the first UV diffuse reflective layer or laminated to the first UV diffuse reflective layer, preferably the overlayer comprises a photocatalyst, and more preferably comprises $TiO_2$.

E38. The UV light generation system of any one of E28-E37, wherein the first UV diffuse reflective layer does not include UV absorbing filler material, or wherein the second UV diffuse reflective layer does not include UV absorbing filler material, or both.

E39. The UV light generation system of any one of E28-E38, wherein the first UV diffuse reflective layer is UV stable, or wherein the second UV diffuse reflective layer is UV stable or both.

E40. The UV light generation system of any one of E28-E39, further comprising an underlayer wrapped around the flexible circuit, the first UV diffuse reflective layer, and the second UV diffuse reflective layer.

E41. The UV light generation system of E40, wherein the underlayer is a reinforcing underlayer.

E42. The UV light generation system of E40, wherein the underlayer is a UV diffuse reflective underlayer.

E43. The UV light generation system of any one of E28-E42, wherein the multiple UV-LEDs are positioned to direct generated UV light into the fluid pathway.

E44. The UV light generation system of any one of E28-E43, wherein at least a first UV-LED of the multiple UV-LEDs is positioned in a configuration about the fluid pathway that is not directly opposed to any other of the multiple UV-LEDs.

E45. The UV light generation system of any one of E28-E44, wherein the fluid pathway corresponds to a tubular shape.

E46. The UV light generation system of any one of E28-E45, wherein the fluid pathway corresponds to a liquid pathway and wherein exposing a liquid stream in the liquid pathway to UV light generated by the multiple UV-LEDs reduces impurities within the liquid stream or reduces impurities associated with particles suspended in the liquid stream.

E47. The UV light generation system of any one of E28-E46, wherein the fluid pathway corresponds to a gas pathway and wherein exposing a gas stream in the gas pathway to UV light generated by the multiple UV-LEDs reduces impurities within the gas stream or reduces impurities associated with particles suspended in the gas stream.

E48. The UV light generation system of any one of E28-E47, wherein the flexible circuit further includes a UV sensitive photodetector, wherein the UV sensitive photodetector is positioned at one of the plurality of openings.

E49. The UV light generation system of any one of E28-E48, further comprising an adhesive layer for adhering two or more components of the UV light generation system to one another.

E50. The UV light generation system of E49, wherein the adhesive layer adheres a layer, an overlayer, or an underlayer to other components of the UV light generation system.

E51. The UV light generation system of E49, wherein the adhesive layer corresponds to a UV transparent layer, preferably wherein the adhesive is a fluorinated ethylene propylene (FEP) adhesive.

E52. The UV light generation system of E49, wherein the adhesive layer is UV stable.

E53. The UV light generation system of any one of E28-E52, wherein the flexible circuit corresponds to a ribbon cable or a flat flexible cable.

E54. The UV light generation system of any one of E28-E53, wherein each of the multiple UV-LEDs are individually electrically addressable.

E55. The UV light generation system of any one of E28-E54, wherein at least a portion of UV light generated by the multiple UV-LEDs is reflected by a UV diffuse reflective layer of the UV light generation system.

E56. The UV light generation system of any one of E28-E55, wherein the multiple UV-LEDs are positioned about the UV light generation system in a configuration to generate a uniform UV emission field within the fluid pathway.

E57. The UV light generation system of any one of E28-E56, wherein the fluid pathway includes straight or curved sections.

E58. The UV light generation system of any one of E28-E57, wherein one or more layers, underlayers, or overlayers of the UV light generation system are flexible or exhibit an elastic modulus of between 0.001 GPa and 3.0 GPa.

E59. The UV light generation system of any one of E28-E58, wherein one or more layers, underlayers, or overlayers of the UV light generation system comprise polytetrafluoroethylene or expanded-polytetrafluoroethylene (e-PTFE).

E60. The UV light generation system of any one of E28-E59 made by the method of any one of E1-E27.

E61. The method of any one of E1-E27, wherein the UV light generation system comprises the UV light generation system of any one of E28-E59.

E62. A method of making an ultraviolet (UV) light generation system, the method comprising: generating a plurality of openings in a UV diffuse reflective layer, wherein the UV diffuse reflective layer is flexible; and positioning a flexible circuit adjacent to the UV diffuse reflective layer, wherein the flexible circuit includes multiple UV-light emitting diodes (UV-LEDs), and wherein the multiple UV-LEDs are aligned at corresponding openings in the UV diffuse reflective layer.

E63. The method of E62, wherein generating the plurality of openings includes removing portions the UV diffuse reflective layer.

E64. The method of E62 or E63, further comprising generating the flexible circuit.

E65. The method of E64, wherein generating the flexible circuit includes attaching the multiple UV-LEDs on a flexible circuit.

E66. The method of E65, wherein attaching the multiple UV-LEDs includes surface mounting the multiple UV-LEDs on the flexible circuit.

E67. The method of E64, wherein the flexible circuit comprises a ribbon cable or flat flexible cable and wherein generating the flexible circuit includes attaching the multiple UV-LEDs to the ribbon cable or flat flexible cable.

E68. The method of E64, wherein generating the flexible circuit further includes removing portions of a jacketing of the ribbon cable or flat flexible cable.

E69. The method of any one of E62-E68, wherein the flexible circuit is a two-sided flexible circuit, wherein generating the plurality of openings in the UV diffuse reflective layer includes generating a first plurality of openings in a first UV diffuse reflective layer and generating a second plurality of openings in a second UV diffuse reflective layer UV, and wherein positioning the flexible circuit includes aligning a first portion of the multiple UV-LEDs that are present on a second side of the two-sided flexible circuit with corresponding openings of the first UV diffuse reflective layer and aligning a second portion of the multiple UV-LEDs that are present on a second side of the two-sided flexible circuit with corresponding openings of the second UV diffuse reflective layer, thereby making a two-sided UV light generation system.

E70. The method of any one of E62-E69, further comprising arranging the UV diffuse reflective layer and the flexible circuit such that at least portions of the flexible circuit are positioned back-to-back, thereby making a two-sided UV light generation system.

E71. The method of any one of E62-E70, further comprising arranging a second UV light generation system adjacent to the UV light generation system such that at least a portion of the flexible circuit is positioned adjacent to a portion of a second flexible circuit of the second UV light generation system, thereby making a two-sided UV light generation system.

E72. The method of any one of E62-E71, further comprising positioning a UV diffuse reflective underlayer adjacent to the flexible circuit.

E73. The method of E72, further comprising applying an adhesive between the UV diffuse reflective underlayer and the UV diffuse reflective layer.

E74. The method of E72, wherein the UV diffuse reflective underlayer is flexible.

E75. The method of any one of E62-E74, further comprising positioning an overlayer adjacent to the UV diffuse reflective layer.

E76. The method of E75, wherein the overlayer is a UV transparent overlayer, preferably having a UV transmission of at least 80% at 250 nm.

E77. The method of E75, further comprising applying an adhesive between the overlayer and the UV diffuse reflective layer, preferably wherein the adhesive is a fluorinated ethylene propylene (FEP) adhesive.

E78. The method of E75, wherein the overlayer is flexible.

E79. The method of E75, wherein the overlayer comprises a photocatalyst, preferably a TiO2 surface coating or wherein the UV transparent overlayer is attached to a TiO2 overlayer.

E80. The method of E75, further comprising applying a TiO2 surface coating to the overlayer or attaching a TiO2 further overlayer to the overlayer.

E81. The method of E75, wherein the overlayer is a UV transmissive scattering overlayer.

E82. The method of any one of E62-E81, further comprising heating the UV diffuse reflective layer.

E83. The method of any one of E62-E82, further comprising applying pressure to the UV diffuse reflective layer.

E84. The method of E82, wherein heating the UV diffuse reflective layer includes heating the UV diffuse reflective layer and an underlayer, an overlayer, or both an underlayer or an overlayer.

E85. The method of any one of E62-E84, further comprising energizing the multiple UV-LEDs to generate UV light, wherein at least a portion of the generated UV light from the multiple UV-LEDs passes through the corresponding openings in the UV diffuse reflective layer.

E86. The method of any one of E62-E85, further comprising wrapping the flexible circuit and the UV diffuse reflective layer around a mandrel.

E87. The method of E86, wherein wrapping includes helically, longitudinally, or circumferentially wrapping the flexible circuit and the UV diffuse reflective layer around the mandrel.

E88. The method of E86, further comprising wrapping an underlayer around the flexible circuit and the UV diffuse reflective layer.

E89. The method of E88, wherein the underlayer is a reinforcing underlayer.

E90. The method of E88, wherein the underlayer is a UV diffuse reflective underlayer.

E91. The method of E88, further comprising applying an adhesive between the underlayer and the flexible circuit, preferably wherein the adhesive is a fluorinated ethylene propylene (FEP) adhesive.

E92. The method of any one of E62-E91, further comprising wrapping an overlayer around the mandrel, wherein wrapping the flexible circuit and the UV diffuse reflective layer around the mandrel includes wrapping the flexible circuit and the UV diffuse reflective layer around the overlayer and the mandrel.

E93. The method of any one of E62-E91, further comprising positioning a tubular overlayer around the mandrel, wherein wrapping includes wrapping the flexible circuit and the UV diffuse reflective layer around the tubular overlayer and the mandrel.

E94. The method of any one of E92 or E93, wherein the overlayer or the tubular overlayer is a UV transparent overlayer, preferably having a UV transmission of at least 80% at 250 nm.

E95. The method of any one of E92 or E93, wherein the overlayer or the tubular overlayer is a UV transmissive scattering overlayer.

E96. The method of any one of E92 or E93, further comprising applying an adhesive between the UV diffuse reflective layer and the overlayer or the tubular overlayer, preferably wherein the adhesive is a fluorinated ethylene propylene (FEP) adhesive.

E97. The method of any one of E62-E96, further comprising removing the mandrel.

E98. An ultraviolet (UV) light generation system made by the method of any one of E62-E97.

E99. An ultraviolet (UV) light generation system comprising: a flexible circuit including multiple ultraviolet light emitting diodes (UV-LEDs); and a UV diffuse reflective layer adjacent to the multiple UV-LEDs, wherein the UV diffuse reflective layer is flexible, wherein the UV diffuse reflective layer includes multiple openings, and wherein each UV-LED is positioned at a corresponding opening.

E100. The UV light generation system of E99, further comprising an overlayer adjacent to the UV diffuse reflective layer.

E101. The UV light generation system of E100, wherein the overlayer is a UV transparent overlayer, preferably having a UV transmission of at least 80% at 250 nm.

E102. The UV light generation system of E100, wherein the overlayer is a UV transmissive scattering overlayer.

E103. The UV light generation system of E100, wherein the overlayer comprises a photocatalyst, preferably a TiO2 surface coating or wherein the UV transparent overlayer is attached to a TiO2 overlayer.

E104. The UV light generation system of E100, wherein the overlayer covers multiple openings in the UV diffuse reflective layer.

E105. The UV light generation system of E100, wherein the overlayer does not include UV absorbing filler material.

E106. The UV light generation system of E100, wherein the overlayer is UV stable.

E107. The UV light generation system of E100, wherein the overlayer is adhered to the UV diffuse reflective layer or laminated to the UV diffuse reflective layer.

E108. The UV light generation system of any one of E99-E107, wherein the UV diffuse reflective layer is UV stable.

E109. The UV light generation system of any one of E99-E108, further comprising an underlayer positioned adjacent to the UV flexible circuit.

E110. The UV light generation system of E109, wherein the underlayer is a reinforcing underlayer.

E111. The UV light generation system of E109, wherein the underlayer is a UV diffuse reflective underlayer.

E112. The UV light generation system of any one of E99-E111, arranged to define an enclosed region, wherein the multiple UV-LEDs are positioned to direct generated UV light into the enclosed region.

E113. The UV light generation system of E112, arranged to position at least a first UV-LED of the multiple UV-LEDs in a configuration about the enclosed region that is not directly opposed to any other of the multiple UV-LEDs.

E114. The UV light generation system of E112, wherein the enclosed region corresponds to a fluid pathway.

E115. The UV light generation system of E113, wherein the UV light generation system is arranged to form a tubular shape corresponding to the fluid pathway.

E116. The UV light generation system of E113, wherein the UV light generation system is wrapped helically, longitudinally, or circumferentially around the fluid pathway.

E117. The UV light generation system of E113, wherein the fluid pathway corresponds to a liquid pathway and wherein exposing a liquid stream in the liquid pathway to UV light generated by the multiple UV-LEDs reduces impurities within the liquid stream or reduces impurities associated with particles suspended in the liquid stream.

E118. The UV light generation system of E113, wherein the fluid pathway corresponds to a gas pathway and wherein exposing a gas stream in the gas pathway to UV light generated by the multiple UV-LEDs reduces impurities within the gas stream or reduces impurities associated with particles suspended in the gas stream.

E119. The UV light generation system of E112, wherein at least two portions of the UV light generation system are positioned to oppose one another and define the enclosed region.

E120. The UV light generation system of any one of E99-E119, arranged along an interior surface of a vessel, wherein the multiple UV-LEDs are positioned to direct generated UV light into an interior of the vessel.

E121. The UV light generation system of any one of E99-E120, arranged along a surface of a structure positioned within a vessel, wherein the multiple UV-LEDs are positioned to direct generated UV light into an interior of the vessel.

E122. The UV light generation system of any one of E99-E121, arranged around a central shaft, wherein the multiple UV-LEDs are positioned to direct generated UV away from the central shaft.

E123. The UV light generation system of E122, wherein the UV light generation system is wrapped helically, longitudinally, or circumferentially around the central shaft.

E124. The UV light generation system of E122, wherein the multiple UV-LEDs are positioned around the central shaft in a configuration to generate a uniform UV emission field at a circumferential distance from the central shaft.

E125. The UV light generation system of any one of E99-E124, arranged as a two-sided sheet, wherein the multiple UV-LEDs are positioned to direct generated UV light outward and away from the two-sided sheet.

E126. The UV light generation system of E125, wherein UV-LEDs positioned on a first side of the two-sided sheet do not back to any UV-LEDs positioned on a second side of the two-sided sheet.

E127. The UV light generation system of any one of E99-E126, wherein the flexible circuit further includes a UV sensitive photodetector, wherein the UV sensitive photodetector is positioned at one of the multiple openings of the UV diffuse reflective layer.

E128. The UV light generation system of any one of E99-E127, further comprising an adhesive layer for adhering two or more components of the UV light generation system to one another.

E129. The UV light generation system of E128, wherein the adhesive layer adheres an overlayer or an underlayer to other components of the UV light generation system.

E130. The UV light generation system of E128, wherein the adhesive layer corresponds to a UV transparent layer.

E131. The UV light generation system of E128, wherein the adhesive layer is UV stable.

E132. The UV light generation system of any one of E99-E131, wherein the flexible circuit corresponds to a ribbon cable or a flat flexible cable.

E133. The UV light generation system of any one of E99-E132, wherein each of the multiple UV-LEDs are individually electrically addressable.

E134. The UV light generation system of any one of E99-E133, wherein at least a portion of UV light generated by the multiple UV-LEDs is reflected by a UV diffuse reflective layer of the UV light generation system.

E135. The UV light generation system of any one of E99-E134, wherein the multiple UV-LEDs are positioned about the UV light generation system in a configuration to generate a uniform UV emission field at a distance away from the UV diffuse reflective layer.

E136. The UV light generation system of any one of E99-E135, including one or more flat, concave, or convex sections.

E137. The UV light generation system of any one of E99-E136, wherein the array corresponds to a regular array or a non-regular array.

E138. The UV light generation system of any one of E99-E137, wherein one or more layers, underlayers, or overlayers of the UV light generation system are flexible or exhibit an elastic modulus of between 0.001 GPa and 3.0 GPa.

E139. The UV light generation system of any one of E99-E138, wherein one or more layers, underlayers, or overlayers of the UV light generation system comprise polytetrafluoroethylene or expanded-polytetrafluoroethylene (e-PTFE).

E140. The UV light generation system of any one of E99-E139 made by the method of any one of E62-E98.

E141. The method of any one of E62-E98, wherein the UV light generation system comprises the UV light generation system of any one of E99-E139.

E142. A method of making an ultraviolet (UV) light generation system, the method comprising: wrapping a first UV diffuse reflective layer in a first direction around a mandrel with a first gap between adjacent longitudinal sides of the first UV diffuse reflective layer, wherein the first UV diffuse reflective layer is flexible; wrapping a second UV diffuse reflective layer in a second direction around the mandrel and the first UV diffuse reflective layer with a second gap between adjacent longitudinal sides of the second UV diffuse reflective layer, wherein the second UV diffuse reflective layer is flexible, and wherein a portion of the first gap and a portion of the second gap overlap to generate a plurality of openings and positioning a flexible circuit including multiple UV-light emitting diodes (UV-LEDs) adjacent to the first UV diffuse reflective layer, wherein the positioning of the flexible circuit includes aligning the multiple UV-LEDs to correspond to the plurality of openings.

E143. The method of E142, wherein each of the multiple UV-LEDs is positioned to direct generated UV light through a corresponding opening.

Various modifications and additions can be made to the exemplary embodiments of the disclosed treatment systems discussed without departing from the scope of the present invention. While the embodiments described above refer to particular features, the scope of this invention also includes embodiments having different combinations of features and embodiments that do not include all of the above described features. It will be appreciated that features of the various embodiments and examples described herein may be combined with one another in any suitable combination and that the disclosed embodiments are not limiting. For example, features in one embodiment may optionally be imported into another embodiment if it is possible to do so.

What is claimed is:

1. A method of making a flexible ultraviolet (UV) light generation system, the method comprising:
    generating a plurality of openings in a UV diffuse reflective layer,
        wherein the UV diffuse reflective layer is flexible;
    positioning a flexible circuit adjacent to the UV diffuse reflective layer,
        wherein the flexible circuit comprises multiple UV-light emitting diodes (UV-LEDs), and
        wherein the multiple UV-LEDs are aligned at corresponding openings of the plurality of openings in the UV diffuse reflective layer;
    positioning a flexible overlayer adjacent to the UV diffuse reflective layer,
        wherein the overlayer is an encapsulating UV transparent or UV transmissive scattering layer; and
    joining or adhering the flexible circuit, the UV diffuse reflective layer and the overlayer to form a composite structure.

2. The method of claim 1, wherein generating the plurality of openings comprises removing portions of the UV diffuse reflective layer.

3. The method of claim 1, further comprising generating the flexible circuit.

4. The method of claim 1, wherein the flexible circuit is a two-sided flexible circuit,
    wherein generating the plurality of openings in the UV diffuse reflective layer comprises:
        generating a first plurality of openings in a first UV diffuse reflective layer;
        and generating a second plurality of openings in a second UV diffuse reflective layer UV, and
    wherein positioning the flexible circuit comprises:
        aligning a first portion of the multiple UV-LEDs that are present on a second side of the two-sided flexible circuit with corresponding openings of the first UV diffuse reflective layer; and
        aligning a second portion of the multiple UV-LEDs that are present on a second side of the two-sided flexible circuit with corresponding openings of the second UV diffuse reflective layer to form a two-sided UV light generation system.

5. The method of claim 1, further comprising arranging the UV diffuse reflective layer and the flexible circuit such that at least portions of the flexible circuit are positioned back-to-back to form a two-sided UV light generation system.

6. The method of claim 1, further comprising arranging a second UV light generation system adjacent to the UV light generation system such that at least a portion of the flexible circuit is positioned adjacent to a portion of a second flexible circuit of the second UV light generation system to form a two-sided UV light generation system.

7. The method of claim 1, further comprising positioning a UV diffuse reflective underlayer adjacent to the flexible circuit.

8. The method of claim 7, further comprising applying an adhesive between the UV diffuse reflective underlayer and the UV diffuse reflective layer.

9. The method of claim 1, further comprising applying an adhesive between the overlayer and the UV diffuse reflective layer.

10. The method of claim 1, wherein the overlayer comprises a photocatalyst or wherein the UV transparent overlayer is attached to a TiO2 overlayer.

11. The method of claim 1, further comprising applying a TiO2 surface coating to the overlayer or attaching a TiO2 further overlayer to the overlayer.

12. The method of claim 1, further comprising wrapping the flexible circuit and the UV diffuse reflective layer around a mandrel.

13. The method of claim 12, further comprising wrapping an underlayer around the flexible circuit and the UV diffuse reflective layer.

14. The method of claim 13, further comprising applying an adhesive between the underlayer and the flexible circuit.

15. The method of claim 1, further comprising wrapping an overlayer around a mandrel, wherein wrapping the flexible circuit and the UV diffuse reflective layer around the mandrel comprises wrapping the flexible circuit and the UV diffuse reflective layer around the overlayer and the mandrel.

16. The method of claim 15, further comprising applying an adhesive between the UV diffuse reflective layer and the overlayer or tubular overlayer.

17. The method of claim 1, further comprising positioning a tubular overlayer around a mandrel, wherein wrapping comprises wrapping the flexible circuit and the UV diffuse reflective layer around the tubular overlayer and the mandrel.

18. The method of claim 1, further comprising removing a mandrel.

19. A flexible ultraviolet (UV) light generation system made by the method of claim 1.

20. A method of making an ultraviolet (UV) light generation system, the method comprising:
- generating a plurality of openings in a UV diffuse reflective layer,
  - wherein the UV diffuse reflective layer is flexible;
- positioning a flexible circuit adjacent to the UV diffuse reflective layer,
  - wherein the flexible circuit comprises multiple UV-light emitting diodes (UV-LEDs),
  - wherein the multiple UV-LEDs are aligned at corresponding openings of the plurality of openings in the UV diffuse reflective layer; and
- applying an adhesive between the overlayer and the UV diffuse reflective layer.

\* \* \* \* \*